(12) United States Patent
Ritter et al.

(10) Patent No.: US 9,273,083 B2
(45) Date of Patent: Mar. 1, 2016

(54) NICKEL FLUORINATING COMPLEXES AND USES THEREOF

(71) Applicant: President and Fellows of Harvard College, Cambridge, MA (US)

(72) Inventors: Tobias Ritter, Cambridge, MA (US); Eunsung Lee, Pohang (KR)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/431,371

(22) PCT Filed: Sep. 26, 2013

(86) PCT No.: PCT/US2013/061968
§ 371 (c)(1),
(2) Date: Mar. 26, 2015

(87) PCT Pub. No.: WO2014/052622
PCT Pub. Date: Apr. 3, 2014

(65) Prior Publication Data
US 2015/0252067 A1 Sep. 10, 2015

Related U.S. Application Data

(60) Provisional application No. 61/782,119, filed on Mar. 14, 2013, provisional application No. 61/705,980, filed on Sep. 26, 2012.

(51) Int. Cl.
| | | |
|---|---|---|
| *C07F 15/04* | (2006.01) | |
| *C07B 39/00* | (2006.01) | |
| *C07C 67/287* | (2006.01) | |
| *C07C 17/093* | (2006.01) | |
| *C07C 269/06* | (2006.01) | |

(Continued)

(52) U.S. Cl.
CPC .............. *C07F 15/04* (2013.01); *C07B 39/00* (2013.01); *C07C 17/093* (2013.01); *C07C 17/361* (2013.01); *C07C 67/287* (2013.01); *C07C 67/293* (2013.01); *C07C 269/06* (2013.01); *C07J 43/003* (2013.01); *C07B 2200/05* (2013.01); *C07C 2101/14* (2013.01)

(58) Field of Classification Search
None
See application file for complete search history.

(56) References Cited

U.S. PATENT DOCUMENTS 3,136,774 A 6/1964 Stoffel
3,136,776 A 6/1964 Stoffel
(Continued)

FOREIGN PATENT DOCUMENTS

CN 1263882 A 8/2000
CN 1897891 A1 1/2007
(Continued)

OTHER PUBLICATIONS

Lee et al., J. Am. Chem. Soc., 2012, 134 (42), pp. 17456-17458, Publication Date (Web): Oct. 12, 2012.*
(Continued)

*Primary Examiner* — Karl J Puttlitz
(74) *Attorney, Agent, or Firm* — Wolf, Greenfield & Sacks, P.C.

(57) ABSTRACT

The present invention provides novel nickel complexes. These complexes are in providing fluorinating organic compounds. The invention is particularly useful for fluorinating compounds with $^{18}$F for PET imaging.

20 Claims, 20 Drawing Sheets

(51) Int. Cl.
C07C 17/361 (2006.01)
C07C 67/293 (2006.01)
C07J 43/00 (2006.01)

(56) References Cited

U.S. PATENT DOCUMENTS

| | | | |
|---|---|---|---|
| 3,137,701 | A | 6/1964 | Ayer |
| 3,641,153 | A | 2/1972 | Kyburz et al. |
| 3,972,936 | A | 8/1976 | Christy |
| 3,991,103 | A | 11/1976 | Barton et al. |
| 4,236,008 | A | 11/1980 | Henderson |
| 4,402,956 | A | 9/1983 | Silvestrini et al. |
| 4,487,773 | A | 12/1984 | Temple, Jr. et al. |
| 4,578,222 | A | 3/1986 | Ishikawa et al. |
| 6,069,110 | A | 5/2000 | Klaui et al. |
| 6,127,583 | A | 10/2000 | Sonoda et al. |
| 6,160,158 | A * | 12/2000 | Bartlett et al. ............ 558/460 |
| 7,108,846 | B1 | 9/2006 | Marchand et al. |
| 7,115,249 | B2 | 10/2006 | Luthra et al. |
| 8,686,158 | B2 | 4/2014 | Furuya et al. |
| 9,024,093 | B2 | 5/2015 | Ritter et al. |
| 2005/0085474 | A1 | 4/2005 | Ebenbeck et al. |
| 2005/0137421 | A1 | 6/2005 | Walsh et al. |
| 2006/0083677 | A1 | 4/2006 | Brady et al. |
| 2007/0092441 | A1 | 4/2007 | Wadsworth et al. |
| 2009/0247517 | A1 | 10/2009 | Liu et al. |
| 2011/0054175 | A1 | 3/2011 | Ritter et al. |
| 2011/0212936 | A1 | 9/2011 | Furuya et al. |
| 2011/0312903 | A1 | 12/2011 | Ritter et al. |
| 2012/0095217 | A1 | 4/2012 | Ritter et al. |
| 2012/0149900 | A1 | 6/2012 | Ritter et al. |
| 2012/0316120 | A1 | 12/2012 | Ritter |
| 2012/0316341 | A1 | 12/2012 | Ritter et al. |
| 2014/0018538 | A1 | 1/2014 | Lee et al. |
| 2014/0058106 | A1 | 2/2014 | Ritter et al. |

FOREIGN PATENT DOCUMENTS

| | | | |
|---|---|---|---|
| DE | 23 60 940 A1 | 4/1975 | |
| EP | 0 618 491 A1 | 10/1994 | |
| EP | 0 915 094 A1 | 5/1999 | |
| EP | 1 013 629 A1 | 6/2000 | |
| GB | 1 177 525 A | 1/1970 | |
| JP | 63-166159 A | 7/1988 | |
| JP | 2001-322984 A | 11/2001 | |
| WO | 03/020732 A2 | 3/2003 | |
| WO | 2005/063254 A2 | 7/2005 | |
| WO | 2005/117872 A2 | 12/2005 | |
| WO | 2006/078752 A2 | 7/2006 | |
| WO | 2008/081477 A1 | 7/2008 | |
| WO | 2008/091818 A1 | 7/2008 | |
| WO | 2009/033751 A2 | 3/2009 | |
| WO | 2009/100014 A1 | 8/2009 | |
| WO | 2009/141053 A1 | 11/2009 | |
| WO | 2009/149347 A1 | 12/2009 | |
| WO | 2010/059943 A2 | 5/2010 | |
| WO | 2010/081034 A2 | 7/2010 | |
| WO | 2010/081036 A2 | 7/2010 | |
| WO | 2011/006088 A2 | 1/2011 | |
| WO | 2012/024604 A2 | 2/2012 | |
| WO | 2012/054782 A2 | 4/2012 | |
| WO | 2012/142162 A2 | 10/2012 | |

OTHER PUBLICATIONS

Invitation to Pay Additional Fees for PCT/US2014/061066, mailed Jan. 12, 2015.
International Search Report and Written Opinion for PCT/US2014/061066, mailed May 8, 2015.
Invitation to Pay Additional Fees for PCT/US2013/061968, mailed Jan. 3, 2014.
International Search Report and Written Opinion for PCT/US2013/061968, mailed Mar. 7, 2014.
International Preliminary Report on Patentability for PCT/US2013/061968, mailed Apr. 9, 2015.
Extended European Search Report for EP 09759505.2, mailed Jan. 20, 2012.
International Search Report and Written Opinion for PCT/US2009/046401, mailed Sep. 22, 2009.
International Preliminary Report on Patentability for PCT/US2009/046401, mailed Dec. 16, 2010.
International Search Report and Written Opinion for PCT/US2009/032855, mailed Jun. 8, 2009.
International Preliminary Report on Patentability for PCT/US2009/032855, mailed Aug. 12, 2010.
Invitation to Pay Additional Fees for PCT/US2010/041561, mailed Sep. 28, 2010.
International Search Report and Written Opinion for PCT/US2010/041561, mailed Jun. 15, 2011.
International Preliminary Report on Patentability for PCT/US2010/041561, mailed Jan. 19, 2012.
Extended European Search Report for EP 10729595.8, mailed May 22, 2013.
International Search Report and Written Opinion for PCT/US2010/020544, mailed Oct. 7, 2010.
International Preliminary Report on Patentability for PCT/US2010/020544, mailed Jul. 21, 2011.
Extended European Search Report for EP 09828291.6, mailed May 18, 2012.
International Search Report and Written Opinion for PCT/US2009/065339, mailed Jul. 12, 2010.
International Preliminary Report on Patentability for PCT/US2009/065339, mailed Jun. 3, 2011.
International Search Report and Written Opinion for PCT/US2011/048451, mailed Mar. 22, 2012.
International Preliminary Report on Patentability for PCT/US2011/048451, mailed Mar. 7, 2013.
Extended European Search Report for EP 11818838.2, mailed Dec. 10, 2013.
International Search Report and Written Opinion for PCT/US2012/033125, mailed Nov. 9, 2012.
International Preliminary Report on Patentability for PCT/US2012/033125, mailed Oct. 24, 2013.
Extended European Search Report for EP 12771755.1, mailed Aug. 5, 2014.
Extended European Search Report for EP 10729593.3, mailed May 3, 2012.
International Search Report and Written Opinion for PCT/US2010/020540, mailed Oct. 6, 2010.
International Preliminary Report on Patentability for PCT/US2010/020540, mailed Jul. 21, 2011.
International Search Report and Written Opinion for PCT/US2011/057176, mailed May 3, 2012.
International Preliminary Report on Patentability for PCT/US2011/057176, mailed May 2, 2013.
International Search Report and Written Opinion for PCT/US2015/028446, mailed Jul. 27, 2015.
Database Accession No. CID 5255788. Oct. 7, 2005.
Adams et al., Nucleophilic routes to selectively fluorinated aromatics. Chem Soc Rev. 1999;28:225-231.
Alvarez-Corral et al., Silver-mediated synthesis of heterocycles. Chem Rev. Aug. 2008;108(8):3174-3198. doi: 10.1021/cr0783611. Epub Jul. 17, 2008.
Andrae et al., Energy-adjustedab initio pseudopotentials for the second and third row transition elements. Theor Chem Acta. 1990;77(2):123-41.
Andrae et al., Energy-adjustedab initio pseudopotentials for the second and third row transition elements: Molecular test for M2 (M=Ag, Au) and MH (M=Ru, Os). Theor Chim Acta. 1991;78(4):247-66.
Balz et al., Über aromatische Fluorverbindungen, I.: Ein neues Verfahren zu ihrer Darstellung. Ber Deut Chem Ges. 1927;60:1186-90.
Becke, Density-functional thermochemistry. III. The role of exact exchange. J Chem Phys. 1993;98(7): 5648-52.
Berge et al., Pharmaceutical Salts. J. Pharmaceutical Sciences 1977;66:1-19.
Bergman et al., Fluorine-18-labeled fluorine gas for synthesis of tracer molecules. Nucl Med Biol. Oct. 1997;24(7):677-83.

(56) References Cited

OTHER PUBLICATIONS

Billingsley et al., Palladium-catalyzed borylation of aryl chlorides: scope, applications, and computational studies. Angew Chem. 2007;119(28):5455-59.

Black et al., Observations on the mechanism of halogen-bridge cleavage by unidentate ligands in square planar palladium and platinum complexes. Australian Journal of Chemistry. 1994;47(2):217-227.

Bohm et al., Fluorine in medicinal chemistry. Chembiochem. May 3, 2004;5(5):637-43.

Brazier et al., The condensation of alpha-Keto-beta-anilino-alphabeta-diphenyl ethane and its Homologues with phenylcarbimide and with phenylthiocarbimide. J Chem Soc. 1912;101:2352-58.

Brown et al., Transition-metal-mediated reactions for C(sp2)-F bond construction: the state of play. Angew Chem Int Ed Engl. 2009;48(46):8610-8614. doi: 10.1002/anie.200902121.

Cámpora et al., Redox Behavior of an Organometallic Palladium(II)/Palladium(IV) System. A New Method for the Synthesis of Cationic Palladium(IV) Complexes. Organometallics. 2005;24(15):3624-3628.

Canty et al., Carbon—Oxygen Bond Formation at Metal(IV) Centers: Reactivity of Palladium(II) and Platinum(II) Complexes of the [2,6-(Dimethylaminomethyl)phenyl-N,C,N]- (Pincer) Ligand toward Iodomethane and Dibenzoyl Peroxide; Structural Studies of M(II) and M(IV) Complexes. Organometallics. 2004;23(23):5432-5439.

Canty et al., Synthesis and Characterization of Ambient Temperature Stable Organopalladium(IV) Complexes, Including Aryl-, .eta.1-Allyl-, Ethylpalladium(IV), and Pallada(IV)cyclopentane Complexes. Structures of the Poly(pyrazol-1-yl)borate Complexes PdMe3{(pz)3BH} and PdMe3{(pz)4B} and Three Polymorphs of PdMe2Et{(pz)3BH}. Organometallics. 1995;14(1):199-206.

Canty et al., Synthesis of halogeno, pseudohalogeno, and carboxylatopalladium(IV) complexes by halogen exchange. Crystal structure of azido(2,2'-bipyridyl)-benzylpalladium(II), formed on reductive elimination of ethane from Pd(N3)Me2(CH2Ph)(bpy). J Organometallic Chem. 1992;433(1-2):213-22.

Casitas et al., Nucleophilic aryl fluorination and aryl halide exchange mediated by a Cu(I)/Cu(III) catalytic cycle. J Am Chem Soc. Dec. 7, 2011;133(48):19386-92. doi: 10.1021/ja2058567. Epub Nov. 14, 2011.

Chan et al., Palladium(II)-catalyzed selective monofluorination of benzoic acids using a practical auxiliary: a weak-coordination approach. Angew Chem Int Ed Engl. Sep. 19, 2011;50(39):9081-4. doi: 10.1002/anie.201102985. Epub Jul. 11, 2011.

Chuang et al., A dinuclear palladium catalyst for a-hydroxylation of carbonyls with O2. J Am Chem Soc. Feb. 16, 2011;133(6):1760-2. doi: 10.1021/ja108396k. Epub Jan. 19, 2011.

Constaninou et al., Xenon difluoride exchanges fluoride under mild conditions: a simple preparation of [(18)F]xenon difluoride for PET and mechanistic studies. J Am Chem Soc. Feb. 28, 2001;123(8):1780-1.

Cope et al., Electrophilic aromatttic substitution reactions by platinum(II) and palladium(II) chlorides on N,N-dimethylbenzylamines. J Am Chem Soc. 1968;90(4):909-913.

Couturier et al., Fluorinated tracers for imaging cancer with positron emission tomography. Eur J Nucl Med Mol Imaging. Aug. 2004;31(8):1182-206. Epub Jul. 6, 2004.

Danielson et al., Use of 19F NMR to probe protein structure and conformational changes. Annu Rev Biophys Biomol Struct. 1996;25:163-95.

Dick et al., A highly selective catalytic method for the oxidative functionalization of C—H bonds. J Am Chem Soc. Mar. 3, 2004;126(8):2300-1.

Dick et al., Carbon—Nitrogen Bond-Forming Reactions of Palladacycles with Hypervalent Iodine Reagents. Organometallics. 2007;26(6):1365-1370.

Dick et al., Unusually stable palladium(IV) complexes: detailed mechanistic investigation of C—O bond-forming reductive elimination. J Am Chem Soc. Sep. 21, 2005;127(37):12790-1.

Edwards et al., In vitro and in vivo studies of neutral cyclometallated complexes against murine leukxmias. Canadian Journal of Chemistry. 2005;83(6-7):980-989.

Ehlers et al., A set of f-polarization functions for pseudo-potential basis sets of the transition metals Sc Cu, Y Ag and La Au. Chem Phys Lett. 1993;208(1-2):111-14.

Espinet et al., (CN)—chelate, N,N'-bridged dimeric palladium complexes derived from hydrazones PhC(R):NN' HPh. X-ray structure of [Pd(o-C6H4C(R):NNPh)L]2 [R=Me, L=P(OMe)3]. Inorg Chem., 1989;28(23):4207-4211.

Evans, The determination of the paramagnetic susceptibility of substances in solution by nuclear magnetic resonance. J Chem Soc. 1959;2003-2005.

Fier et al., Copper-mediated fluorination of aryl iodides. J Am Chem Soc. Jul. 4, 2012;134(26):10795-8. doi: 10.1021/ja304410x. Epub Jun. 22, 2012.

Fier et al., Copper-mediated fluorination of arylboronate esters. Identification of a copper(III) fluoride complex. J Am Chem Soc. Feb. 20, 2013;135(7):2552-9. doi: 10.1021/ja310909q. Epub Feb. 5, 2013.

Folgado et al., Fluxionality in hexacoordinated copper(II) complexes with 2,2':6',2"-terpyridine (terpy) and related ligands: structural and spectroscopic investigations. Inorg Chem. 1990;29(11):2035-2042.

Ford et al., Regioselectivity in metallation reactions of 2-(2'-naphthyl)pyridine: 1'-versus 3'-reactivity in mercuration and palladation reactions. Crystal structure of chloro(pyridine) [2-(2—pyridiny)naphthyl-C3,N]palladium. J Organometallic Chem. 1995;493(1-2):215-20.

Fraser et al., Molecular Fluoro Palladium Complexes. J Am Chem Soc. 1997;119(20):4769-70.

Fujimoto et al., PhenoFluor: Practical Synthesis, New Formulation, and Deoxyfluorination of Heteroaromatics. Org Process Res Dev. Aug. 15, 2014;18(8):1041-1044. Epub Jul. 23, 2014.

Furuya et al., Carbon-Fluorine Bond Formation for the Synthesis of Aryl Fluorides. Synthesis. 2010;11:1804-1821.

Furuya et al., Carbon-fluorine bond formation. Curr Opin Drug Discov Devel. Nov. 2008;11(6): 803-19.

Furuya et al., Carbon-fluorine reductive elimination from a high-valent palladium fluoride. J Am Chem Soc. Aug. 6, 2008;130(31):10060-1. doi: 10.1021/ja803187x. Epub Jul. 11, 2008.

Furuya et al., Catalysis for fluorination and trifluoromethylation. Nature. May 26, 2011;473(7348):470-7. doi: 10.1038/nature10108.

Furuya et al., Fluorination of boronic acids mediated by silver(I) triflate. Org Lett. Jul. 2, 2009;11(13):2860-3. doi: 10.1021/ol901113t.

Furuya et al., Mechanism of C—F reductive elimination from palladium(IV) fluorides. J Am Chem Soc. Mar. 24, 2010;132(11):3793-807. doi: 10.1021/ja909371t.

Furuya et al., Palladium-mediated fluorination of arylboronic acids. Angew Chem Int Ed Engl. 2008;47(32):5993-6. doi: 10.1002/anie.200802164.

Furuya et al., Silver-mediated fluorination of functionalized aryl stannanes. J Am Chem Soc. Feb. 11, 2009;131(5):1662-3. doi: 10.1021/ja8086664.

Gilicinski et al., On the relative power of electrophilic fluorinating reagents of the N F class. J Fluor Chem. 1992;59(1):157-162.

Grushin et al., Ar—F Reductive Elimination from Palladium(II) Revisited. Organometallics. 2007;26(20):4997-5002.

Grushin et al., Facile Ar-CF3 bond formation at Pd. Strikingly different outcomes of reductive elimination from [(Ph3P)2Pd(CF3)Ph]and [(Xantphos)Pd(CF3)Ph]. J Am Chem Soc. Oct. 4, 2006;128(39):12644-5.

Grushin et al., Is fluoride bonded to two Pd acceptors still basic? Three CH2Cl2 molecules encapsulating a Pd2(mu-F)2 square and new implications for catalysis. Angew Chem Int Ed Engl. Dec. 2, 2002;41(23):4476-9.

Grushin et al., Palladium Fluoride Complexes: One More Step toward Metal-Mediated C—F Bond Formation. Chemistry—A European Journal. 2002;8(5):1006-14.

Gullick et al., Catalytic asymmetric heterogeneous aziridination of styrene using Cu2+-exchanged zeolite Y: effect of the counter-cation on enantioselectivity and on the reaction profile. New J Chem. 2004;28:1470-1478.

(56) References Cited

OTHER PUBLICATIONS

Hartwell et al., The formation of palladium(II)—and platinum(II)—carbon bonds by proton abstraction from benzo[h]quinoline and 8-methylquinoline. J Chem Soc D. 1970:912.

Hauchecorne et al., Halogen bonding to a divalent sulfur atom: an experimental study of the interactions of CF3X (X=Cl, Br, I) with dimethyl sulfide. Phys Chem Chem Phys. Jun. 7, 2011;13(21):10204-13. doi: 10.1039/c0cp02960b. Epub Apr. 20, 2011.

Hayashi et al., 2,2-Difluoro-1,3-dimethylimidazolidine (DFI). A new fluorinating agent. Chem Commun (Camb). Aug. 7, 2002;(15):1618-9. Chem Commun (Camb). Aug. 7, 2002; (15): 1618-9.

Henriksen et al., Syntheses, biological evaluation, and molecular modeling of 18F-labeled 4-anilidopiperidines as mu-opioid receptor imaging agents. J Med Chem. Dec. 1, 2005;48(24):7720-32.

Holschumacher et al., Sulfur and Selenium Activation by Frustrated NHC/B(C6F5)3 Lewis Pairs; Conformational Flexibility of Products. Z Naturforsch.. 2011;66b:371-77.

Huang et al., Silver-mediated trifluoromethoxylation of aryl stannanes and arylboronic acids. J Am Chem Soc. Aug. 31, 2011;133(34):13308-10. doi: 10.1021/ja204861a. Epub Aug. 9, 2011.

Hull et al., Palladium-catalyzed fluorination of carbon-hydrogen bonds. J Am Chem Soc. Jun. 7, 2006;128(22):7134-5.

Jasim et al., Contrasting Reactivity of Fluoropyridines at Palladium and Platinum: C—F Oxidative Addition at Palladium, P—C and C—F Activation at Platinum. Organometallics 2004;23(26):6140-49.

Jeschke, The Unique Role of Fluorine in the Design of Active Ingredients for Modern Crop Protection. ChemBioChem. 2004;5(5):570-589.

Julia et al., Orientation de la palladation du noyau naphtalenique dans les α et β dimethylaminomethyl naphtalenes. J Organometallic Chem. 1975;102(2):239-43.

Kamlet et al., Application of palladium-mediated (18)F-fluorination to PET radiotracer development: overcoming hurdles to translation. PLoS One. 2013;8(3):e59187. doi: 10.1371/journal.pone.0059187. Epub Mar. 12, 2013.

Kaspi et al., Xenon difluoride induced aryl iodide reductive elimination: a simple access to difluoropalladium(II) complexes. Inorg Chem. Jan. 7, 2008;47(1):5-7. Epub Dec. 4, 2007.

Khusnutdinova et al., The aerobic oxidation of a Pd(II) dimethyl complex leads to selective ethane elimination from a Pd(III) intermediate. J Am Chem Soc. Feb. 1, 2012;134(4):2414-22. doi: 10.1021/ja210841f. Epub Jan. 20, 2012.

Kilbourn et al., Fluorine-18 labeling of proteins. J Nucl Med. Apr. 1987;28(4):462-70.

Kirk, Fluorination in Medicinal Chemistry: Methods, Strategies, and Recent Developments. Org Process Res Dev. 2008;12(2):305-321.

Laali et al., N-(trifluoromethylsulfonyl)aryloxytrifluoromethylsulfoximines [ArO—So(CF3)=NTf]and N-aryltriflimides Ar-N(Tf)2 by thermal and photolytic dediazoniation of [ArN2][BF4]in [BMIM][Tf2N]ionic liquid: exploiting the ambident nucleophilic character of a "nonnucleophilic" anion. J Org Chem. Aug. 31, 2007;72(18):6758-62. Epub Aug. 1, 2007.

Lanci et al., Oxidatively induced reductive elimination from ((t)Bu2bpy)Pd(Me)2: palladium(IV) intermediates in a one-electron oxidation reaction. J Am Chem Soc. Nov. 4, 2009;131(43):15618-20. doi: 10.1021/ja905816q.

Larsen et al., Halogen Complexes. III. The Association of 2,4,6-Trimethylpyridine and Trifluoroiodomethane. J Phys Chem. 1965;69(7): 2400-2401.

Lasne et al., Chemistry of beta(+)-emitting compounds based on fluorine-18. In: Contrast Agents II. 2002;222:201-58.

Lee et al., A fluoride-derived electrophilic late-stage fluorination reagent for PET imaging. Science. Nov. 4, 2011;334(6056):639-42. doi: 10.1126/science.1212625.

Li et al., Synthesis and local anesthetic activity of fluoro-substituted imipramine and its analogues. Bioorg Med Chem Lett. Jul. 1, 2007;17(13):3733-5. Epub Apr. 10, 2007.

Liang et al., Introduction of fluorine and fluorine-containing functional groups. Angew Chem Int Ed Engl. Aug. 5, 2013;52(32):8214-64. doi: 10.1002/anie.201206566. Epub Jul. 19, 2013.

Lin et al., Interactions of aziridines with nickel complexes: oxidative-addition and reductive-elimination reactions that break and make C—N. bonds. J Am Chem Soc. Mar. 27, 2002;124(12):2890-1.

Liu et al., Oxidative aliphatic C—H fluorination with fluoride ion catalyzed by a manganese porphyrin. Science. Sep. 14, 2012;337(6100):1322-5. doi: 10.1126/science.1222327.

Liu et al., Synthesis and properties of 12-fluororetinal and 12-fluororhodopsin. Model system for fluorine-19 NMR studies of visual pigments. J Am Chem Soc. 1981;103(24):7195-201.

Lovey et al., Fluorinated retinoic acids and their analogs. 3. Synthesis and biological activity of aromatic 6-fluoro analogs. J Med Chem. 1982;25(1):71-75.

Maas et al., Dication disulfides by reaction of thioureas and related compounds with trifluoromethanesulfonic anhydride. The role of triflic anhydride as an oxidizing agent. J Org Chem. 1981;46(8):1606-1610.

Maas et al., Dication ethers. 7. Dication ether salts from cyclic bisureas. J Heterocyclic Chemistry. 1985;22(3):907-10.

Mack et al., Effect of Chelate Ring Expansion on Jahn-Teller Distortion and Jahn-Teller Dynamics in Copper(II) Complexes. Inorg Chem. 2012;51(14):7851-7858.

Maeda et al., Amino Acids and Peptides. X.: Leu-Enkephalin Analogues Containing a Fluorinated Aromatic Amino Acid. Chem Pharm Bull. 1989;37(3):826-28.

Maimone et al., Evidence for in situ catalyst modification during the Pd-catalyzed conversion of aryl triflates to aryl fluorides. J Am Chem Soc. Nov. 16, 2011;133(45):18106-9. doi: 10.1021/ja208461k. Epub Oct. 21, 2011.

Makleit et al., Synthesis and chemical transformation of halogen-containing morphine derivatives. Magyar Kemikusok Lapja. 1997;52(6):282-89.

Marshall et al., Single-Crystal X-ray and Solution 13C NMR Study of Fluoro(p-nitrophenyl)bis(triphenylphosphine)palladium(II). Are There Effects of Through-Conjugation? Organometallics. 1998;17(24):5427-30.

Matthews et al., Equilibrium acidities of carbon acids. VI. Establishment of an absolute scale of acidities in dimethyl sulfoxide solution. J Am Chem Soc. 1975;97(24):7006-7014.

Mazzotti et al., Palladium(III)-Catalyzed Fluorination of Arylboronic Acid Derivatives. J Am Chem Soc. Sep. 25, 2013;135(38):14012-5. doi: 10.1021/ja405919z. Epub Sep. 16, 2013.

McCombie et al., The condensation of a-Keto-beta-anilino-alpha-phenylethane and its Homologues with Carbonyl Chloride, Phenylcarbimide, and Phenylthiocarbimide. J Chem Soc. 1913;103:56-63.

McGaraughty et al., Effects of A-317491, a novel and selective P2X3/P2X2/3 receptor antagonist, on neuropathic, inflammatory and chemogenic nociception following intrathecal and intraplantar administration. Br J Pharmacol. Dec. 2003;140(8):1381-8. Epub Nov. 17, 2003.

McMurtrey et al., Pd-catalyzed C—H fluorination with nucleophilic fluoride. Pd-catalyzed C—H fluorination with nucleophilic fluoride. Org Lett. Aug. 17, 2012;14(16):4094-7. doi: 10.1021/ol301739f. Epub Jul. 30, 2012.

Mendoza-Espinosa et al., Synthesis of 4- and 4,5-Functionalized Imidazol-2-ylidenes from a Single 4,5-Unsubstituted Imidazol-2-ylidene. J Am Chem Soc. 2010;132(21):7264-7265.

Miao et al., PET of EGFR Expression with an [18] F-Labeled Affibody Molecule. J Nucl Med. 2012;53:1110-1118 (10.2967/jnumed.111.100842).

Miller et al., Synthesis of 11C, 18F, 15O, and 13N radiolabels for positron emission tomography. Angew Chem Int Ed Engl. 2008;47(47):8998-9033. doi: 10.1002/anie.200800222.

Mirica et al., Structure and electronic properties of Pd(III) complexes. Coord Chem Rev. 2013;257(2):299-314.

(56) References Cited

OTHER PUBLICATIONS

Muller et al., Fluorine in pharmaceuticals: looking beyond intuition. Science. Sep. 28, 2007;317(5846):1881-6.

Muller et al., The rhodium(II)-catalyzed aziridination of olefins with {[(4-nitrophenyl)sulfonyl]imino}phenyl-lambda3-iodane. Canadian J of Chem. 1998;76(6):738-750.

Murphy et al., Organometallic Fluorides: Compounds Containing Carbonminus signMetalminus signFluorine Fragments of d-Block Metals. Chem Rev. Dec. 18, 1997;97(8):3425-3468.

Nagakura et al., Allodynia and hyperalgesia in adjuvant-induced arthritic rats: time course of progression and efficacy of analgesics. J Pharmacol Exp Ther. Aug. 2003;306(2):490-7. Epub May 1, 2003.

Noel et al., Accelerating palladium-catalyzed C—F bond formation: use of a microflow packed-bed reactor. Angew Chem Int Ed Engl. Sep. 12, 2011;50(38):8900-3. doi: 10.1002/anie.201104652. Epub Aug. 11, 2011.

Nyffeler et al., Selectfluor: Mechanistic Insight and Applications. Angew Chem Int Ed Engl. 2004;44(2):192-212.

Onishi et al., Palladium Polypyrazolylborate Complexes Containing a Pd—C Bond. Chem Lett. 1976:955-58.

Ortiz et al., A Convenient Synthesis of Methyl- and Isopropyl-Benzyl Ethers Using Silver(II) Oxide as Reagent. Synth Commun. 1993;23(6):749-56.

Park et al., Metabolism of fluorine-containing drugs. Annu Rev Pharmacol Toxicol. 2001;41:443-70.

Pawlikowski et al., Alkyl carbon-nitrogen reductive elimination from platinum(IV)sulfonamide complexes. J Am Chem Soc. Aug. 29, 2007;129(34):10382-93. Epub Aug. 2, 2007.

Pérez et al., Thermal Study of [Pd(2-Phpy)Cl(L)]Complexes (L=pyridines and amines). Journal of Thermal Analysis and Calorimetry. 2001;66(2):361-370.

Phelps, Positron emission tomography provides molecular imaging of biological processes. Proc Natl Acad Sci U S A. Aug. 1, 2000;97(16):9226-33.

Pidlypnyi et al., N-Heterocyclic carbenes from ylides of indolyl-imidazolium, azaindolylimidazolium, and indolyl-triazolium salts, and their borane adducts. Tetrahedron. 2014;70(45):8672-80.

Powers et al., Bimetallic palladium catalysis: direct observation of Pd(III)—Pd(III) intermediates. J Am Chem Soc. Dec. 2, 2009;131(47):17050-1. doi: 10.1021/ja906935c.

Powers et al., Bimetallic Pd(III) complexes in palladium-catalysed carbon—heteroatom bond formation. Nat Chem. Jul. 2009;1(4):302-9.

Powers et al., Bimetallic redox synergy in oxidative palladium catalysis. Acc Chem Res. Jun. 19, 2012;45(6):840-50. doi: 10.1021/ar2001974. Epub Oct. 27, 2011.

Powers et al., Bimetallic reductive elimination from dinuclear Pd(III) complexes. J Am Chem Soc. Oct. 13, 2010;132(40):14092-103. doi: 10.1021/ja1036644.

Powers et al., Connecting binuclear Pd(III) and mononuclear Pd(IV) chemistry by Pd—Pd bond cleavage. J Am Chem Soc. Jul. 25, 2012;134(29):12002-9. doi: 10.1021/ja304401u. Epub Jul. 17, 2012.

Powers et al., On the mechanism of palladium-catalyzed aromatic C—H oxidation. J Am Chem Soc. Oct. 20, 2010;132(41):14530-6. doi: 10.1021/ja1054274.

Powers et al., Palladium(III) in Synthesis and Catalysis. Top Organomet Chem. Jan. 1, 2011;503:129-156.

Privalov et al., Theoretical Studies of the Mechanism of Aerobic Alcohol Oxidation with Palladium Catalyst Systems. Organometallics.2005;24(5):885-893.

Purser et al., Fluorine in medicinal chemistry. Chem Soc Rev. Feb. 2008;37(2):320-30. doi: 10.1039/b610213c. Epub Dec. 13, 2007.

Reed et al., Intermolecular interactions from a natural bond orbital, donor-acceptor viewpoint. Chem Rev. 1988;88(6):899-926.

Roe et al., Structure and Solution Dynamics of [(Ph3P)2Pd(Ph)(FHF)]. Organometallics. 2000;19(22):4575-82.

Ryabov et al., Synthesis by ligand exchange, structural characterization, and aqueous chemistry of ortho-palladated oximes. Inorg Chem. 1992;31(14):3083-3090.

Sandford, Elemental fluorine in organic chemistry (1997-2006). J Fluorine Chem. 2007;128:90-104.

Sasaki et al., Solid phase synthesis and opioid receptor binding activities of [D-Ala2, D-Leu5]enkephalin analogs containing a fluorinated aromatic amino acid. Chem Pharm Bull (Tokyo). Nov. 1990;38(11):3162-3.

Serguchev et al., Transannular additions of selectfluor and xenon difluoride: regioselectivity and mechanism. J Phys Org Chem. 2011;24(5):407-13.

Sheldrick, A short history of SHELX. Acta Cryst Sect A. 2008;A64:112-122.

Singh et al., Recent highlights in electrophilic fluorination with 1-chloromethyl-4-fluoro-1,4-diazoniabicyclo[2.2.2]octane bis(tetrafluoroborate). Acc Chem Res. Jan. 2004;37(1):31-44.

Sladojevich et al., Late-stage deoxyfluorination of alcohols with PhenoFluor. J Am Chem Soc. Feb. 20, 2013;135(7):2470-3. doi: 10.1021/ja3125405. Epub Feb. 11, 2013.

Sladojevich et al., Condensed-phase, halogen-bonded CF3I and C2F5I adducts for perfluoroalkylation reactions. Angew Chem Int Ed Engl. Mar. 16, 2015;54(12):3712-6. doi: 10.1002/anie.201410954. Epub Feb. 4, 2015.

Sun et al., Room-temperature nucleophilic aromatic fluorination: experimental and theoretical studies. Angew Chem Int Ed Engl. Apr. 21, 2006;45(17):2720-5.

Tang et al., Deoxyfluorination of phenols. J Am Chem Soc. Aug. 3, 2011;133(30):11482-4. doi: 10.1021/ja2048072. Epub Jul. 12, 2011.

Tang et al., Silver-catalyzed late-stage fluorination. J Am Chem Soc. Sep. 1, 2010;132(34):121504. doi: 10.1021/ja105834t.

Tang et al., Silver-mediated fluorination of aryl silanes. Tetrahedron. Jun. 17, 2011;67(24):4449-4454.

Taylor et al., Catalytic asymmetric heterogeneous aziridination of styrene using CuHY: effect of nitrene donor on enantioselectivity. J Chem Soc Perkin Trans 2. 2001:1714-1723.

Teare et al., Synthesis and reactivity of [18F]-N-fluorobenzenesulfonimide. Chem Commun (Camb). Jun. 21, 2007;2007(23):2330-2.

Ting et al., Arylfluoroborates and alkylfluorosilicates as potential PET imaging agents: high-yielding aqueous biomolecular 18F-labeling. J Am Chem Soc. Sep. 28, 2005;127(38):13094-5.

Tius et al., The reaction of XeF2 with trialkylvinylstannanes: Scope and some mechanistic observations. Tetrahedron. 1995;51(14):3997-4010.

Tredwell et al., Electrophilic fluorination of organosilanes. Org Biomol Chem. Jan. 7, 2006;4(1):26-32. Epub Nov. 23, 2005.

Trofimenko, Boron-pyrazole chemistry. II. Poly(1-pyrazolyl)-borates. J Am Chem Soc. 1967;89(13):3170-3177.

Trofimenko, Polypyrazolylborates, a new class of ligands. Acc Chem Res. 1971;4(1):17-22.

Trofimenko, Recent advances in poly(pyrazolyl)borate (scorpionate) chemistry. Chem Rev. 1993;93(3):943-980.

Vasdev et al., On the preparation of fluorine-18 labelled XeF(2) and chemical exchange between fluoride ion and XeF(2). J Am Chem Soc. Oct. 30, 2002;124(43):12863-8.

Vicente et al., Synthesis of Tris- and Tetrakis(pyrazol-1-yl)borate Gold(III) Complexes. Crystal Structures of [Au{k2-N,N'-BH(Pz)3}C12](pz=Pyrazol-1-yl) and [Au{k2-N,N'-B(Pz)4}(k2—C,N—C6H4CH2NMe2-2)]C1O4.CHC13. Inorg Chem. 2002;41(7):1870-1875.

Wang et al., Versatile Pd(OTf)2 x 2 H2O—catalyzed ortho-fluorination using NMP as a promoter. J Am Chem Soc. Jun. 10, 2009;131(22):7520-1. doi: 10.1021/ja901352k.

Watson et al., Formation of ArF from LPdAr(F): catalytic conversion of aryl triflates to aryl fluorides. Science. Sep. 25, 2009;325(5948):1661-4. doi: 10.1126/science.1178239. Epub Aug. 13, 2009.

Williams et al., Main group metal halide complexes with sterically hindered thioureas. VIII. Complexes of lead(II) halides with 1,3-dimethyl-2(3H)-imidazolethione. Inorganica Chimica Acta. 1988;144(2):237-40.

(56) References Cited

OTHER PUBLICATIONS

Woo et al., Direct conversion of pyranose anomeric OH→F→R in the artemisinin family of antimalarial trioxanes. Tetrahedron Lett. 1998;39(12):1533-36.

Yahav et al., Synthesis of the Elusive (R3P)2MF2 (M=Pd, Pt) Complexes. J Am Chem Soc. 2003;125(45):13634-35.

Yahav-Levi et al., Competitive aryl-iodide vs aryl-aryl reductive elimination reactions in Pt(IV) complexes: experimental and theoretical studies. J Am Chem Soc. Jan. 16, 2008;130(2):724-31.

Yamada et al., Synthesis and Reaction of New Type I—N. Ylide, N-Tosyliminoiodinane. Chem Lett. 1975;4(4):361-62.

Yandulov et al., Aryl-fluoride reductive elimination from Pd(II): feasibility assessment from theory and experiment. J Am Chem Soc. Feb. 7, 2007;129(5):1342-58.

Ye et al., Mild copper-mediated fluorination of aryl stannanes and aryl trifluoroborates. J Am Chem Soc. Mar. 27, 2013;135(12):4648-51. doi: 10.1021/ja400300g. Epub Mar. 13, 2013.

Zhang et al., Interception of the radicals produced in electrophilic fluorination with radical traps (Tempo, Dmpo) studied by electrospray ionization mass spectrometry. Rapid Commun Mass Spectrom. 2006;20(12):1877-82.

Zhang et al., Investigation of radical cation in electrophilic fluorination by ESI-MS. Org Lett. Sep. 1, 2005;7(18):3877-80.

\* cited by examiner

US 9,273,083 B2

NICKEL FLUORINATING COMPLEXES AND USES THEREOF

RELATED APPLICATIONS

The present application is a national stage filing under 35 U.S.C. § 371 of international PCT application, PCT/US2013/061968, filed Sep. 26, 2013, which claims priority under 35 U.S.C. § 119(e) to U.S. provisional patent applications, U.S.S.N. 61/705,980, filed Sep. 26, 2012, and U.S.S.N. 61/782,119, filed Mar. 14, 2013, the entire contents of each of which are incorporated herein by reference.

GOVERNMENT SUPPORT

This invention was made with government support under EB013042 awarded by the National Institutes of Health. The government has certain rights in the invention.

BACKGROUND OF THE INVENTION

The regioselective fluorination of organic compounds is an important challenge in the synthesis of pharmaceuticals and agrochemicals (see, for example, Muller et al., *Science* 2007, 317, 1881-1886; Park et al., *Annual Review of Pharmacology and Toxicology* 2001, 41, 443-470; Bohm et al., *ChemBioChem* 2004, 5, 637-643; and Jeschke, *ChemBioChem.* 2004, 5, 570-589).

Syntheses of simple fluoroarenes currently rely on the pyrolysis of diazonium tetrafluoroborates (Balz, G.; Schiemann, G. *Ber. Deut. Chem. Ges.* 1927, 60, 1186-1190), direct fluorination using highly reactive, elemental fluorine (Sandford, J. *Fluorine Chem.* 2007, 128, 90-104), or nucleophilic aromatic substitution reactions of electron—poor aromatic systems by displacement of other halogens or nitro groups (Sun et al., *Angew. Chem., Int. Ed.* 2006, 45, 2720-2725; Adams et al., *Chem. Soc. Rev.* 1999, 28, 225-231). The reductive elimination of arylfluorides from palladium(II) fluoride complexes is an attractive potential alternative that has been investigated by Grushin (Grushin, *Chem.—Eur. J.* 2002, 8, 1006-1014) over the past decade and more recently by Yandulov. A single substrate—p—fluoronitrobenzene—has been prepared successfully in 10% yield in the Yandulov study from a stoichiometric palladium fluoride complex (Yandulov et al., *J. Am. Chem. Soc.* 2007, 129, 1342-1358) (See also Watson et al., *Science,* 2009, Vol. 325. No. 5948, pp. 1661-1664). Directed electrophilic fluorination of phenylpyridine derivatives and related structures using catalytic palladium(II) acetate and N-fluoropyridinium salts has been reported by Sanford in 2006 (Hull et al., *J. Am. Chem. Soc.* 2006, 128, 7134-7135). Taking advantage of the directing effect of a pyridine substituent, proximal carbon-hydrogen bonds can be fluorinated using microwave irradiation at high temperatures (100-150° C., 1-4 h, 33-75% yield).

The use of $^{18}$F-labelled organic compounds for positron-emission tomography (PET) requires the controlled, efficient introduction of fluorine into functionalized molecules (see, for example, Couturier et al., *Eur. J. Nucl. Med. Mol. Imaging* 2004, 31, 1182-1206; Lasne et al., "Chemistry of beta(+)-emitting compounds based on fluorine-18" *In Contrast Agents II,* 2002; Vol. 222, pp 201-258; and Phelps, *Proc. Natl. Acad. Sci. U.S.A.* 2000, 97, 9226-9233). PET has been used to measure presynaptic accumulation of $^{18}$F-fluorodopa tracer in the dopaminergic regions of the brain (see, for example, Ernst et al., "Presynaptic Dopaminergic Deficits in Lesch-Nyhan Disease" *New England Journal of Medicine* (1996) 334:1568-1572), but fluorination of other organic compounds has been difficult due to lack of an appropriate fluorination method.

Despite the utility of fluorinated organic compounds in multiple pharmaceutical, diagnostic, and agrochemical applications, C—F bond formation remains a challenging organic transformation with no broadly applicable solutions.

SUMMARY OF THE INVENTION

The present invention provides novel nickel complexes and methods of using these complexes in the fluorination of organic compounds. The inventive system is also particularly useful in preparing $^{18}$F-labeled compounds for PET imaging. The inventive system relies on utilizing a fluorine source (e.g., a nucleophilic fluorine source) such as a commercially available fluorinating reagent (e.g., tetrabutylammonium difluorophenylsilicate (TBAT)) or a fluoride source comprising water (e.g., containing $^{18}$F which can be produced using a cyclotron).

In one aspect, the present invention is directed to a method of producing a fluorinated organic compound, the method comprising mixing a nickel comprising complex with a flourine source under conditions sufficient to fluorinate the organic compound, thereby providing a fluorinated organic compound.

In some embodiments, the fluorine source is a fluoride source comprising water (e.g., a fluoride source in a mixture is water and acetonitrile). In some embodiments, the fluoride source contains $^{18}$F fluoride. In some embodiments, the fluoride source is produced using a cyclotron. In some embodiments, the fluoride source is produced using a cyclotron in $^{18}$O enriched water.

In some embodiments, the method further comprises an oxidant (e.g., when the fluorinating agent is nucleophilic). In some embodiments, the fluorinating agent is a nucleophilic fluorinating agent. In some embodiments, the nucleophilic fluorinating agent is sodium fluoride (NaF), silver fluoride (AgF), tetrabutylammonium fluoride ($NH_4F$), substituted tetrabutylammonium fluoride ($NR_4F$), cesium fluoride (CsF), potassium fluoride (KF), tetrabutylammonium difluorotriphenylsilicate (TBAT) and $XeF_2$. In some embodiments, the nucleophilic fluorinating agent comprises $^{18}$F or $^{19}$F.

In some embodiments, the method is carried out in the absence of an oxidant (e.g., when the fluorinating agent is electrophilic). In some embodiments, the fluorinating agent is an electrophilic fluorinating agent. In some embodiments, the fluorinating agent is selected from the group consisting of N-fluoropyridinium triflate, N-fluoro-2,4,6-trimethylpyridinium triflate, N-fluoro-2,4,6-trimethylpyridinium tetrafluoroborate, N-fluoro-2,6-dichloropyridinium tetrafluoroborate, N-fluoro-2,6-dichloropyridinium triflate, N-fluoropyridinium pyridine heptafluorodiborate, N-fluoropyridinium tetrafluoroborate, an N-fluoroarylsulfonimide (e.g., N-fluorobenzenesulfonimide), N-chloromethyl-N'-fluorotriethylenediammonium bis(tetrafluoroborate) (SELECTFLUOR®), N-chloromethyl-N'-fluorotriethylenediammonium bis(hexafluorophosphate) and N-chloromethyl-N'-fluorotriethylenediammonium bis(triflate). In some embodiments, the electrophilic fluorinating agent comprises $^{18}$F or $^{19}$F.

In some embodiments, the reaction further comprises a metal chelator. In some embodiments, the stabilizer is a crown ether (e.g., 18-crown-6).

In certain embodiments, the molar ratio of fluorinating agent to nickel comprising complex is 10:1 or lower (e.g., 9:1, 8:1, 7:1, 6:1, 5:1, 4:1, 3:1, 2.5:1, 2:1, 1.5:1 or 1:1). In certain embodiments, the molar ratio of oxidant to nickel comprising complex is 10:1 or lower (e.g., 9:1, 8:1, 7:1, 6:1, 5:1, 4:1, 3:1, 2.5:1, 2:1, 1.5:1 or 1:1).

In certain embodiments, the ratio of $^{18}$F-fluorine source to nickel comprising complex is 1:10 or lower (e.g., 1:11, 1:100, 1:1,000, 1:10,000, 1:100,000 or 1:1,000,000). In some embodiments, the ratio of $^{18}$F-fluorine source to nickel comprising complex is 1:10 or lower when the fluorine source is aqueous fluoride (e.g., an $^{18}$F enriched fluoride source). In some embodiments, the nickel comprising complex is a nickel complex of formula (I):

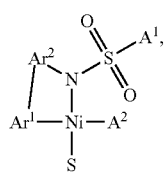

(I)

wherein:
- $Ar^1$ is aryl or heteroaryl substituted with n occurrences of $R^1$;
- $Ar^2$ is aryl or heteroaryl substituted with m occurrences of $R^2$;
- $A^1$ is $C_{1-6}$ alkyl, $C_{1-6}$ alkoxy, $C_{3-7}$ cycloalkyl, $C_{2-6}$ alkenyl, $C(O)$-$R^6$, $C(O)$—$R^6$, —$NH_2$, —$NHR^7$, —$N(R^7)_2$, $NO_2$, —OH, —$OR^6$, aryl, heteroaryl or heterocyclyl, wherein each alkyl, alkoxy, cycloalkyl, alkenyl, aryl, heteroaryl or heterocyclyl can be further substituted with o occurrences of $R^3$;
- $A^2$ is an N-heterocyclic carbene, phosphine, phosphate or heteroaryl substituted with p occurrences of $R^4$;
- S is a substrate wherein the substrate is linked through an aryl, heteroaryl or alkenyl moiety present in the substrate;
- each $R^1$, $R^2$, $R^3$ and $R^4$ is independently halo, $C_{1-6}$ alkyl, $C_{1-6}$ alkoxy, $C_{3-7}$ cycloalkyl, $C_{2-6}$ alkenyl, $C(O)$—$R^6$, $C(O)OR^6$, —$NH_2$, —$NHR^7$, —$N(R^7)_2$, $NO_2$, —OH, —$OR^6$, aryl, heteroaryl or heterocyclyl, wherein each alkyl, alkoxy, cycloalkyl, alkenyl, aryl, heteroaryl or heterocyclyl can be further substituted with 0-3 occurrences of $R^8$;
- $R^6$ is $C_{1-6}$ alkyl, $C_{1-6}$ alkenyl, $C_{3-7}$ cycloalkyl, —$C(O)O$—$C_{1-6}$ alkyl, aryl, heteroaryl or heterocyclyl;
- each $R^7$ is independently $C_{1-6}$ alkyl, $C_{1-6}$ alkenyl, $C_{3-7}$ cycloalkyl, —$C(O)$—$C_{1-6}$ alkyl, —$C(O)O$—$C_{1-6}$ alkyl, aryl, heteroaryl or heterocyclyl;
- each $R^8$ is independently halo, $C_{1-6}$ alkyl, $C_{1-6}$ alkoxy, $C_{1-6}$ alkenyl, $C_{3-7}$ cycloalkyl, $C_{1-6}$ alkyl-amine, —$C(O)$—$C_{1-6}$ alkyl, —$C(O)O$—$C_{1-6}$ alkyl, $C_{0-6}$ alkyl-$NHR^7$, aryl, aryloxy, aralkyl, heteroaryl, heteroaralkyl, heterocyclyl or heterocyclylalkyl or wherein two adjacent $R^8$ moieties, taken together with the atoms to which they are attached, form a $C_{3-7}$ cycloalkyl, aryl, heteroaryl or heterocyclyl group, wherein each alkyl, alkoxy, alkenyl, cycloalkyl, aryl; and
- m, n, o and p are each independently an integer from 0-5.

In some embodiments, $Ar^1$ is heteroaryl (e.g., an N-containing heteroaryl such as pyridine, pyrimidine, imidazole, 1,2,3-triazole or 1,2,4-triazole) substituted with n occurrences of $R^1$. In some embodiments, $Ar^2$ is heteroaryl (e.g., an N-containing heteroaryl such as quinoline or isoquinoline). In some embodiments, $Ar^2$ is aryl (e.g., phenyl) substituted with m occurrences of $R^2$.

In some embodiments, the nickel complex of formula (I) is a complex of formula (II):

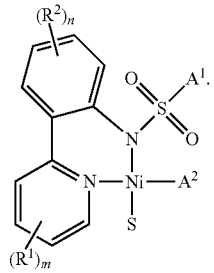

(II)

In some embodiments, $A^1$ is $C_{1-6}$ alkyl, $C_{3-6}$ alkoxy, $C_{3-7}$ cycloalkyl, $C_{2-6}$ alkenyl, aryl, heteroaryl or heterocyclyl can be further substituted with o occurrences of $R^3$. In some embodiments, $A^1$ is aryl (e.g., phenyl) substituted with o occurrences of $R^3$.

In some embodiments, the nickel complex of formula (I) or (II) is a complex of formula (III):

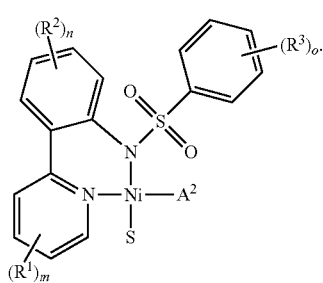

(III)

In some embodiments, $A^2$ is heteroaryl (e.g., an N-containing heteroaryl such as pyridine, pyrimidine, imidazole, 1,2,3-triazole or 1,2,4-triazole) substituted with p occurrences of $R^4$.

In some embodiments, the nickel complex of formula (I), (II) or (III) is a complex of formula (IV):

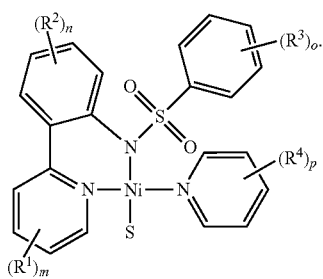

(IV)

In some embodiments, m is 0. In some embodiments, n is 0. In some embodiments, p is 0. In some embodiments, o is 1. In some embodiments, $R^3$ is —$NO_2$. In some embodiments, $R^3$ is substituted at the ortho position relative to the sulfonyl moiety.

In some embodiments, the nickel complex of formula (I), (II), (III) or (IV) is a complex of formula (V):

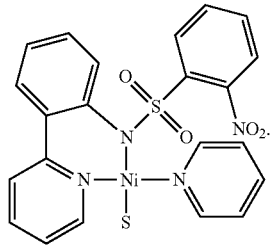
(V)

In some embodiments, S is a pharmaceutically active compound (e.g., a biologically active compound) comprising an aryl, heteroaryl or alkenyl moiety. In some embodiments, S is a natural product comprising an aryl, heteroaryl or alkenyl moiety.

In some embodiments, S is an optionally substituted aryl comprising substrate (e.g., phenyl). In some embodiments, S is an unsubstituted aryl comprising substrate (e.g., unsubstituted phenyl). In some embodiments, S is a substituted aryl (e.g., a phenyl substituted by one or more substituents). In some embodiments, S is an optionally substituted heteoaryl (e.g., an optionally substituted indolyl or benzoxazolyl). In some embodiments, S is an optionally substituted $C_{2-6}$ alkenyl (e.g., a $C_{2-6}$ alkenyl substituted with one or more substituents). In some embodiments, S is selected from one of the following:

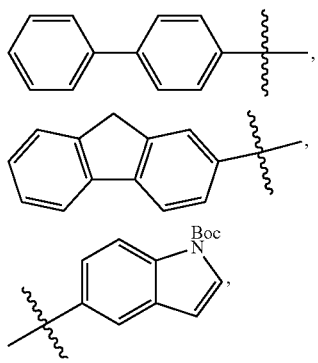

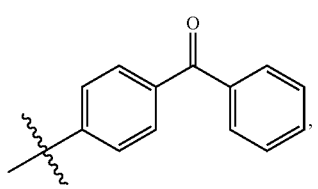

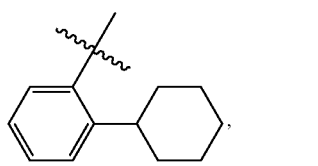

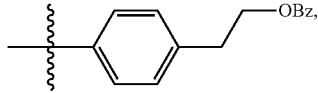

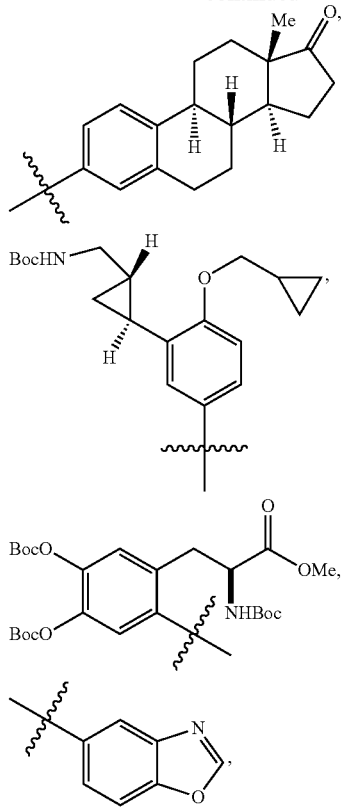

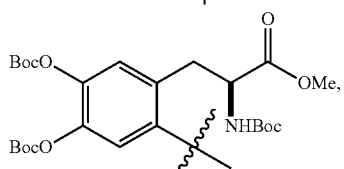

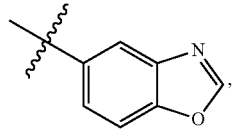

or

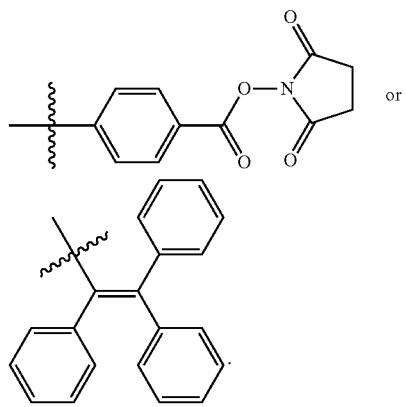

In some embodiments, the complex of formula (I), (II), (III), (IV) or (V) is selected from the following:

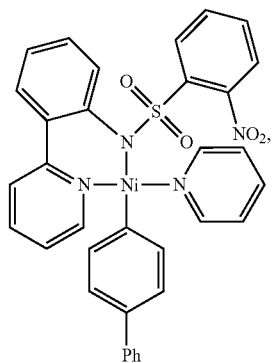

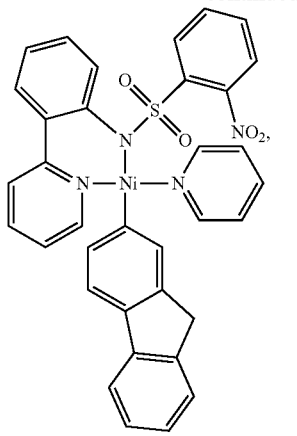
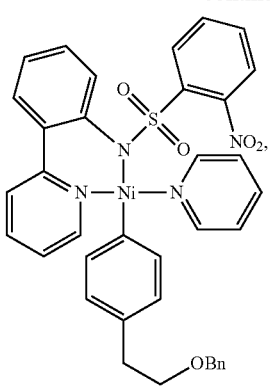
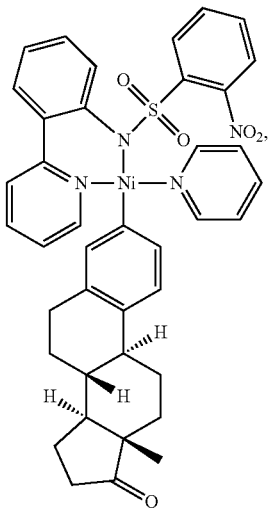
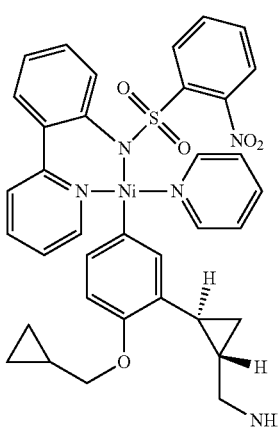
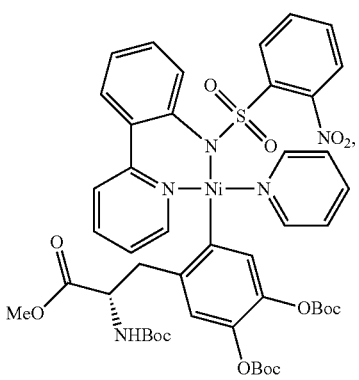

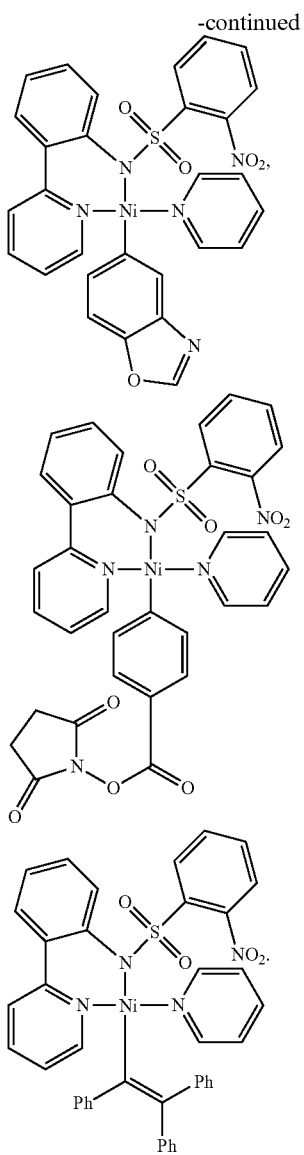

In some embodiments, the oxidant is a compound of formula (IX):

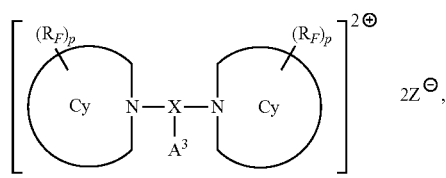

wherein
X is a halogen
$A^3$ is an aryl or heteroaryl group;
Cy taken together with the nitrogen atom to which it is attached forms a heterocyclyl or heteroaryl ring;
each occurrence of $R_F$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —OR"; —C(=O)R"; —CO$_2$R"; —CN; —SCN; —SR"; —SOR"; —SO$_2$R"; —NO$_2$; —N(R")$_2$; —NHC(O)R"; or —C(R")$_3$; wherein each occurrence of R" is independently a hydrogen, a protecting group, an aliphatic moiety, a heteroaliphatic moiety, an aryl moiety; a heteroaryl moiety; alkoxy; aryloxy; alkylthio; arylthio; amino, alkylamino, dialkylamino, heteroaryloxy; or heteroarylthio moiety; and
Z is an anion.

In some embodiments, X is iodine.

In some embodiments, Cy is pyridinyl.

In some embodiments, $R_C$ is hydrogen.

In some embodiments, p is 0. In some embodiments, p is 1. In some embodiments, p is 2.

In some embodiments, $A^3$ is an aryl group (e.g., phenyl).

In some embodiments, each $R_F$ is independently unsubstituted alkyl (e.g., methyl). In some embodiments, each $R_F$ is independently —CN. In some embodiments, each $R_F$ is independently —OR" wherein R" is an aliphatic moiety (e.g., methyl). In some embodiments, each $R_F$ is independently —N(R")$_2$ wherein R" is an aliphatic moiety (e.g., methyl).

In some embodiments, Z is trifluoromethanesulfonate.

In some embodiments, the compound of formula (IX) is selected from the following:

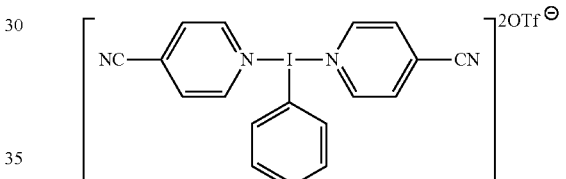

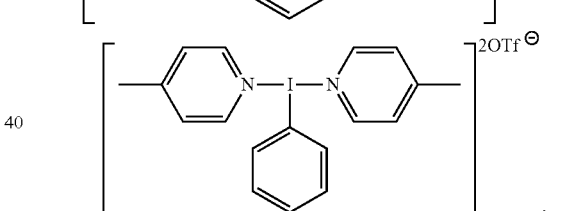

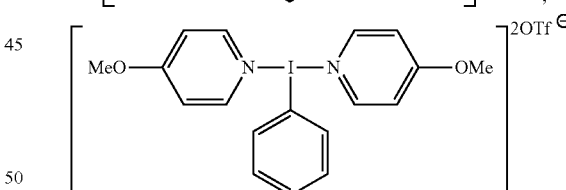

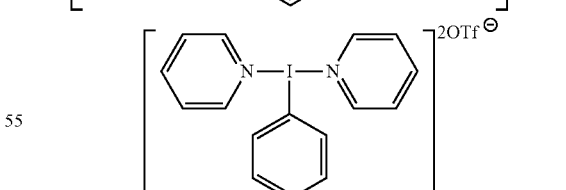

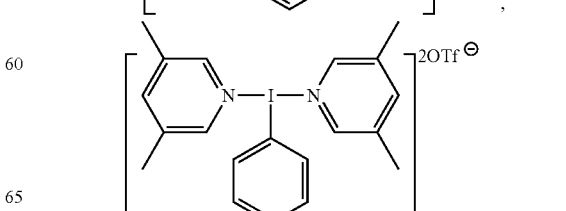

, or

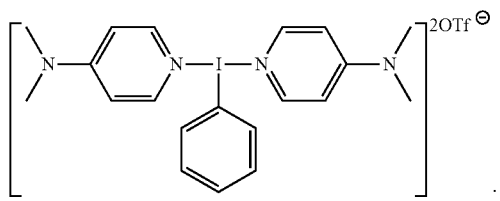
In some embodiments, the fluorinated organic compound comprises an aryl group. In some embodiments, the fluorinated organic compound comprises a heteroaryl group. In some embodiments the fluorinated organic compound comprises an alkenyl group.
In some embodiments, the fluorinated organic compound is selected from the following:
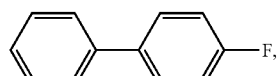
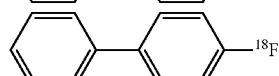
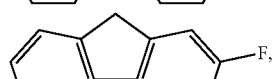
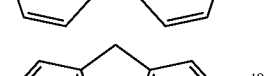
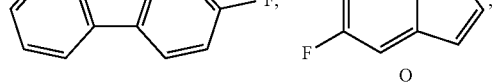
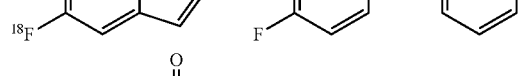
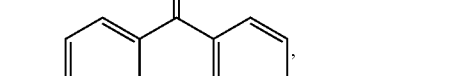
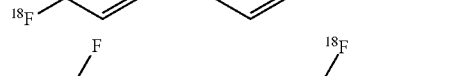
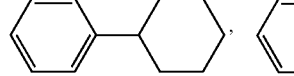
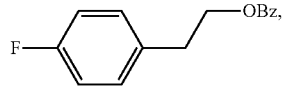
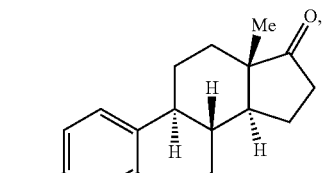
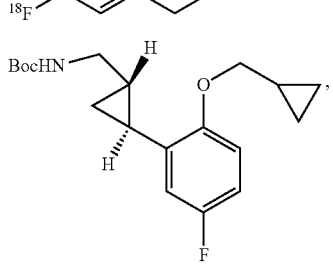
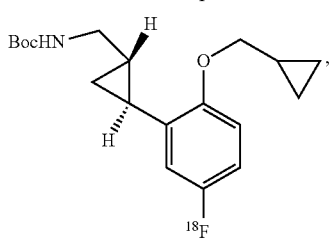
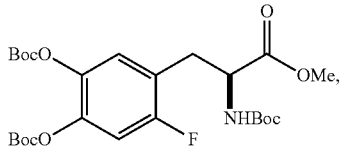
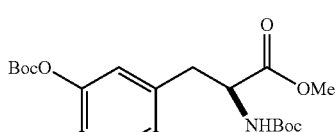
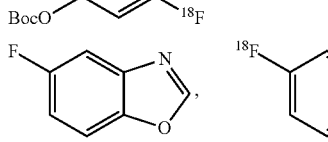
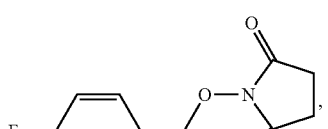
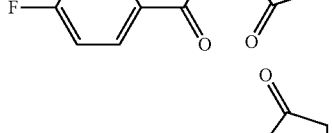
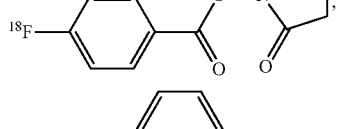
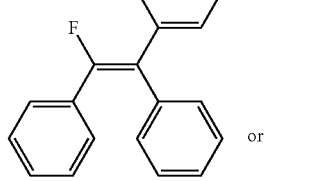
or -continued

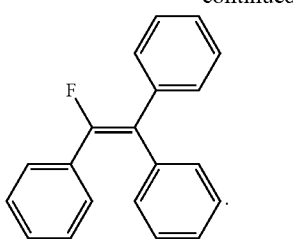

In some embodiments, the fluorinated organic compound is selected from the following:

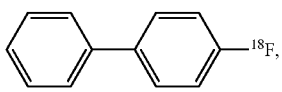

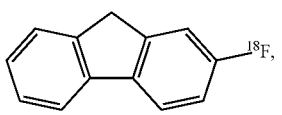

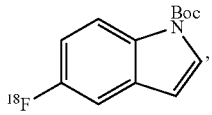

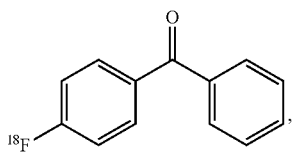

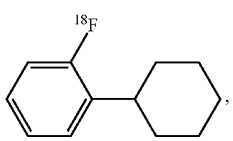

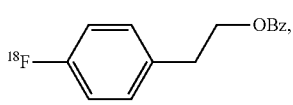

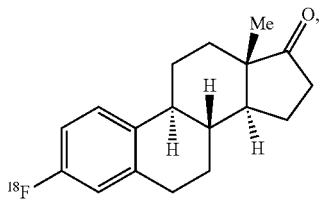

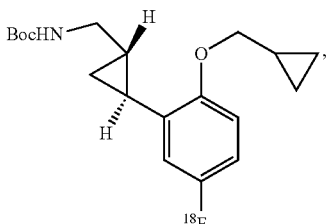

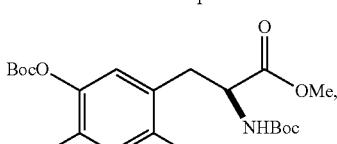

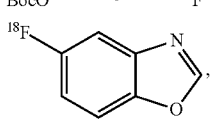

-continued

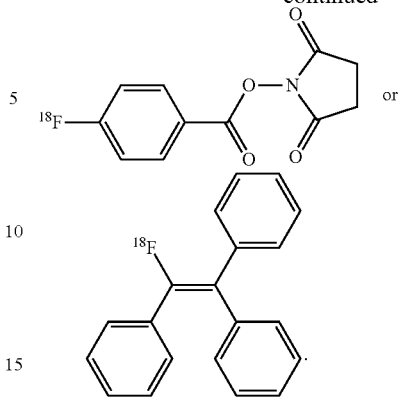

In some embodiments, the method further comprises a solvent. In some embodiments, the solvent is a polar aprotic solvent. In some embodiments, the solvent is acetonitrile.

In some embodiments, the method further comprises adding a salt to the source of fluorine. In some embodiments, the method further comprises adding a salt to the nickel comprising complex. In some embodiments, the method further comprises including a salt in the mixture containing the nickel comprising complex and source of fluorine.

In some embodiments, the salt comprises a chloride, perchlorate, nitrate, phosphate, or sulfate. In some aspects of these embodiments, the phosphate comprises a monobasic, dibasic, or tribasic phosphate (e.g., $(H_2PO_4)^-$, $(HPO_4)^{2-}$, $(PO_4)^{3-}$). In some aspects of these embodiments, the phosphate comprises a tribasic phosphate (e.g., $(PO_4)^{3-}$). In some embodiments, the salt comprises a sodium, potassium, or cesium. In some embodiments, the salt is selected from the following group: NaCl, $KClO_4$, $KNO_3$, $K_3PO_4$, $Na_2HPO_3$, or $Na_2SO_4$. In some embodiments, the salt comprises $K_3PO_4$ or $Na_2HPO_3$. In some embodiments, the salt comprises $K_3PO_4$.

In some embodiments, the method comprises an inert atmosphere. In some embodiments, the method is carried out under anhydrous conditions. In some embodiments, the method comprises cooling (e.g., to 0 ° C. or lower).

In some embodiments, the method comprises a source of energy. In some embodiments, the method comprises heat.

In some embodiments, the fluorinated organic compound is an MRI imaging agent. In some embodiments, the fluorinated organic compound is a PET imaging agent. In some embodiments, the fluorinated organic compound is used as a probe (e.g., a biological NMR probe). In some embodiments, the fluorinated organic compound is a pharmaceutically acceptable compound.

In another aspect, the present invention is directed to a method of fluorinating an organic compound, the method comprising mixing a nickel comprising complex with a fluoride source comprising water and an oxidant under conditions sufficient to fluorinate the organic compound, thereby providing a fluorinated organic compound.

In some embodiments, the fluorinated organic compound comprises an $^{18}$F labeled organic compound. In some embodiments, the fluoride source comprising water is a fluoride source in a mixture of water and acetonitrile.

In some embodiments, the salt comprises a chloride, perchlorate, nitrate, phosphate, or sulfate. In some aspects of these embodiments, the phosphate comprises a monobasic, dibasic, or tribasic phosphate (e.g., $(H_2PO_4)^-$, $(HPO_4)^{2-}$, $(PO_4)^{3-}$). In some aspects of these embodiments, the phosphate comprises a tribasic phosphate (e.g., $(PO_4)^{3-}$). In some embodiments, the salt comprises a sodium, potassium, or cesium. In some embodiments, the salt is selected from the following group: NaCl, $KClO_4$, $KNO_3$, $K_3PO_4$, $Na_2HPO_3$, or $Na_2SO_4$.

In some embodiments, the salt comprises $K_3PO_4$ or $Na_2HPO_3$. In some embodiments, the salt comprises $K_3PO_4$.

In another aspect, the present invention is directed to a method of making a nickel complex of formula (I), the method comprising treating an organic compound of formula (VI):

(VI), with tetramethylethylenediamine and bis(1,5-cyclooctadiene)nickel to provide a nickel complex of formula (VII):

(VII)

the method further comprising, treating a nickel complex of formula (VII) with a silver compound of formula (VIII) and $A^2$:

(VIII)

to provide a nickel complex of formula (I), wherein
$X^1$ is a leaving group; and
$Ar^1$, $Ar^2$, $A^1$, $A^2$, $A^3$, $R^1$, $R^2$, $R^3$, $R^4$, $R^6$, $R^7$, $R^8$, m, n, o and p are as defined for formula (I).

In some embodiments, $X^1$ is halo (e.g., bromo). In some embodiments, $X^1$ is —OTf.

In certain embodiments, the ratio of a compound of formula (VI) to tetramethylethylenediamine is 10:1 or lower (e.g., 9:1, 8:1, 7:1, 6:1, 5:1, 4:1, 3:1, 2.5:1, 2:1, 1.5:1 or 1:1). In some embodiments, the ratio of a compound of formula (VI) to bis(1,5-cyclooctadiene)nickel is 10:1 or lower (e.g., 9:1, 8:1, 7:1, 6:1, 5:1, 4:1, 3:1, 2.5:1, 2:1, 1.5:1 or 1:1). In certain embodiments, the ratio of a compound of formula (VII) to a compound of formula (VIII) is 10:1 or lower (e.g., 9:1, 8:1, 7:1, 6:1, 5:1, 4:1, 3:1, 2.5:1, 2:1, 1.5:1 or 1:1).

In another aspect, the present invention is directed to methods of making a nickel complex of formula (I), the method comprising treating an organic compound of formula (X):

(X), with a nickel cubane complex of Formula (XI):

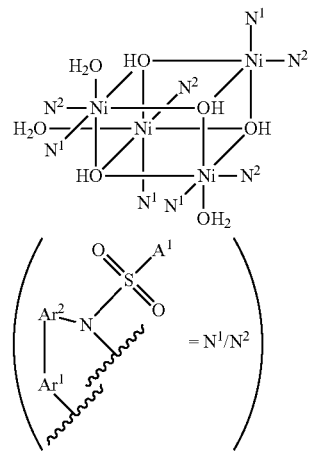

(XI)

to provide an organic nickel complex of formula (I), wherein:
$R^9$ is defined as halo, $C_{1-6}$ alkyl, $C_{1-6}$ alkoxy, $C_{3-7}$ cycloalkyl, $C_{2-6}$ alkenyl, $C(O)$—$R^6$, $C(O)OR^6$, —$NH_2$, —$NHR^7$, —$N(R^7)_2$, —OH, —$OR^6$, aryl, heteroaryl, or heterocyclyl, wherein each alkyl, alkoxy, cycloalkyl, alkenyl, aryl, heteroaryl, or heterocyclyl can be further substituted with 0-3 occurrences of $R^8$; and
$Ar^1$, $Ar^2$, $A^1$, $A^2$, $A^3$, $R^1$, $R^2$, $R^3$, $R^4$, $R^6$, $R^7$, $R^8$, m, n, o and p are as defined for formula (I).

In some embodiments, $R^9$ is —OH. In some embodiments, $R^9$ is —OH. In some embodiments, $R^9$ is methoxy. In some embodiments, $R^9$ is ethoxy. In some embodiments, $R^9$ is isopropoxy. In some embodiments, two $R^9$ groups are taken together as a pinacol. In some embodiments, two $R^9$ groups are taken together as catechol.

In some embodiments, the nickel complex of formula (XI) is a complex of formula (XII):

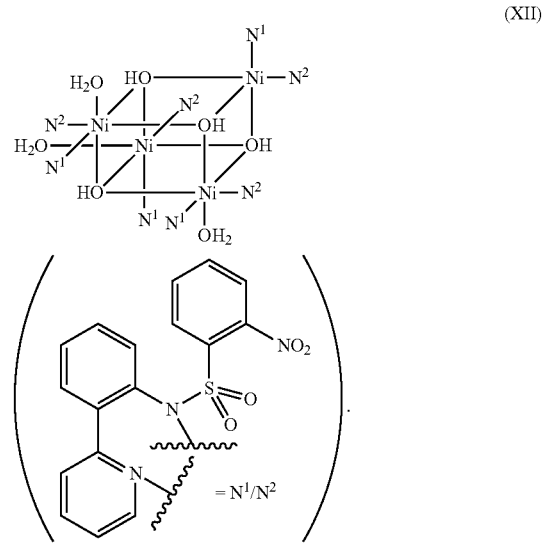

(XII)

In another aspect, the present invention is directed to a method of making a nickel complex of formula (I), the method comprising treating an organic compound of formula (XIII):

(XIII), with a nickel cubane complex of Formula (XI):

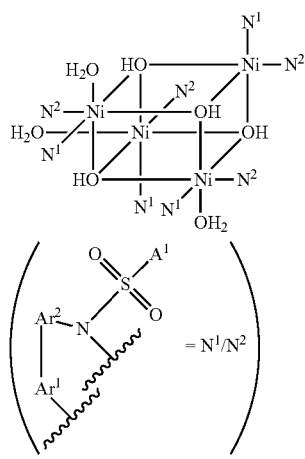

to provide an organic nickel complex of formula (I), wherein:
$X^1$ is a leaving group;
$M^1$ is an alkali metal; and
$Ar^1, Ar^2, A^1, A^2, A^3, R^1, R^2, R^3, R^4, R^6, R^7, R^8$, m, n, o and p are as defined for formula (I).

In some embodiments, $X^1$ is —F. In some embodiments, $X^1$ is —Cl. In some embodiments, $X^1$ is —Br. In some embodiments, $X^1$ is —I. In some embodiments, $X^1$ is —OTf. In some embodiments, $X^1$ is —OTs. In some embodiments, $X^1$ is —OH.

In some embodiments, $M^1$ is sodium. In some embodiments, $M^1$ is potassium.

In some embodiments, the nickel complex of formula (XI) is a complex of formula (XII):

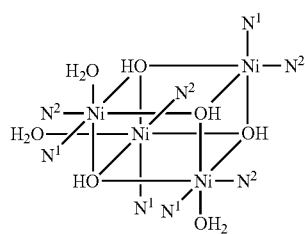

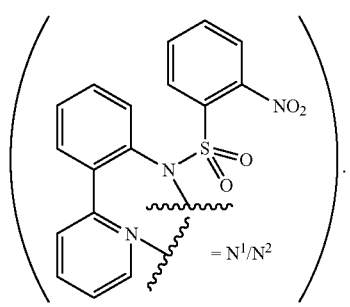

In another aspect, the present invention is directed to a nickel complex of formula (I):

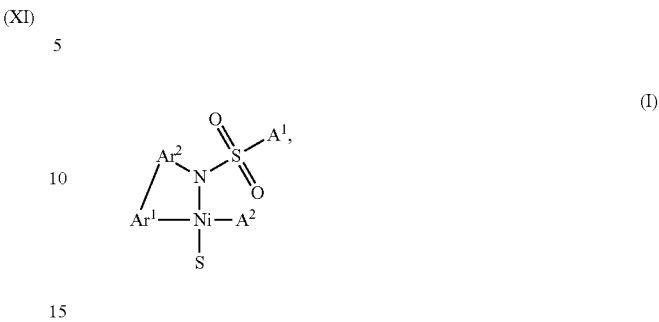

wherein:
$Ar^1$ is aryl or heteroaryl substituted with n occurrences of $R^1$;
$Ar^2$ is aryl or heteroaryl substituted with m occurrences of $R^2$;
$A^1$ is $C_{1-6}$ alkyl, $C_{1-6}$ alkoxy, $C_{3-7}$ cycloalkyl, $C_{2-6}$ alkenyl, C(O)—$R^6$, C(O)O$R^6$, —NH$_2$, —NH$R^7$, —N($R^7$)$_2$, NO$_2$, —OH, —O$R^6$, aryl, heteroaryl or heterocyclyl, wherein each alkyl, alkoxy, cycloalkyl, alkenyl, aryl, heteroaryl or heterocyclyl can be further substituted with o occurrences of $R^3$;
$A^2$ is an N-heterocyclic carbene, phosphine, phosphate or heteroaryl substituted with p occurrences of $R^4$;
S is a substrate wherein the substrate is linked through an aryl, heteroaryl or alkenyl moiety present in the substrate;
each $R^1$, $R^2$, $R^3$ and $R^4$ is independently halo, $C_{1-6}$ alkyl, $C_{i-6}$ alkoxy, $C_{3-7}$ cycloalkyl, $C_{2-6}$ alkenyl, C(O)—$R^6$, C(O)O$R^6$, —NH$_2$, —NH$R^7$, —N($R^7$)$_2$, NO$_2$, —OH, —O$R^6$, aryl, heteroaryl or heterocyclyl, wherein each alkyl, alkoxy, cycloalkyl, alkenyl, aryl, heteroaryl or heterocyclyl can be further substituted with 0-3 occurrences of $R^8$;
$R^6$ is $C_{1-6}$ alkyl, $C_{1-6}$ alkenyl, $C_{3-7}$ cycloalkyl, —C(O)O—$C_{1-6}$ alkyl, aryl, heteroaryl or heterocyclyl;
each $R^7$ is independently $C_{1-6}$ alkyl, $C_{1-6}$ alkenyl, $C_{3-7}$ cycloalkyl, —C(O)—$C_{1-6}$ alkyl, —C(O)O—$C_{1-6}$ alkyl, aryl, heteroaryl or heterocyclyl;
each $R^8$ is independently halo, $C_{1-6}$ alkyl, $C_{1-6}$ alkoxy, $C_{1-6}$ alkenyl, $C_{3-7}$ cycloalkyl, $C_{1-6}$ alkyl-amine, —C(O)—$C_{1-6}$ alkyl, —C(O)O—$C_{1-6}$ alkyl, $C_{0-6}$ alkyl-NH$R^7$, aryl, aryloxy, aralkyl, heteroaryl, heteroaralkyl, heterocyclyl or heterocyclylalkyl or wherein two adjacent $R^8$ moieties, taken together with the atoms to which they are attached, form a $C_{3-7}$ cycloalkyl, aryl, heteroaryl or heterocyclyl group, wherein each alkyl, alkoxy, alkenyl, cycloalkyl, aryl; and
m, n, o and p are each independently an integer from 0-5.

In some embodiments, $Ar^1$ is heteroaryl (e.g., an N-containing heteroaryl such as pyridine, pyrimidine, imidazole, 1,2,3-triazole or 1,2,4-triazole) substituted with n occurrences of $R^1$. In some embodiments, $Ar^2$ is heteroaryl (e.g., a N-containing heteroaryl such as quinoline or isoquinoline). In some embodiments, $Ar^2$ is aryl (e.g., phenyl) substituted with m occurrences of $R^2$.

In some embodiments, the nickel complex of formula (I) is a complex of formula (II):

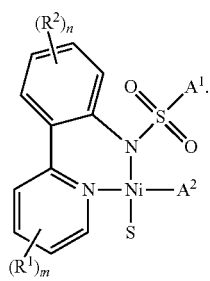
(II)

In some embodiments, $A^1$ is $C_{1-6}$ alkyl, $C_{1-6}$ alkoxy, $C_{3-7}$ cycloalkyl, $C_{2-6}$ alkenyl, aryl, heteroaryl or heterocyclyl can be further substituted with o occurrences of $R^3$. In some embodiments, $A^1$ is aryl (e.g., phenyl) substituted with o occurrences of $R^3$.

In some embodiments, the nickel complex of formula (I) or (II) is a complex of formula (III):

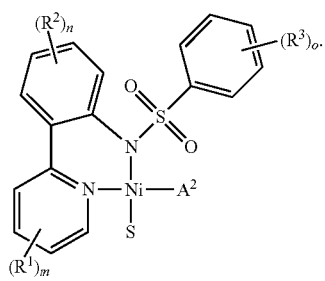
(III)

In some embodiments, $A^2$ is heteroaryl (e.g., an N-containing heteroaryl such as pyridine, pyrimidine, imidazole, 1,2,3-triazole or 1,2,4-triazole) substituted with p occurrences of $R^4$.

In some embodiments, the nickel complex of formula (I), (II) or (III) is a complex of formula (IV):

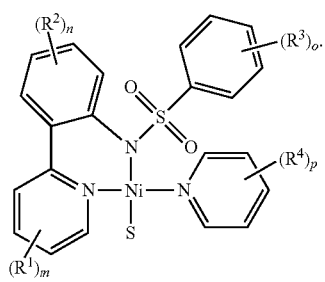
(IV)

In some embodiments, m is 0. In some embodiments, n is 0. In some embodiments, p is 0. In some embodiments, o is 1. In some embodiments, $R^3$ is —$NO_2$. In some embodiments, $R^3$ is substituted at the ortho position relative to the sulfonyl moiety.

In some embodiments, the nickel complex of formula (I), (II), (III) or (IV) is a complex of formula (V):

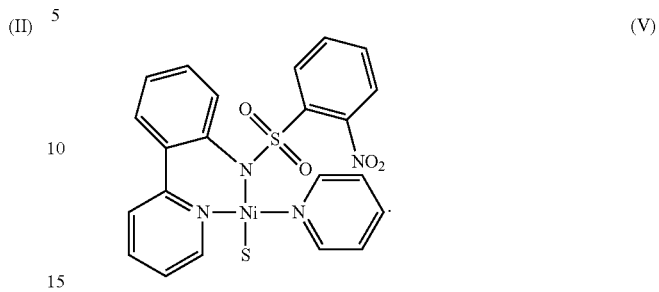
(V)

In some embodiments, S is an optionally substituted aryl comprising substrate (e.g., phenyl). In some embodiments, S is an unsubstituted aryl comprising substrate (e.g., unsubstituted phenyl). In some embodiments, S is a substituted aryl (e.g., a phenyl substituted by one or more substituents). In some embodiments, S is an optionally substituted heteoaryl (e.g., an optionally substituted indolyl or benzyoxazolyl). In some embodiments, S is an optionally substituted $C_{2-6}$ alkenyl (e.g., a $C_{2-6}$ alkenyl substituted with one or more substituents). In some embodiments, S is selected from one of the following:

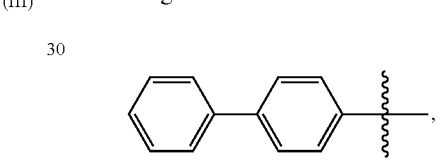

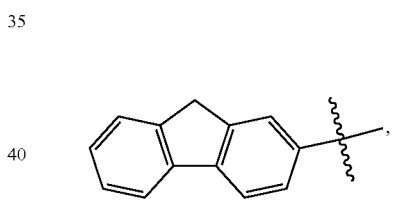

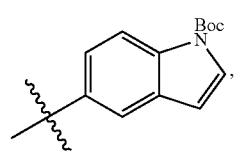

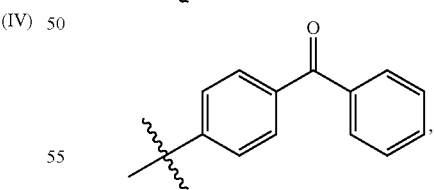

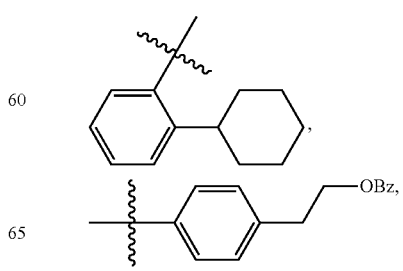

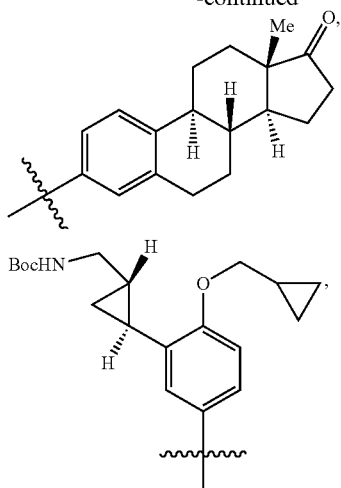
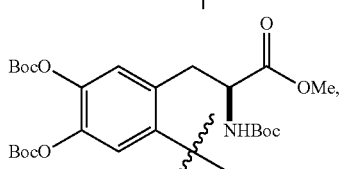
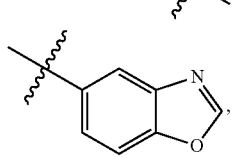
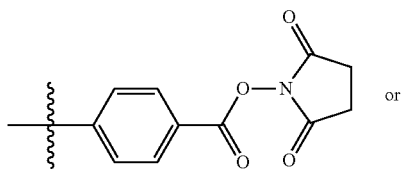
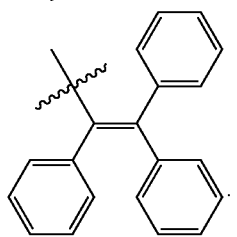
or
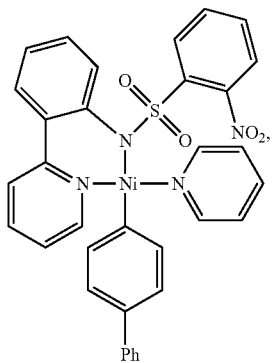
In some embodiments, the complex of formula (I), (II), (III), (IV) or (V) is selected from the following:
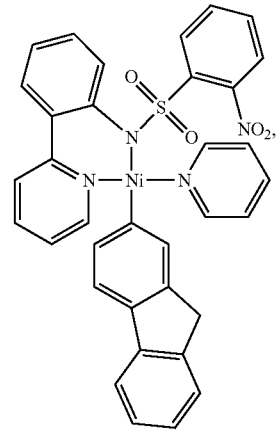
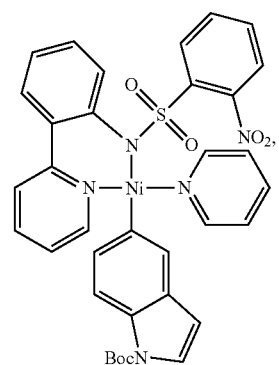
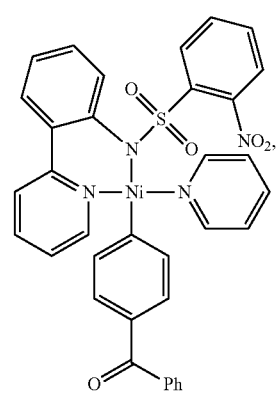
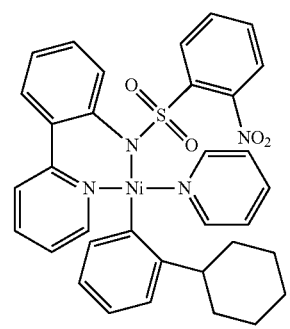

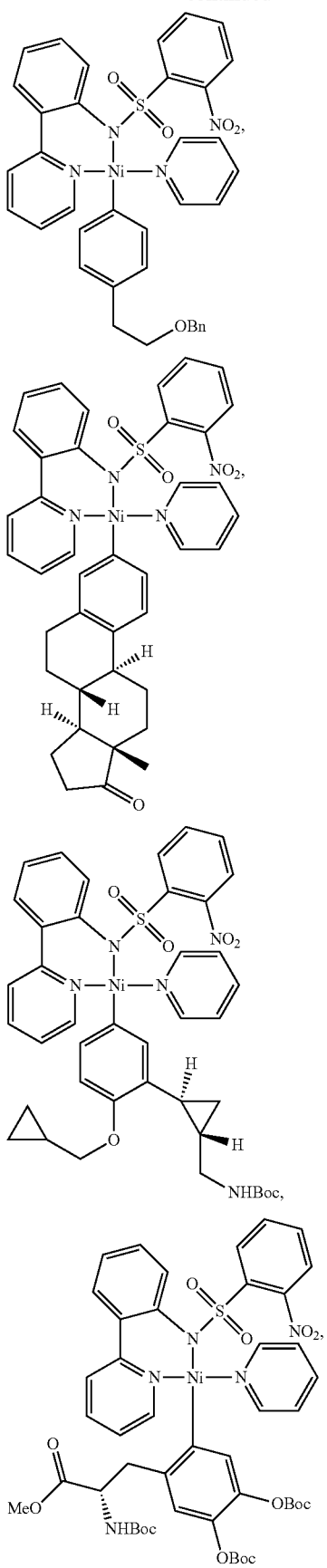

In another aspect, the present invention is directed to a method of storing a nickel complex described herein (e.g., a nickel complex of formula (I), (II), (III), (IV) or (V)), the method comprising maintaining the nickel complex in a sealed container for at least 12 hours.

In some embodiments, the sealed container is a vial. In some embodiments, the sealed container is an ampule.

In some embodiments, the sealed container is substantially free of dioxygen. In some embodiments, the sealed container contains an inert gas.

In another aspect, the present invention is directed to a composition comprising a nickel complex described herein (e.g., a nickel complex of formula (I), (II), (III), (IV) or (V)).

In some embodiments, the composition further comprises a solvent. In some embodiments, the solvent is a polar aprotic solvent. In some embodiments, the solvent is acetonitrile In another aspect, the present invention is directed to a reaction mixture comprising a nickel complex described herein (e.g., a nickel complex of formula (I), (II), (III), (IV) or (V)).

In some embodiments, the reaction mixture further comprises an oxidant.

In some embodiments, the reaction mixture further comprises a solvent. In some embodiments, the solvent is a polar aprotic solvent. In some embodiments, the solvent is acetonitrile.

In some embodiments, the reaction mixture further comprises an inert atmosphere.

In another aspect, the present invention is directed to a kit comprising a nickel complex described herein (e.g., a nickel complex of formula (I), (II), (III), (IV) or (V)) and a container. In some embodiments, the container is a vial. In some embodiments, the container is a sealed ampule.

In some embodiments, the container is substantially free of dioxygen. In some embodiments, the container contains an inert gas. In some embodiments, the kit further comprises instructions for use of the nickel complex.

In some embodiments, the kit further comprises an oxidant (e.g., an oxidant described herein). In some embodiments, the kit further comprises a metal chelator (e.g., a metal chelator described herein such as 18-crown-6).

This application refers to various issued patents, published patent applications, journal articles, and other publications, all of which are incorporated herein by reference.

Definitions

Definitions of specific functional groups and chemical terms are described in more detail below. For purposes of this invention, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, $5^{th}$ Edition, John Wiley & Sons, Inc., New York, 2001; Larock, Comprehensive Organic Transformations, VCH Publishers, Inc., New York, 1989; Carruthers, Some Modern Methods of Organic Synthesis, $3^{rd}$ Edition, Cambridge University Press, Cambridge, 1987; the entire contents of each of which are incorporated herein by reference.

Certain compounds of the present invention can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., Enantiomers, Racemates and Resolutions (Wiley Interscience, New York, 1981); Wilen et al., Tetrahedron 33:2725 (1977); Eliel, Stereochemistry of Carbon Compounds (McGraw-Hill, NY, 1962); Wilen, Tables of Resolving Agents and Optical Resolutions p. 268 (E.L. Eliel, Ed., Univ. of Notre Dame Press, Notre Dame, Ind. 1972).

As used herein, a "bond" refers to a single bond.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-10 carbon atoms. In certain embodiments, aliphatic groups contain 1-8 carbon atoms, 1-7 carbon atoms, 1-6 carbon atoms, 1-5 carbon atoms, 1-4 carbon atoms, 1-3 carbon atoms, or 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more double or triple bonds.

The term "alkyl," as used herein, refers to saturated, straight—or branched—chain hydrocarbon radicals derived from an aliphatic moiety containing between one and six carbon atoms by removal of a single hydrogen atom. In certain embodiments, the alkyl group employed in the invention contains 1-10 carbon atoms. In certain embodiments, the alkyl group employed contains 1-8 carbon atoms, 1-7 carbon atoms, 1-6 carbon atoms, 1-5 carbon atoms, 1-4 carbon atoms, 1-3 carbon atoms, or 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a Straight—or branched—chain aliphatic moiety having at least one carbon—carbon double bond by the removal of a single hydrogen atom. In certain embodiments, the alkenyl group employed in the invention contains 2-10 carbon atoms. In certain embodiments, the alkenyl group employed in the invention contains 2-8 carbon atoms, 2-7 carbon atoms, 2-6 carbon atoms, 2-5 carbon atoms, 2-4 carbon atoms, 2-3 carbon atoms or 2 carbon atoms. Alkenyl groups include, for example, ethenyl, propenyl, butenyl, 1-methyl-2-buten-1-yl, and the like.

The term "aryl" refers to monocyclic, bicyclic or tricyclic aromatic ring system having a total of five to 14 ring members, wherein at least one ring in the system is aromatic and wherein each ring in the system contains three to seven ring members. The term "aryl" may be used interchangeably with the term "aryl ring". In certain embodiments of the present invention, "aryl" refers to a monocyclic or polycyclic aromatic ring system which includes, but is not limited to, phenyl, biphenyl, naphthyl, anthracyl, phenanthrenyl, phenalenyl, and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenantriidinyl, or tetrahydronaphthyl, and the like.

The term "heteroaryl" refers to a monocyclic, bicyclic or tricyclic aromatic ring system having 5 to 14 ring atoms, wherein the ring atoms include carbon atoms and from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar—", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-$b$]-1,4-oxazin-3(4H)-one. A heteroaryl group may be mono- or bicyclic. The term "heteroaryl" may be used interchangeably with the terms "heteroaryl ring" any of which terms include rings that are optionally substituted.

As used herein, the terms "heterocyclyl" and "heterocyclic ring" are used interchangeably and refer to a monocyclic, bicyclic or tricyclic nonaromatic ring sytem that is either saturated or partially unsaturated, and having, in addition to carbon atoms, one to five heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", and "heterocyclyl ring", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono—or bicyclic.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined. As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}$R'; —$(CH_2)_{0-4}$OR'; —O—$(CH_2)_{0-4}$C(O)OR'; —$(CH_2)_{0-4}$CH(OR')$_2$; —$(CH_2)_{0-4}$SR'; —$(CH_2)_{0-4}$Ph, which may be substituted with R'; —$(CH_2)_{0-4}$O$(CH_2)_{0-1}$Ph which may be substituted with R'; —CH=CHPh, which may be substituted with R'; —NO$_2$; —CN; —N$_3$; —$(CH_2)_{0-4}$N(R')$_2$; —$(CH_2)_{0-4}$N(R')C(O)R'; —N(R')C(S)R'; —$(CH_2)_{0-4}$N(R')C(O)NR'$_2$; —N(R')C(S)NR'$_2$; —$(CH_2)_{0-4}$N(R')C(O)OR'; —N(R')N(R')C(O)R'; —N(R')N(R')C(O)NR'$_2$; —N(R')N(R')C(O)OR'; —$(CH_2)_{0-4}$C(O)R°; —C(S)R°; —$(CH_2)_{0-4}$C(O)OR'; —$(CH_2)_{0-4}$C(O)SR'; —$(CH_2)_{0-4}$C(O)OSiR'$_3$; —$(CH_2)_{0-4}$OC(O)R'; —OC(O)$(CH_2)_{0-4}$SR—, SC(S)SR'; —$(CH_2)_{0-4}$SC(O)R'; —$(CH_2)_{0-4}$C(O)NR'$_2$; —C(S)NR'$_2$; —C(S)SR'; —SC(S)SR', —$(CH_2)_{0-4}$OC(O)NR'$_2$; —C(O)N(OR')R'; —C(O)C(O)R'; —C(O)CH$_2$C(O)R'; —C(NOR')R'; —$(CH_2)_{0-4}$SSR'; —$(CH_2)_{0-4}$S(O)$_2$R'; —$(CH_2)_{0-4}$S(O)$_2$OR'; —$(CH_2)_{0-4}$OS(O)$_2$R'; —S(O)$_2$NR'$_2$; —$(CH_2)_{0-4}$S(O)R'; —N(R')S(O)$_2$NR'$_2$; —N(R')S(O)$_2$R'; —N(OR')R'; —C(NH)NR'$_2$; —P(O)$_2$R'; —P(O)R'$_2$; —OP(O)R'$_2$; —OP(O)(OR')$_2$; SiR'$_3$; —$(C_{1-4}$ straight or branched alkylene)O—N(R')$_2$; or —$(C_{1-4}$ straight or branched alkylene)C(O)O—N(R')$_2$, wherein each R' may be substituted as defined below and is independently hydrogen, $C_{1-6}$ aliphatic, —CH$_2$Ph, —O$(CH_2)_{0-1}$Ph, or a 5-6 membered saturated, partially unsaturated, or aryl ring having 0-4 heteroatoms independently selected from nitrogen, oxygen, or sulfur, or, notwithstanding the definition above, two independent occurrences of R', taken together with their intervening atom(s), form a 3-12 membered saturated, partially unsaturated, or aryl mono—or bicyclic ring having 0-4 heteroatoms independently selected from nitrogen, oxygen, or sulfur, which may be substituted as defined below.

Suitable monovalent substituents on R' (or the ring formed by taking two independent occurrences of R' together with their intervening atoms), are independently halogen, —$(CH_2)_{0-2}$R", —(haloR"), —$(CH_2)_{0-2}$OH, —$(CH_2)_{0-2}$OR", —$(CH_2)_{0-2}$CH(OR")$_2$; —O(haloR"), —CN, —N$_3$, —$(CH_2)_{0-2}$C(O)R", —$(CH_2)_{0-2}$C(O)OH, —$(CH_2)_{0-2}$C(O)OR", —$(CH_2)_{0-2}$SR", —$(CH_2)_{0-2}$SH, —$(CH_2)_{0-2}$NH$_2$, —$(CH_2)_{0-2}$NHR", —$(CH_2)_{0-2}$NHR"$_2$, —NO$_2$, —SiR"$_3$, —OSiR"$_3$, —C(O)SR", —$(C_{1-4}$ straight or branched alkylene)C(O)OR", or —SSR" wherein each R" is unsubstituted or where preceded by "halo" is substituted only with one or more halogens, and is independently selected from $C_{1-4}$ aliphatic, —CH$_2$Ph, —O$(CH_2)_{0-1}$Ph, or a 5-6-membered saturated, partially unsaturated, or aryl ring having 0-4 heteroatoms independently selected from nitrogen, oxygen, or sulfur.

Suitable divalent substituents on a saturated carbon atom of R' include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6 membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6 membered saturated, partially unsaturated, or aryl ring having 0-4 heteroatoms independently selected from nitrogen, oxygen, or sulfur.

Suitable substituents on the aliphatic group of R* include halogen, —R'', —(haloR''), —OH, —OR'', —O(haloR''), —CN, —C(O)OH, —C(O)OR'', —NH$_2$, —NHR'', —NR''$_2$, or —NO$_2$, wherein each R'' is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^t$, —NR$^t_2$, —C(O)R$^t$, —C(O)OR$^t$, —C(O)C(O)R$^t$, —C(O)CH$_2$C(O)R$^t$, —S(O)$_2$R$^t$, —S(O)$_2$NR$^t_2$, —C(S)NR$^t_2$, —C(NH)NR$^t_2$, or —N(R$^t$)S(O)$_2$R$^t$; wherein each R$^t$ is independently hydrogen, C$_{1-6}$ aliphatic which may be substituted as defined below, unsubstituted —OPh, or an unsubstituted 5-6 membered saturated, partially unsaturated, or aryl ring having 0-4 heteroatoms independently selected from nitrogen, oxygen, or sulfur, or, notwithstanding the definition above, two independent occurrences of R$^t$, taken together with their intervening atom(s) form an unsubstituted 3-12 membered saturated, partially unsaturated, or aryl mono—or bicyclic ring having 0-4 heteroatoms independently selected from nitrogen, oxygen, or sulfur.

Suitable substituents on the aliphatic group of R$^t$ are independently halogen, —R'', —(haloR''), —OH, —OR'', —O(haloR''), —CN, —C(O)OH, —C(O)OR'', —NH$_2$, —NHR'', —NR''$_2$, or —NO$_2$, wherein each R'' is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

An "suitable amino-protecting group," as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl -[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'-and 4'-pyridyl)ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl (o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3(N,N-dimethylcarboxamido)propyl carbamate, 1,1-dimethylpropynyl carbamate, di(2-pyridyl)methyl carbamate, 2-furanylmethyl carbamate, 2iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o -nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3oxazolin -2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl] amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N'p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "suitable hydroxyl protecting group" as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri (p-methoxyphenyl)methyl, 4-(4'-bromophenacyloxyphenyl) diphenylmethyl, 4,4',4''-tris(4,5-dichlorophthalimidophenyl) methyl, 4,4',4''-tris(levulinoyloxyphenyl)methyl, 4,4',4''-tris (benzoyloxyphenyl) methyl, 3-(imidazol-1-yl)bis(4',4''-dimethoxyphenyl)methyl, 1,1-bis (4-methoxyphenyl)-1'-pyrenylmethyl, 9-anthryl, 9-(9-phenyl)xanthenyl, 9-(9-phenyl -10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl) benzoate, 2-formylbenzenesulfonate, 2-(methylthiomethoxy)ethyl, 4-methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis (1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N, N-dimethylamino)ethylidene derivative, α-(N,N'- dimethylamino) benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

A "pharmaceutically acceptable form thereof" includes any pharmaceutically acceptable salts, isomers, and/or polymorphs of a palladium complex, or any pharmaceutically acceptable salts, prodrugs and/or isomers of an organic compound, as described below and herein.

As used herein, the term "isomers" includes any and all geometric isomers and stereoisomers. For example, "isomers" include cis- and trans-isomers, E- and Z- isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., Enantiomers, Racemates and Resolutions (Wiley Interscience, New York, 1981); Wilen, S.H., et al., Tetrahedron 33:2725 (1977); Eliel, E.L. *Stereochemistry of Carbon Compounds* (McGraw-Hill, NY, 1962); Wilen, S.H. *Tables of Resolving Agents and Optical Resolutions* p. 268 (E.L. Eliel, Ed., Univ. of Notre Dame Press, Notre Dame, Ind. 1972).

BRIEF DESCRIPTION OF THE DRAWINGS

FIG. 1 shows the X-ray crystal structures of nickel(II) aryl complex 1c.

FIG. 2 shows enantiodiscriminating HPLC traces.

FIG. 3 shows exemplary radio TLC scans. FIG. 3A shows an exemplary radio TLC scan of [$^{18}$F]2a, entry 1 of Table S1. The percent of total integration is listed for [$^{18}$F]2a. FIG. 31 shows an exemplary radio TLC scan of [$^{18}$F]2i, entry 51 of Table S1. The percent of total integration is listed for [$^{18}$F]2i.

FIG. 4 shows the characterization of $^{18}$F-labeled molecules. All $^{18}$F-labeled molecules were characterized by comparing the HPLC trace (measured by radioactivity) of the crude reaction mixture to the HPLC trace (measured by UV) of the corresponding authentic $^{19}$F-containing reference sample. An Agilent Eclipse XDB-C18, 5 μm, 4.6×150 mm HPLC column was used for analytical HPLC analysis. Analytical HPLC used the following mobile phases: 0.1% CF$_3$CO$_2$H in water (A) 0.1% CF$_3$CO$_2$H in acetonitrile (B). Program: 95% (A) and 5% (B) for 10 minutes. Note: radioactivity chromatographs have been offset (−0.125 min) to account for the delay volume (time) between the UV diode array detector and the radioactivity detector.

FIG. 5 shows the X-ray structure of nickel complex 1x.

Figure 1A:
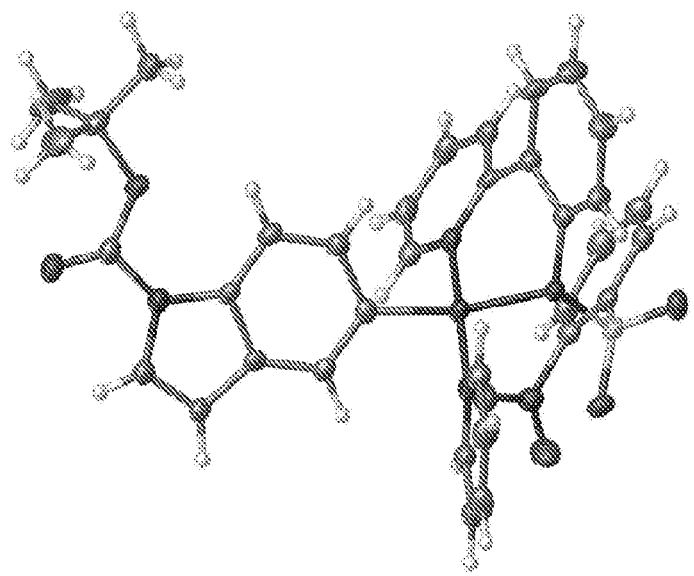
FIG. 1A shows the X-ray crystal structure of nickel(II) aryl complex 1c with hydrogen atoms rendered. The non-hydrogen atoms are depicted with 50% probability ellipsoids.

Detailed Description of Certain Embodiments of the Invention

The present invention novel nickel complexes, a method for producing these complexes and their methods of use. These complexes are useful in fluorinating an organic compound (e.g., utilizing a nucleophilic fluorine source). In particular, the inventive complexes are useful in labelling a compound with $^{18}F$ for positron emission tomography (PET). Also described herein are compositions, reaction mixtures and kits comprising these nickel complexes and fluorinated organic compounds.

Nickel Complexes

The present invention provides novel nickel complexes. Typically, the complex comprises one or more bidentate or tridentate ligands.

In one aspect, the present invention is directed to a nickel complex of formula (I):

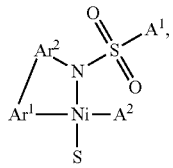
(I)

wherein:
- $Ar^1$ is aryl or heteroaryl substituted with n occurrences of $R^1$;
- $Ar^2$ is aryl or heteroaryl substituted with m occurrences of $R^2$;
- $A^1$ is $C_{1-6}$ alkyl, $C_{1-6}$ alkoxy, $C_{3-7}$ cycloalkyl, $C_{2-6}$ alkenyl, C(O)—$R^6$, C(O)O$R^6$, —$NH_2$, —$NHR^7$, —$N(R^7)_2$, $NO_2$, —OH, —$OR^6$, aryl, heteroaryl or heterocyclyl, wherein each alkyl, alkoxy, cycloalkyl, alkenyl, aryl, heteroaryl or heterocyclyl can be further substituted with o occurrences of $R^3$;
- $A^2$ is an N-heterocyclic carbene, phosphine, phosphate or heteroaryl substituted with p occurrences of $R^4$;
- S is a substrate wherein the substrate is linked through an aryl, heteroaryl or alkenyl moiety present in the substrate;
- each $R^1$, $R^2$, $R^3$ and $R^4$ is independently halo, $C_{1-6}$ alkyl, $C_{1-6}$ alkoxy, $C_{3-7}$ cycloalkyl, $C_{2-6}$ alkenyl, C(O)—$R^6$, C(O)O$R^6$, —$NH_2$, —$NHR^7$, —$N(R^7)_2$, $NO_2$, —OH, —$OR^6$, aryl, heteroaryl or heterocyclyl, wherein each alkyl, alkoxy, cycloalkyl, alkenyl, aryl, heteroaryl or heterocyclyl can be further substituted with 0-3 occurrences of $R^8$;
- $R^6$ is $C_{1-6}$ alkyl, $C_{1-6}$ alkenyl, $C_{3-7}$ cycloalkyl, —C(O)O—$C_{1-6}$ alkyl, aryl, heteroaryl or heterocyclyl;
- each $R^7$ is independently $C_{1-6}$ alkyl, $C_{1-6}$ alkenyl, $C_{3-7}$ cycloalkyl, —C(O)—$C_{1-6}$ alkyl, —C(O)O-$C_{1-6}$ alkyl, aryl, heteroaryl or heterocyclyl;
- each $R^8$ is independently halo, $C_{1-6}$ alkyl, $C_{1-6}$ alkoxy, $C_{1-6}$ alkenyl, $C_{3-7}$ cycloalkyl, $C_{1-6}$ alkyl-amine, —C(O)—$C_{1-6}$ alkyl, —C(O)O—$C_{1-6}$ alkyl, $C_{0-6}$ alkyl-$NHR^7$, aryl, aryloxy, aralkyl, heteroaryl, heteroaralkyl, heterocyclyl or heterocyclylalkyl or wherein two adjacent $R^8$ moieties, taken together with the atoms to which they are attached, form a $C_{3-7}$ cycloalkyl, aryl, heteroaryl or heterocyclyl group, wherein each alkyl, alkoxy, alkenyl, cycloalkyl, aryl; and
- m, n, o and p are each independently an integer from 0-5.

In some embodiments, the nickel complex of formula (I) is a complex of formula (II):

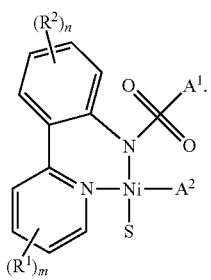
(II)

In some embodiments, the nickel complex of formula (I) or (II) is a complex of formula (III):

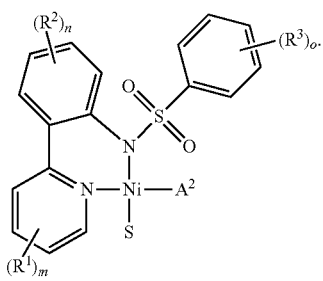
(III)

In some embodiments, the nickel complex of formula (I), (II) or (III) is a complex of formula (IV):

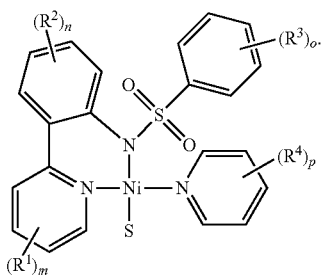
(IV)

In some embodiments, the nickel complex of formula (I), (II), (III) or (IV) is a complex of formula (V):

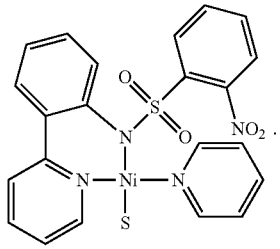
(V)

Preparation of Nickel Complexes

The inventive nickel complexes are typically prepared as described in the methods below. The method of making a nickel complex of formula (I) comprises treating an organic compound of formula (VI):

S—X$^1$  (VI)

with tetramethylethylenediamine and bis(1,5-cyclooctadiene)nickel to provide a nickel complex of formula (VII):

(VII)

the method further comprising, treating a nickel complex of formula (VII) with a silver compound of formula (VIII) and A$^2$:

(VIII)

to provide a nickel complex of formula (I), wherein Ar$^1$, Ar$^2$, A$^1$, A$^2$, A$^3$, R$^1$, R$^2$, R$^3$, R$^4$, R$^6$, R$^7$, R$^8$, m, n, o and p are as defined for formula (I) and X$^1$ is a leaving group.

In some embodiments, X$^1$ is halo (e.g., bromo). In some embodiments, X$^1$ is —OTf.

In another aspect, the method of making a nickel complex of formula (I) comprises treating an organic compound of formula (X):

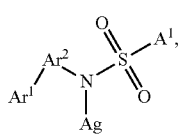
S—B(OR$^9$)$_2$  (X), with a nickel cubane complex of formula (XI):

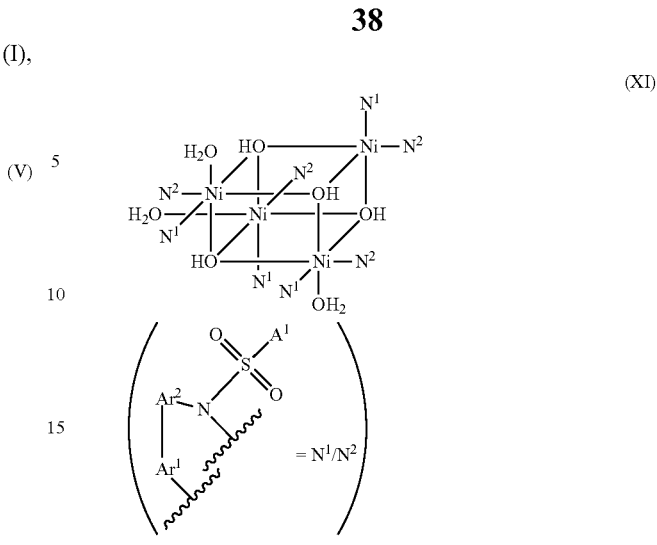
(XI)

to provide an organic nickel complex of formula (I) wherein:
Ar$^1$, Ar$^2$, A$^1$, A$^2$, A$^3$, R$^1$, R$^2$, R$^3$, R$^4$, R$^6$, R$^7$, R$^8$, m, n, o and p are as defined for formula (I); and
R$^9$ is defined as halo, C$_{1-6}$ alkyl, C$_{1-6}$ alkoxy, C$_{3-7}$ cycloalkyl, C$_{2-6}$ alkenyl, C(O)—R$^6$, C(O)OR$^6$, —NH$_2$, —NHR$^7$, —N(R$^7$)$_2$, —OH, —OR$^6$, aryl, heteroaryl, or heterocyclyl, wherein each alkyl, alkoxy, cycloalkyl, alkenyl, aryl, heteroaryl, or heterocyclyl can be further substituted with 0-3 occurrences of R$^8$.

In some embodiments, R$^9$ is —OH. In some embodiments, R$^9$ is —OH. In some embodiments, R$^9$ is methoxy. In some embodiments, R$^9$ is ethoxy. In some embodiments, R$^9$ is isopropoxy. In some embodiments, two R$^9$ groups are taken together as a pinacol. In some embodiments, two R$^9$ groups are taken together as catechol.

In another aspect, the method of making a nickel complex of formula (I) comprises treating an organic compound of formula (XIII):

S—B(X$^1$)$_4$M$^1$  (XIII), with a nickel cubane complex of formula (XI):

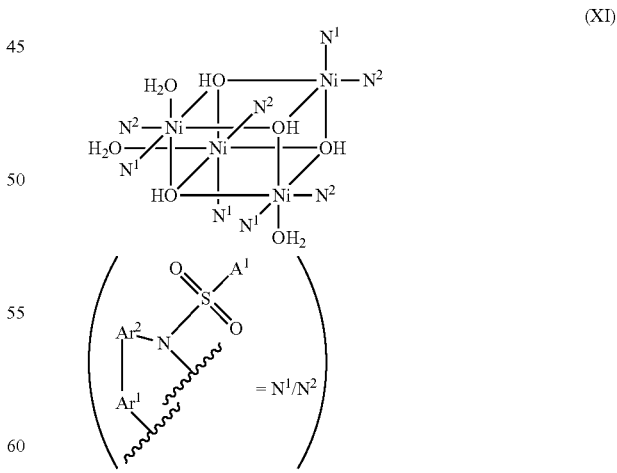
(XI)

to provide an organic nickel complex of formula (I) wherein;
Ar$^1$, Ar$^2$, A$^1$, A$^2$, A$^3$, R$^1$, R$^2$, R$^3$, R$^4$, R$^6$, R$^7$, R$^8$, m, n, o and p are as defined for formula (I);
X$^1$ is a leaving group; and
M$^1$ is an alkali metal.

In some embodiments, $X^1$ is —F. In some embodiments, $X^1$ is —Cl. In some embodiments, $X^1$ is —Br. In some embodiments, $X^1$ is —I. In some embodiments, $X^1$ is —OTf. In some embodiments, $X^1$ is —OTs. In some embodiments, $X^1$ is —OH.

In some embodiments, $M^1$ is sodium. In some embodiments, $M^1$ is potassium.

Fluorine Sources

As generally described above, the process for utilizing the nickel complexes described herein utilizes a source of fluorine. Fluorine occurs naturally as fluorine-19 ($^{19}F$). Fluorine-18 ($^{18}F$) is a radioisotope of fluorine.

In certain embodiments, the source of fluorine is a fluoride source comprising water (i.e., negatively charged fluoride ions present in a mixture of water and acetonitrile). The fluoride source may contain a particular isotope of fluorine (e.g., $^{18}F$). In some embodiments, the fluoride source contains $^{18}F$ fluoride (i.e., transfers an $^{18}F$ fluorine substituent to the organic compound). In certain embodiments, reaction of the $^{18}F$ fluoride source in the inventive process provides a fluorinated $^{18}F$-labeled organic compound.

In some embodiments, the fluoride source comprising water (e.g., the aqueous fluoride source contains $^{18}F$) is produced using a cyclotron. In some embodiments, the fluoride source comprising water is produced using a cyclotron in $^{18}O$ enriched water.

In certain embodiments, the source of fluorine is a fluorinating agent. In certain embodiments, the fluorinating agent is a nucleophilic fluorinating agent. In certain embodiments, when the fluorinating agent is a nucleophilic fluorinating agent, the methods described herein further comprise an oxidant as described herein. In certain embodiments, the fluorinating agent is commercially available. In certain embodiments, the nucleophilic fluorinating agent is an inorganic fluorinating agent. In some embodiments, the nucleophilic fluorinating agent is sodium fluoride (NaF), silver fluoride (AgF), tetrabutylammonium fluoride ($NH_4F$), substituted tetrabutylammonium fluoride ($NR_4F$), cesium fluoride (CsF), potassium fluoride (KF), tetrabutylammonium difluorotriphenylsilicate (TBAT) and $XeF_2$ In some embodiments, the nucleophilic fluorinating agent comprises $^{18}F$ or $^{19}F$.

In some embodiments, the fluorinating agent is an electrophilic fluorinating agent. In some embodiments, the electrophlic fluorinating agents include, but are not limited to, N-fluoropyridinium triflate, N-fluoro-2,4,6-trimethylpyridinium triflate, N-fluoro-2,4,6-trimethylpyridinium tetrafluoroborate, N-fluoro-2,6-dichloropyridinium tetrafluoroborate, N-fluoro-2,6-dichloropyridinium triflate, N-fluoropyridinium pyridine heptafluorodiborate, N-fluoropyridinium tetrafluoroborate, N-fluoropyridinium triflate, N-fluoroarylsulfonimide (e.g., N-fluorobenzenesulfonimide) and N-chloromethyl-N'-fluorotriethylenediammonium bis (triflate) (Selectfluor®). In certain embodiments, the fluorinating agent is Selectfluor®. In certain embodiments, the fluorinating agent is N-fluoropyridinium triflate. In certain embodiments, the fluorinating agent is N-fluoro-2,4,6-trimethylpyridinium triflate. In certain embodiments, the fluorinating agent is N-fluoro-2,4,6-trimethylpyridinium tetrafluoroborate. In certain embodiments, the fluorinating agent is N-fluoro-benzenesulfonimide. In certain embodiments, the fluorinating agent is xenon difluoride. In certain embodiments, the fluorinating agent is N-chloromethyl-N'-fluorotriethylenediammonium bis(tetrafluoroborate) (Selectfluor®). In some embodiments, the electrophilic fluorinating agent comprises $^{18}F$ or $^{19}F$.

The fluorinating agent may contain a particular isoptope of fluorine. In certain embodiments, the fluorinating agent contains $^{19}F$ (i.e., transfers an $^{19}F$ fluorine substituent to the organic compound). In certain embodiments, reaction of the $^{19}F$ fluorinating agent in the inventive process provides a fluorinated $^{19}F$-labeled organic compound.

In certain embodiments, the fluorinating agent contains $^{18}F$ (i.e., transfers an $^{18}F$ fluorine substituent to the organic compound). In certain embodiments, reaction of the $^{18}F$ fluorinating agent in the inventive process provides a fluorinated $^{18}F$-labeled organic compound.

However, in certain embodiments, the fluorinating agent is labeled with a mixture of $^{18}F$ and $^{19}F$. In certain embodiments, reaction of the fluorinating agent with a mixture of $^{19}F$ and $^{18}F$ in the inventive process provides a mixture of fluorinated $^{19}F$-labeled organic compound and fluorinated $^{18}F$-labeled organic compound. In certain embodiments, the portion of each of $^{19}F$ and $^{18}F$ in the mixture is known. Any of the above fluorinated agents may be labeled with $^{19}F$ or $^{18}F$.

Substrates and Fluorinated Organic Compounds

As generally described above, the invention provides a process for fluorinating substrate (e.g., an organic substrate) using a nickel complex. In certain embodiments, the substrate has a particular substituent (i.e., the nickel complex) that is replaced with the fluoride from the complex.

The substrate utilized in the inventive process includes, but is not limited to, small organic molecules and/or large organic molecules. A small organic molecule include any molecule having a molecular weight of less than 1000 g/mol, of less than 900 g/mol, of less than 800 g/mol, of less than 700 g/mol, of less than 600 g/mol, of less than 500 g/mol, of less than 400 g/mol, of less than 300 g/mol, of less than 200 g/mol or of less than 100 g/mol. A large organic molecule include any molecule of between 1000 g/mol to 5000 g/mol, of between 1000 g/mol to 4000 g/mol, of between 1000 g/mol to 3000 g/mol, of between 1000 g/mol to 2000 g/mol, or of between 1000 g/mol to 1500 g/mol. Substrates include, but are not limited to, aryl compounds, heteroaryl compounds, carbocyclic compounds, heterocyclic compounds, aliphatic compounds, heteroaliphatic compounds, as well as polymers, peptides, glycopeptides, and the like. In certain embodiments, the substrate is an optionally substituted alkenyl, optionally substituted heteroalkenyl, optionally substituted aryl, or optionally substituted heteroaryl compound. In certain embodiments, the substrate is an aryl-containing compound.

In certain embodiments, a substrate is a polymer.
In certain embodiments, a substrate is a peptide.
In certain embodiments, a substrate is biologically active.
For example, in certain embodiments, the substrate is an agrochemical. In certain embodiments, the substrate is an insecticide or a pheromone of insect origin.

In certain embodiments, the substrate is pharmaceutical agent. For example, in certain embodiments, the pharmaceutical agent is an anti-emetic, anti-coagulant, anti-platelet, anti-arrhythmic, anti-herpertensive, anti-anginal, a lipid-modifying drug, sex hormone, anti-diabetic, antibiotic, anti-viral, anti-fungal, anti-cancer, immunostimulant, immunosuppressant, anti-inflammatory, anti-rheumatic, anesthetic, analgesic, anticonvulsant, hypnotic, anxiolytic, anti-psychotic, barbituate, antidepressant, sedative, anti-obesity, anti-histime, anti-eleptic, anti-manic, opioid, anti-Parkinson, anti-Alzheimers, anti-dementia, an anti-substance dependance drug, cannabinoid, 5HT-3 antagonist, monoamine oxidase inhibitor (MAOI), selective serotonin reuptake inhibitor (SSRI), or stimulant. In certain embodiments, the pharmaceutical agent is a psychotropic agent. In certain embodiments, the pharmaceutical agent is any pharmaceutical agent approved by the United States Food and Drug Administration (FDA) for administration to a human (see, e.g., www.accessdata.fda.gov/scripts/cder/drugsatfda).

In certain embodiments, the pharmaceutical agent is an antibiotic. In certain embodiments, the pharmaceutical agent is a lipid modifying drug. In certain embodiments, the pharmaceutical agent is a CNS drug (i.e., drug acting on the Central Nervous System). CNS drugs include, but are not limited to, hypnotics, anxiolytics, antipsychotics, barbituates, antidepressants, antiobesity, antihistimes, antieleptics, antimanics, opioids, analgesics, anti -Parkinson, anti-Alzheimers, anti-dementia, anti-substance dependance drugs, cannabinoids, 5HT-3 antagonists, monoamine oxidase inhibitors (MAOIs), selective serotonin reuptake inhibitors (SSRIs) and stimulants. Exemplary pharmaceutical agents such as antibiotics, lipid modifying agents and CNS agents are provided in International Application Nos. PCT/US2010/020544; PCT/US2010/020540 and PCT/US2010/041561, each of which is incorporated by reference herein in its entirety.

In certain embodiments, the substrate, after fluorination, is biologically active. In certain embodiments, the substrate, prior to fluorinated, is also biologically active.

In certain embodiments, the process provides after fluorination of the substrate a known biologically active fluorinated compound, such as a fluorinated agrochemical or fluorinated pharmaceutical agent.

For example, in certain embodiments, the process provides after fluorination, the following compounds:

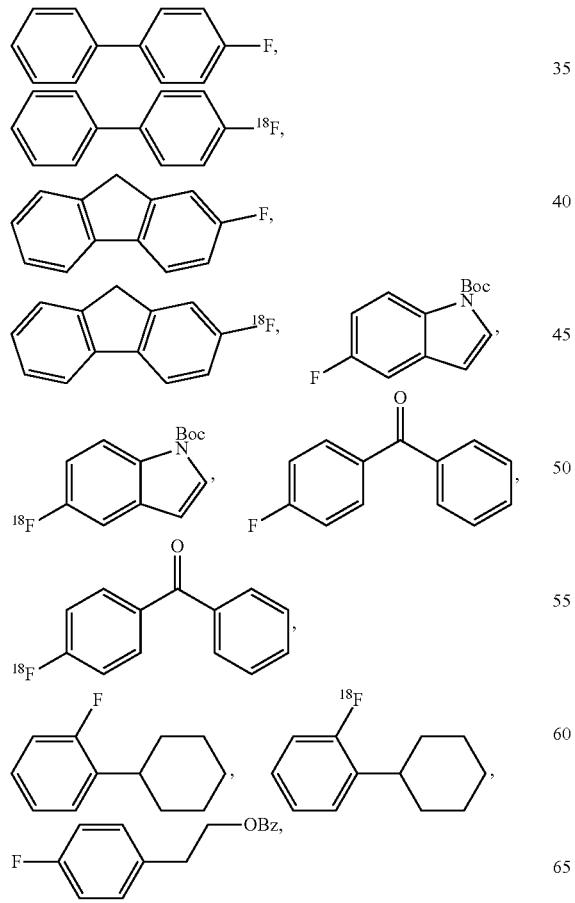

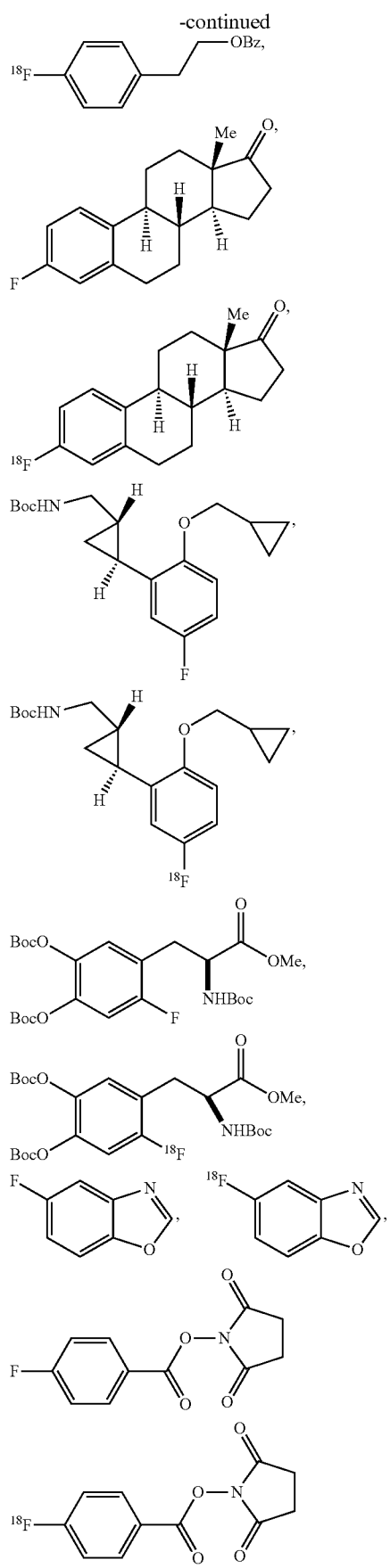

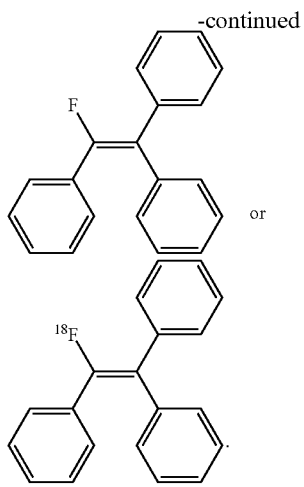

Exemplary Reaction Conditions

Described herein are compositions comprising a nickel complex described herein, including a reaction mixture, e.g., a reaction mixture that is present during a method or process described herein. As defined generally herein, in certain embodiments, the process comprises mixing a nickel comprising complex described herein and a substrate with a fluorinating agent and an oxidant (e.g., a compound of formula (IX)) under conditions sufficient to fluorinate the substrate to thereby provide a fluorinated organic compound.

In certain embodiments, the nickel complex can be bound to a solid support.

In certain embodiments, the method further comprises a solvent. In certain embodiments, the solvent is an organic solvent. In certain embodiments, the solvent is an aprotic solvent. Exemplary organic solvents include, but are not limited to, benzene, toluene, xylenes, methanol, ethanol, isopropanol, acetonitrile, acetone, ethyl acetate, ethyl ether, tetrahydrofuran, methylene chloride, dichloroethane and chloroform, or a mixture thereof. In certain embodiments, the solvent is acetonitrile. In certain embodiments, the solvent is acetonitrile.

In certain embodiments, the reaction further comprises heating. In certain embodiments, the reaction further comprises cooling (e.g., to 0 °C. or lower). In certain embodiments, the reaction takes place under an inert atmosphere (e.g, an atmosphere of an inert gas such as nitrogen or argon). In certain embodiments, the reaction takes place under anhydrous conditions (e.g., conditions that are substantially free of water).

Methods

Described herein are methods for fluorination of organic compounds. In certain embodiments, the fluorination reaction is regiospecific.

Introduction of fluorine into a certain position of bioactive compound such as a pharmaceutical agent and an agricultural chemical may remarkably reduce the toxicity of the compound. This is due to the mimic and blocking effect characterized by fluorine.

Organofluorine compounds are emerging as chemical specialties of significant and increasing commercial interest. A major driver has been the development of fluorine-containing bio-active molecules for use as medicinal and plant-protection agents. Other new applications involving organofluorine chemistry are in the synthesis of liquid crystals, surface active agents, specialty coatings, reactive dyes, and even olefin polymerization catalysts.

$^{19}$F-fluorinated organic compounds may be useful for magnetic resonance imaging (MRI) technology. MRI is a primarily a medical imaging technique most commonly used in radiology to visualize the structure and function of the body. It provides detailed images of the body in any plane. MRI contrast agents are a group of contrast media used to improve the visibility of internal body structures in MRI. Contrast agents alter the relaxation times of tissues and body cavities where they are present, which depending on the image weighting can give a higher or lower signal. Fluorine-containing constrast agents may be especially useful due to the lack of fluorine chemistry in the human body. This could, for example provide a detailed view of acidic regions, such as those containing cancer cells. $^{19}$F-labeled MRI contrast agents may add chemical sensitivity to MRI and could be used to track disease progression without the need to take tissue or fluid samples.

$^{19}$F-fluorinated organic compounds may also be useful as probes for nuclear magnetic resonance (NMR) spectroscopy. Fluorine has many advantages as a probe for NMR spectroscopy of biopolymers. $^{19}$F has a spin of one-half, and its high gyromagnetic ratio contributes to its high sensitivity (approximately 83% of the sensitivity of $^{1}$H). It also facilitates long-range distance measurements through dipolar-dipolar coupling. Moreover, the near-nonexistence of fluorine atoms in biological systems enables $^{19}$F NMR studies without background signal interference. Furthermore, the chemical shift of $^{19}$F has been shown to be very sensitive to its environment.

$^{18}$F-fluorinated organic compounds are particularly useful for positron-emission tomography (PET) imaging technology. PET is a noninvasive imaging technology that is currently used in the clinic to image cancers and neurological disorders at an early stage of illness. PET tracers are molecules which incorporate a PET-active nucleus and can therefore be visualized by their positron emission in the body. The fluorine isotope $^{18}$F is the most common nucleus for PET imaging because of its superior properties to other nuclei.

The $^{18}$F radioisotope has a half-life of 109 minutes. The short half-life dictates restrictions on chemical synthesis of PET tracers, because introduction of the fluorine atom has to take place at a very late stage of the synthesis to avoid the unproductive decay of $^{18}$F before it is injected into the body. Fluoride ion is the most common reagent to introduce $^{18}$F but the specific chemical properties of the fluoride ion currently limit the available pool of PET tracers. Due to the narrow functional group compatibility of the strongly basic fluoride ion, only a limited set of chemical reactions can be employed for fluorination, and hence the synthesis of PET tracers is limited to fairly simple molecules such as FDG. The field of PET imaging would benefit from the availability of a new method that is capable of introducing radiolabeled fluoride into structurally more complex organic molecules. An easy access to drug-based PET tracers would simplify determining the fate of such drugs in the body and thereby help to identify and understand their mode of action, bioavailability and time-dependent biodistribution.

Compositions and Routes of Administration

The complexes described herein including a nickel complex described herein can be used to produce fluorinated organic compounds (e.g., a biologically active fluorinated organic compound). The compositions delineated herein may include these fluorinated organic compounds described herein, such as fluorinated pharmaceutical agents, as well as additional therapeutic agents if present, in amounts effective for achieving a modulation of disease or disease symptoms, including those described herein. In some embodiments, the fluorinated compound is made by a method described herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3- hydroxypropyl-β-cyclodextrins, or other solubilized derivatives may also be advantageously used to enhance delivery of compounds of the formulae described herein.

Kits

A complex or compound described herein (e.g., a nickel complex described herein, an organic compound, a source of fluorine (e.g., a source of fluorine described herein such as a fluoride source comprising water or a fluorinating agent such as a fluorinating agent described herein), or a fluorinated compound, such as a fluorinated pharmaceutical agent) may be provided in a kit. The kit includes (a) a compound used in a method described herein, and, optionally (b) informational material. In some embodiments, the kit further includes an oxidant (e.g., an oxidant described herein). In some embodiments, the kit further includes a metal chelator (e.g., a metal chelator described herein such as 18-crown-6). The informational material can be descriptive, instructional, marketing or other material that relates to the methods described herein and/or the use of the compounds for the methods described herein. In some embodiments, the nickel complex is bound to a solid support.

The informational material of the kits is not limited in its form. In one embodiment, the informational material can include information about production of the compound, molecular weight of the compound, concentration, date of expiration, batch or production site information, and so forth.

In one embodiment, the informational material can include instructions to administer a compound described herein in a suitable manner to perform the methods described herein, .

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In some embodiments, the components of the kit are stored under inert conditions (e.g., under Nitrogen or another inert gas such as Argon). In some embodiments, the components of the kit are stored under anhydrous conditions (e.g., with a desiccant). In some embodiments, the components are stored in a light blocking container such as an amber vial.

A compound described herein can be provided in any form, e.g., liquid, dried or lyophilized form. It is preferred that a compound described herein be substantially pure and/or sterile. When a compound described herein is provided in a liquid solution, the liquid solution preferably is an aqueous solution, with a sterile aqueous solution being preferred. When a compound described herein is provided as a dried form, reconstitution generally is by the addition of a suitable solvent. The solvent, e.g., sterile water or buffer, can optionally be provided in the kit.

The kit can include one or more containers for the composition containing a compound described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit forms of a compound described herein. The containers of the kits can be air tight, waterproof (e.g., impermeable to changes in moisture or evaporation), and/or light-tight.

EXAMPLES

General Methods

All air- and moisture-insensitive reactions were carried out under an ambient atmosphere, magnetically stirred, and monitored by thin layer chromatography (TLC) using EMD TLC plates pre-coated with 250 µm thickness silica gel 60 F254 plates and visualized by fluorescence quenching under UV light. Flash chromatography was performed on Dynamic Adsorbents Silica Gel 40-63 µm particle size using a forced flow of eluent at 0.3-0.5 bar pressure. All air- and moisture-sensitive manipulations were performed using oven-dried glassware, including standard Schlenk and glovebox techniques under an atmosphere of nitrogen. Methylene chloride was purged with nitrogen, dried by passage through activated alumina, and stored over 3 Å molecular sieves. Benzene, benzene-$d_6$, diethyl ether, toluene, pentane, dioxane and THF were distilled from deep purple sodium benzophenone ketyl. Methylene chloride-$d_2$ was dried over $CaH_2$ and vacuum-distilled. Acetonitrile and acetonitrile-$d_3$ were dried over $P_2O_5$ and vacuum-distilled. Pyridine and tetramethylethylenediamine (TMEDA) were dried over $CaH_2$ and distilled. DMSO was distilled from sodium triphenylmethanide and stored over 3 Å sieves. Acetone was distilled over $B_2O_3$.

MeOH was degassed at −30 °C. under dynamic vacuum (10$^{-4}$ Torr) for one hour and stored over 3 Å sieves. Anhydrous DMF and dioxane bottles equipped with a SureSeal™ were purchased from Sigma Aldrich®. 18-Crown-6 was sublimed. KF was ground finely and dried at 200 °C. under dynamic vacuum (10$^{31\ 4}$ Torr) before use. Ni(COD)$_2$ and all other chemicals were used as received. All deutrated solvents were purchased from Cambridge Isotope Laboratories. Ni(COD)$_2$ and 18-crown-6 were purchased from Strem Chemicals. (Diacetoxyiodo)benzene, potassium fluoride, 4-methoxypyridine, α-tetralone, pyrrolidine, p-toluenesulfonic acid, p-methoxybenzenesulfonamide, and F-TEDA-BF$_4$ (Selectfluor®) were purchased from Sigma-Aldrich®. TMSOTf and trifluoroacetic acid were purchased from Oakwood Products.

NMR spectra were recorded on either a Varian Unity/Inova 600 spectrometer operating at 600 MHz for $^1$H acquisitions, a Varian Unity/Inova 500 spectrometer operating at 500 MHz and 125 MHz for $^1$H and $^{13}$C acquisitions, respectively, a Varian Mercury 400 spectrometer operating at 375 MHz and 101 MHz for $^{19}$F and $^{13}$C acquisitions, respectively, or a Varian Mercury 300 spectrometer operating at 100 MHz for $^{11}$B acquisitions. Chemical shifts were referenced to the residual proton solvent peaks ($^1$H: CDCl$_3$, δ7.26; C$_6$D$_6$, δ7.16; CD$_2$Cl$_2$, δ5.32; D$_2$O, δ4.79; (CD$_3$)$_2$SO, δ2.50; CD$_3$CN, δ1.94), solvent $^{13}$C signals (CDCl$_3$, δ77.16; C$_6$D$_6$, δ128.06; CD$_2$Cl$_2$, δ53.84; CD$_3$CN, δ1.32, (CD$_3$)$_2$SO, δ39.52), dissolved or external neat PhF ($^{19}$F, δ−113.15 relative to CFCl$_3$) or dissolved 3-nitrofluorobenzene (−112.0 ppm). Signals are listed in ppm, and multiplicity identified as s=singlet, br=broad, d=doublet, t=triplet, q=quartet, quin=quintet, sep=septet, m=multiplet; coupling constants in Hz; integration. Concentration under reduced pressure was performed by rotary evaporation at 25-30 °C. at appropriate pressure. Purified compounds were further dried under high vacuum (0.01-0.05 Torr). Yields refer to purified and spectroscopically pure compounds.

Example 1
Synthesis of (2-(2-Pyridinyl)phenyl-2-nitrobenzenesulfonamide)silver (I) complex (8) and hypervalent iodine oxidant (6)

2-(2-Pyridinyl)aniline (S1)

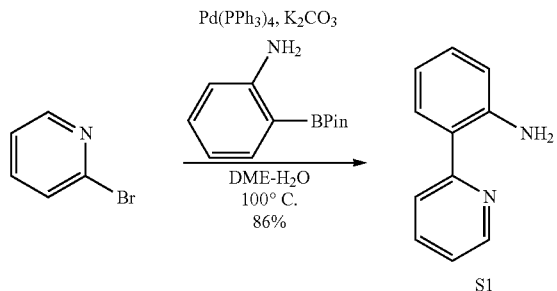

Under air, to 2-bromopyridine (4.54 g, 28.7 mmol, 1.00 equiv) in DME—H$_2$O (1:1, 100 mL) at 23 °C. was added K$_2$CO$_3$ (5.96 g, 43.1 mmol, 1.50 equiv), 2-aminophenylboronic acid pinacol ester (6.30 g, 28.7 mmol, 1.00 equiv), and tetrakis(triphenylphosphine)palladium (1.66 g, 1.44 mmol, 5.00 mol%). The reaction mixture was stirred at 100 °C. for 3.0 h. After cooling to 23 °C., the phases were separated and the aqueous phase was extracted with EtOAc (3×50 mL). The combined organic phases were washed with brine (100 mL) and dried (Na$_2$SO$_4$). The filtrate was concentrated in vacuo and the residue was purified by chromatography on silica gel eluting with hexanes/EtOAc 4:1 (v/v) to afford 4.20 g of the title compound as a red-brown oil (86%). R$_f$=0.38 (hexanes/EtOAc 3:1 (v/v)). NMR Spectroscopy: $^1$H NMR (500 MHz, CDCl$_3$, 23 °C., δ): 8.61-8.60 (m, 1H), 7.78-7.75 (m, 1H), 7.65 (d, J=7.9 Hz, 1H), 7.51 (dd, J=7.6 Hz, 1.4 Hz, 1H), 7.19-7.16 (m, 2H), 6.80-6.76 (m, 2H), 5.72 (br s, 2H). $^{13}$C NMR (125 MHz, CDCl$_3$, 23 °C., δ): 159.5, 147.9, 146.6, 136.9, 129.9, 129.4, 122.2, 122.2, 121.0, 117.6, 117.2.

2-(2-Pyridinyl)-2-nitrobenzenesulfonanilide (S2)

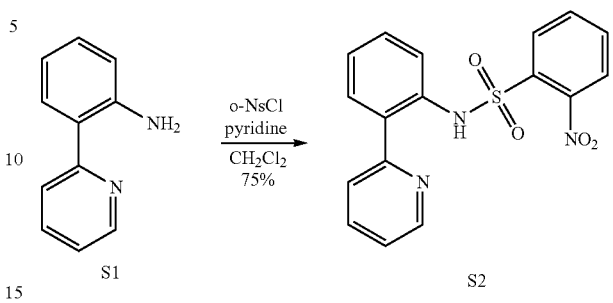

To 2-(2-pyridinyl)aniline (S1) (851 mg, 5.00 mmol, 1.00 equiv) in CH$_2$Cl$_2$ (10 mL) at 0 °C. was added pyridine (1.60 mL, 20.0 mmol, 4.00 equiv) and 2-nitrobenzenesulfonyl chloride (2.20 g, 10.0 mmol, 2.00 equiv). The reaction mixture was warmed to 23 °C. and stirred for 2.0 hr before the addition of water (10 mL). The phases were separated and the aqueous layer was extracted with CH$_2$Cl$_2$ (3×8 mL). The combined organic phases were washed with brine (30 mL) and dried (Na$_2$SO$_4$). The filtrate was concentrated in vacuo and the residue was purified by chromatography on silica gel eluting with hexanes/EtOAc 3:7 (v/v) to afford 1.33 g of the title compound as a pale-yellow solid (75%). R$_f$=0.12 (hexanes/EtOAc 7:3 (v/v)). Melting Point: 91-94 °C. NMR Spectroscopy: $^1$H NMR (500 MHz, CDCl$_3$, 23 °C., δ): 8.73 (d, J=5.0 Hz, 1H), 7.94 (dd, J=7.5 Hz, 2.0 Hz, 1H), 7.82 (dd, J=8.0 Hz, 1.0 Hz, 1H), 7.74 (ddd, J=7.5 Hz, 7.5 Hz, 2.0 Hz, 1H), 7.63-7.52 (m, 5H), 7.38 (ddd, J=7.5 Hz, 7.5 Hz, 1.5 Hz, 1H), 7.27-7.24 (m, 1H), 7.18 (ddd, J=7.5 Hz, 7.5 Hz, 1.0 Hz, 1H). $^{13}$C NMR (125 MHz, CDCl$_3$, 23 °C., δ): 156.9, 156.2, 148.0, 137.9, 136.4, 133.6, 132.2, 131.0, 130.0, 129.0, 127.1, 125.0, 124.7, 122.4, 121.9, 121.9, 110.9. Mass Spectrometry: HRMS-FIA (m/z): Calcd for [C$_{17}$H$_{13}$N$_3$O$_4$S+H], 356.06995. Found, 356.07008.

Synthesis of (2-(2-Pyridinyl)phenyl-2-nitrobenzenesulfonamide)silver (I) (8)

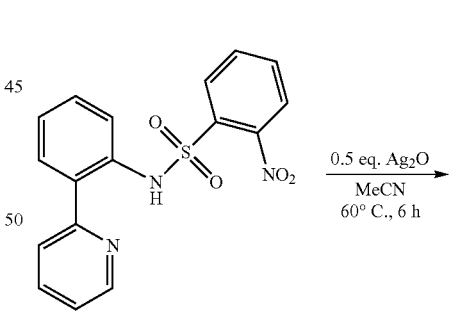

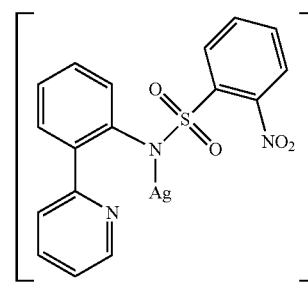

To silver(I) oxide (4.99 g, 21.5 mmol, 0.500 equiv) in CH$_3$CN (200 mL) at 23 °C. was added 2-(2-pyridinyl)phenyl-2-nitrobenzenesulfonanilide (S2) (15.3 g, 43.1 mmol, 1.00 equiv). After stirring for 12 h at 65 °C., the resulting light gray solid was collected on a frit and in vacuo to afford 18.3 g of the title compound as a light gray solid (92%). Anal: calcd for C$_{17}$H$_{12}$AgN$_3$O$_4$S: C, 44.17; H, 2.62; N, 9.09; found: C, 44.06; H, 2.66; N, 9.00. The $^1$H and $^{13}$C NMR spectra are not obtained due to a poor solubility.

1,1'-(phenyl-λ$^3$-iodanediyl)bis(4-methoxypyridinium) bis(trifluoromethanesulfonate) (6)

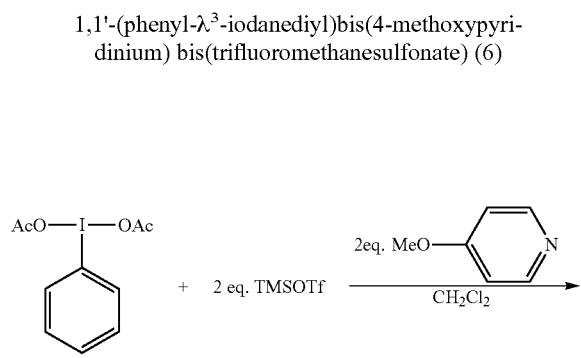

Based on a reported procedure: All manipulations were carried out in a dry box under a N$_2$ atmosphere. To (diacetoxyiodo)benzene (3.00 g, 9.31 mmol, 1.00 equiv) dissolved in CH$_2$Cl$_2$ (100 mL) in a round-bottom flask was added TMSOTf (4.14 g, 18.6 mmol, 2.00 equiv) dropwise over 1 minute at 23 °C. 4-Methoxypyridine (2.03 g, 18.6 mmol, 2.00 equiv) in CH$_2$Cl$_2$ (15 mL) was added to the solution dropwise over 5 minutes. The reaction mixture was concentrate until a white solid was observed. To the reaction mixture was added 100 mL of Et$_2$O and the resulting solid was collected on a frit. The solid was washed with Et$_2$O (3 x 10 mL) and subsequently dried under vacuum to afford 6.52 g of the title compound as a colorless solid (97%). NMR Spectroscopy: c $^1$H NMR (500 MHz, CD$_3$CN, 23 °C., δ): 8.77 (d, J=7.5 Hz, 4H), 8.60 (d, J=8.5 Hz, 2H), 7.79 (t, J=7.5 Hz, 1H), 7.64 (t, J=8.5 Hz, 2H), 7.19 (d, J=7.5 Hz, 4H), 3.99 (s, 3H). $^{13}$C NMR (125 MHz, CD$_3$CN, 23 °C., δ): 172.1, 149.9, 136.1, 135.7, 134.2, 121.9 (q, J=319 Hz, triflate), 115.3, 58.5. $^{19}$F NMR (375 MHz, CD$_3$CN, 23 °C., δ): −77.5. Anal: calcd for C$_{20}$H$_{19}$F$_6$IN$_2$O$_8$S$_2$: C, 33.34; H, 2.66; N, 3.89; found: C, 33.05; H, 2.59; N, 3.73.

Example 2

Synthesis of Aryl Nickel Complexes (1a-1l)

General Procedure for Nickel(II) Aryl Bromide Complexes (7a-7k)

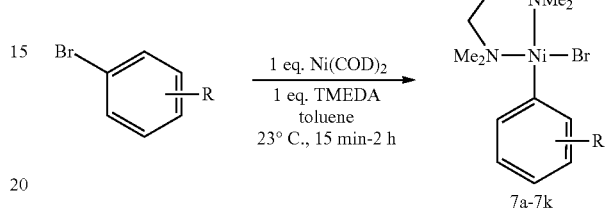

To a solution of tetramethylethylenediamine (TMEDA, 0.107mL, 0.717 mmol, 1.00 equiv) and aryl bromide (0.717 mmol, 1.00 equiv) in toluene (4 mL) was added bis(cyclooctadiene)nickel(0) (Ni(COD)$_2$, 0.200 g, 0.717 mmol, 1.00 equiv), and the mixture was stirred at room temperature for 15 min to 3 h depending on aryl bromides. Pentane (16 mL) was added to the mixtures and the corresponding nickel complexes were collected on a frit. The solid was washed with pentane (3×5 mL) and dried in vacuo.

General Procedure for Nickel(II) Aryl Complexes (1a-1l)

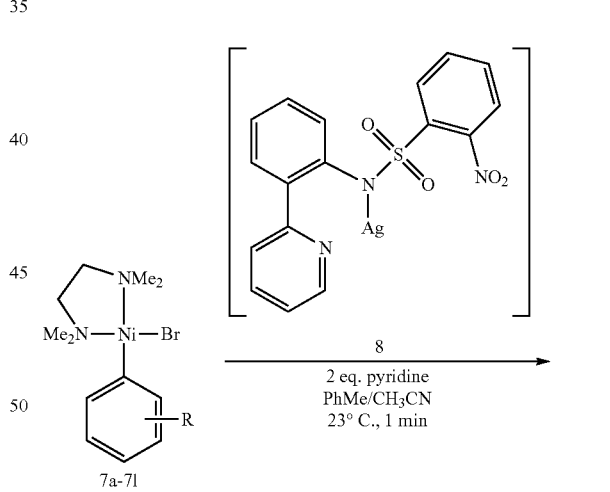

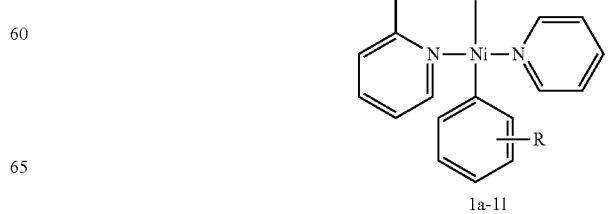

To (2-(2-Pyridinyl)phenyl-2-nitrobenzenesulfonamide)silver(I) (8) (1.00 equiv) and nickel(II) aryl or alkenyl bromide complex (7a-7l, 200 mg, 1.00 equiv) in a 20 mL vial was added an toluene solution (4 mL) that contained pyridine (2.00 equiv) at 23 °C., followed by addition of acetonitrile (1.0 mL). After stirring for 1 min at 23, the solution was concentrated and the residual solid was triturated with 20 mL of pentane and collected on a frit. The solid was extracted with $CH_2Cl_2$ (5 mL) and the solution was filtered through a pad of Celite on a glass frit and the filtered cake was extracted further with dichloromethane (3×1 mL). The combined filtrate was concentrated in vacuo and the resulting residue was redissolved in dichloromethane and the solution was filtered through a pad of Celite and the filtrate was concentrated in vacuo. The resulting residue was purified by recrystallization ($CH_2Cl_2$/pentane) or chromatography on silica gel.

Synthesis of Nickel(II) Aryl Bromide (7a)

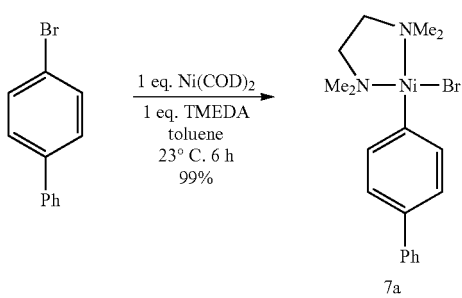

To a solution of TMEDA (0.107 mL, 0.717 mmol, 1.00 equiv) and 4-bromobiphenyl (0.167 g, 0.717 mmol, 1.00 equiv) in toluene (4 mL) was added bis(cyclooctadiene)nickel(0) (Ni(COD)$_2$, 0.200 g, 0.717 mmol, 1.00 equiv), and the mixture was stirred at room temperature for 2 h. Pentane (16 mL) was added to the mixtures and the resulting solid was collected on a frit. The solid was washed with pentane (3×5 mL) and dried in vacuo to afford 0.288 g of the title compound as an orange solid (99%). Anal: calcd for $C_{18}H_{25}BrN_2Ni$: C, 52.99; H, 6.18; N, 6.87; found: C, 52.69; H, 6.16; N, 6.84.

Synthesis of Nickel(II) Aryl Complex (1a)

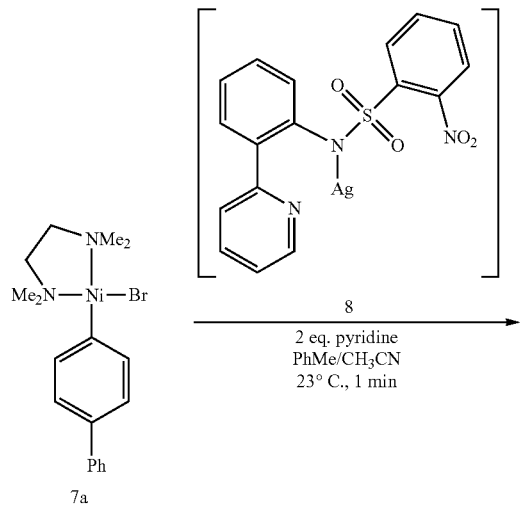

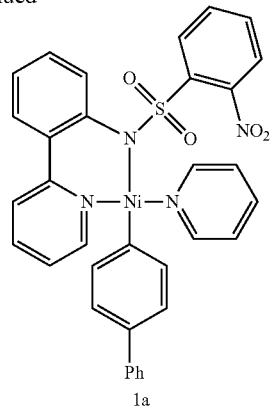

To (2-(2-Pyridinyl)phenyl-2-nitrobenzenesulfonamide)silver(I) (8) (0.227 g, 0.490 mmol, 1.00 equiv) and nickel(II) aryl bromide complex (7a) (0.200 g, 0.490 mmol, 1.00 equiv) in a 20 mL vial was added an toluene solution (4 mL) that contained pyridine (78.0 mg, 79.0 µL, 0.980 mmol, 2.00 equiv) at 23 °C., followed by addition of acetonitrile (1 mL). After stirring for 1 min at 23, the solution was filtered through a glass frit and the filtered cake was extracted further with dichloromethane (3×5 mL). The combined filtrate was concentrated in vacuo and the resulting residue was redissolved in dichloromethane (8 mL) and the solution was filtered through a pad of Celite and the filtrate was concentrated in vacuo. The resulting residue was recrytallized by dissolving the solid in $CH_2Cl_2$ (3 mL) and layering with pentane (17 mL). After one hour, the solid was collected by filtration to afford 0.256 g of the title compound as a yellow solid (81%). NMR Spectroscopy: 1H NMR (500 MHz, CDCl$_3$, δ): 9.17 (d, J=5.4 Hz, 2H), 8.25 (d, J=5.4 Hz, 1H), 7.57-7.47 (m, 6H), 7.43-7.36 (m, ), 7.32-7.28 (m, 3H), 7.21-6.97 (m, 10H), 6.61-6.59 (m, 1H). $^{13}$C NMR (125 MHz, CDCl$_3$, δ): 156.0, 154.9, 152.7, 151.4, 147.0, 141.6, 141.2, 137.2, 136.7, 136.5, 135.8, 135.6, 135.5, 131.6, 130.4, 130.2, 129.9, 128.7, 128.6, 128.3, 126.6, 126.4, 124.4, 124.3, 124.2, 122.8, 122.6, 121.8. Anal: calcd for $C_{34}H_{26}N_4NiO_4S$: C, 63.28; H, 4.06; N, 8.68; found: C, 63.02; H, 4.31; N, 8.48.

Synthesis of Nickel(II) Aryl Bromide Complex (7b)

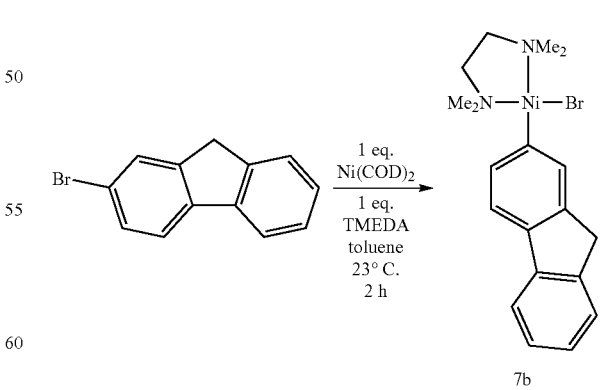

To a solution of TMEDA (0.133 mL, 0.896 mmol, 1.00 equiv) and 2-bromofluorene (0.220 g, 0.896 mmol, 1.00 equiv) in toluene (4 mL) was added bis(cyclooctadiene)nickel(0) (Ni(COD)$_2$, 0.250 g, 0.896 mmol, 1.00 equiv), and the mixture was stirred at room temperature for 2 h. Pentane (16 mL) was added to the mixtures and the resulting solid was collected on a frit. The solid was washed with pentane (3×5 mL) and dried in vacuo to afford 0.348 g of the title compound as a pink solid (92%). Anal: calcd for $C_{19}H_{25}BrN_2Ni$: C, 54.33; H, 6.00; N, 6.67; found: C, 53.98; H, 5.85; N, 6.56.

Synthesis of Nickel aAyl Complex (1b)

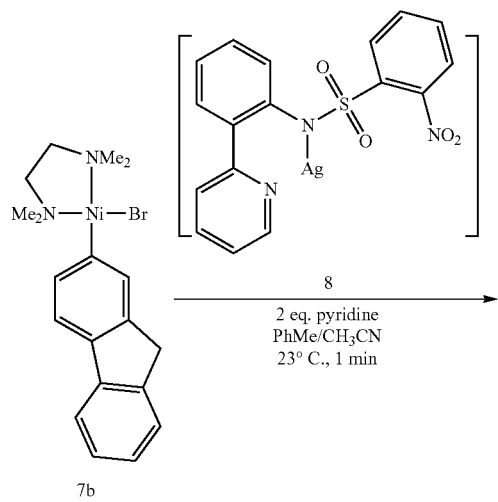

To (2-(2-Pyridinyl)phenyl-2-nitrobenzenesulfonamide)silver(I) (8) (0.110 g, 0.238 mmol, 1.00 equiv) and nickel(II) aryl bromide complex (7b) (0.100 g, 0.238 mmol, 1.00 equiv) in a 20 mL vial was added an toluene solution (4 mL) that contained pyridine (37.7 mg, 38.4 μL, 0.476 mmol, 2.00 equiv) at 23 ° C., followed by addition of acetonitrile (0.5 mL). After stirring for 1 min at 23, the solution was filtered through a glass frit and the filtered cake was extracted further with dichloromethane (3×3 mL). The combined filtrate was concentrated in vacuo and the resulting residue was purified by chromatography on silica gel eluting with hexanes/EtOAc 1:2 (v/v) and recrystallized with $CH_2Cl_2$/pentane and recrystallized with $CH_2Cl_2$/pentane to afford 0.148 g of the title compound as a yellow solid (95%). Rf=0.53 (hexanes/EtOAc 1:2 (v/v)). NMR Spectroscopy: $^1H$ NMR (500 MHz, $CDCl_3$, 23 ° C., δ): 9.18 (d, J=5.3 Hz, 2H), 8.24 (d, J=6.4 Hz, 1H), 7.65 (s, 1H), 7.58-7.46 (m, 6H), 7.40-7.37 (m, 2H), 7.29-7.21 (m, 3H), 7.16-7.07 (m, 6H), 7.02-6.97 (m, 2H), 6.57-6.54 (m, J=6.3, 1H), 3.72-3.58 (m, 2H). $^{13}C$ NMR (125 MHz, $CDCl_3$, 23 ° C., δ): 156.0, 155.2, 152.6, 151.4, 147.0, 142.6, 142.2, 141.3, 141.0, 137.1, 137.1, 136.7, 136.6, 135.6, 133.0, 131.8, 131.6, 130.4, 130.2, 129.9, 128.7, 128.3, 126.5, 125.6, 124.9, 124.4, 124.1, 122.8, 122.7, 121.7, 118.9, 117.1, 36.4. Anal: calcd for $C_{35}H_{26}N_4NiO_4S \cdot (CH_2Cl_2)_{0.1}$: C, 63.31; H, 3.97; N, 8.41; found: C, 63.04; H, 4.18; N, 8.36.

Synthesis of Nickel(II) Aryl Bromide Complex (7c)

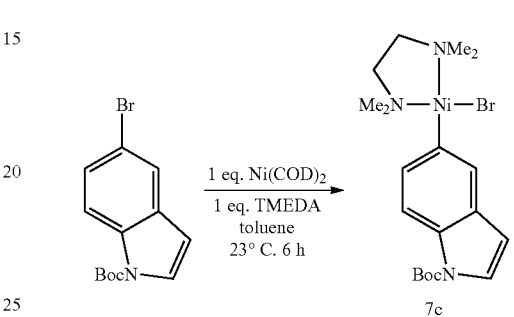

To a solution of TMEDA (0.157 mL, 1.05 mmol, 1.00 equiv) and tert-butyl 5-bromoindole-1-carboxylate (0.311 g, 1.05 mmol, 1.00 equiv) in toluene (5 mL) was added bis(cyclooctadiene)nickel(0) ($Ni(COD)_2$, 0.293 g, 1.05 mmol, 1.00 equiv), and the mixture was stirred at room temperature for 3 h. Pentane (16 mL) was added to the mixtures and the resulting solid was collected on a frit. The solid was washed with pentane (3×5 mL) and dried in vacuo to afford 0.491 g of the title compound as a peach solid (99%). Anal: calcd for $C_{19}H_{30}BrN_3NiO_2$: C, 48.44; H, 6.42; N, 8.92; found: C, 48.14; H, 6.22; N, 8.84.

Synthesis of Nickel(II) Aryl Complex (1c)

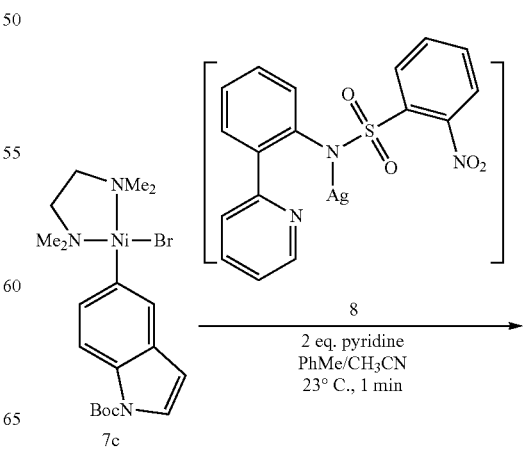

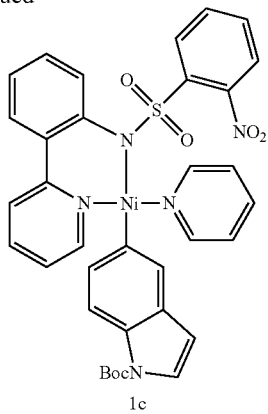

1c

Figure 1B:
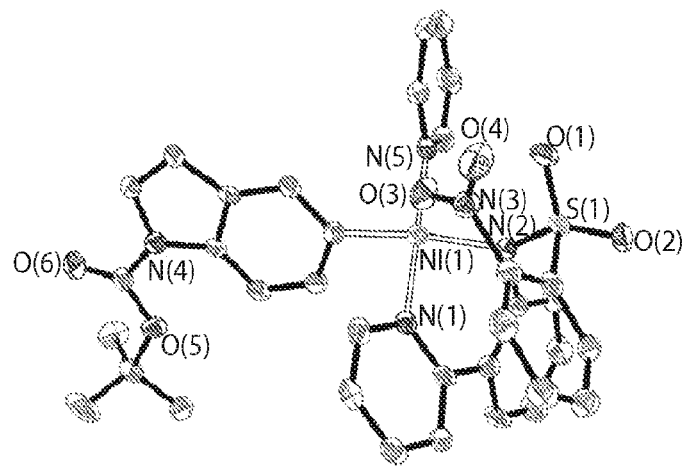
FIG. 1B shows additional perspective views where atoms are depicted with 50% probability displacement.
Figure 1B:
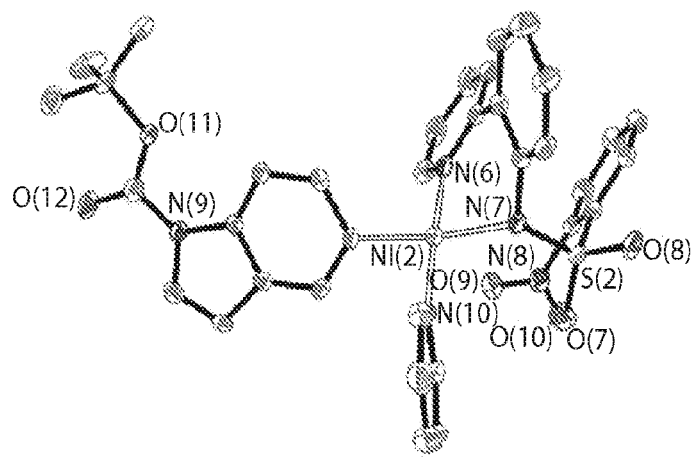

To (2-(2-Pyridinyl)phenyl-2-nitrobenzenesulfonamide)silver(I) (8) (0.0980 g, 0.212 mmol, 1.00 equiv) and nickel(II) aryl bromide complex (7c) (0.100 g, 0.212 mmol, 1.00 equiv) in a 20 mL vial was added an toluene solution (3 mL) that contained pyridine (33.6 mg, 34.2 μL, 0.425 mmol, 2.00 equiv) at 23° C., followed by addition of acetonitrile (0.5 mL). After stirring for 1 min at 23, the solution was filtered through a glass frit and the filtered cake was extracted further with dichloromethane (3×3 mL). The combined filtrate was concentrated in vacuo and the resulting residue was purified by chromatography on silica gel eluting with hexanes/EtOAc 1:2 (v/v) and recrystallized with $CH_2Cl_2$/pentane to afford 0.140 g of the title compound as a yellow solid (93%). Rf=0.53 (hexanes/EtOAc 1:2 (v/v)). NMR Spectroscopy: $^1$H NMR (500 MHz, $CDCl_3$, 23° C., δ): 9.10 (d, J=4.3 Hz, 2H), 8.16 (d, J=5.3 Hz, 1H), 7.59-7.39 (m, 6H), 7.33-7.29 (m, 2H), 7.21-7.18 (m, 2H), 7.09-7.00 (m, 5H), 6.93-6.91 (m, 2H), 6.48-6.47 (m, 1H), 6.23 (d, J=4.3, 1H), 1.50 (s, 9H). $^{13}$C NMR (125 MHz, $CDCl_3$, 23° C., δ): 156.0, 152.7, 151.5, 150.1, 147.0, 146.8, 141.3, 137.0, 136.6, 136.6, 135.7, 131.6, 130.7, 130.4, 130.1, 129.9, 129.3, 128.8, 128.3, 126.7, 124.4, 124.3, 124.1, 122.8, 122.6, 121.7, 112.6, 83.1, 28.0. Anal: calcd for $C_{35}H_{31}N_5NiO_6S\cdot(CH_2Cl_2)_{0-1}$: C, 58.81; H, 4.39; N, 9.77; found: C, 58.49; H, 4.39; N, 9.81. X-ray quality crystals were obtained from 2 mL $CH_2Cl_2$ solution that contained 10.0 mg of the title compound slowly layered with 8.0 mL pentane at 23° C. (See FIG. 1)

Synthesis of Nickel(II) Aryl Bromide Complex (7d)

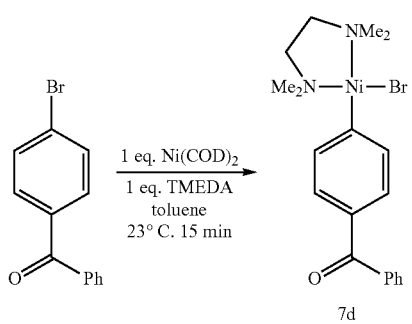

7d

To a solution of TMEDA (0.107 mL, 0.717 mmol, 1.00 equiv) and 4-bromobenzophenone (0.187 g, 0.717 mmol, 1.00 equiv) in toluene (4 mL) was added bis(cyclooctadiene)nickel(O) (Ni(COD)$_2$, 0.200 g, 0.717 mmol, 1.00 equiv), and the mixture was stirred at room temperature for 15 min. Pentane (16 mL) was added to the mixtures and the resulting solid was collected on a frit. The solid was washed with pentane (3×5 mL) and dried in vacuo to afford 0.305 g of the title compound as an orange solid (98%). Anal: calcd for $C_{19}H_{25}BrN_2NiO\cdot(PhMe)_{0.1}$: C, 53.15; H, 5.84; N, 6.29; found: C, 53.41; H, 5.84; N, 6.18.

Synthesis of Nickel(II) Aryl Complex (1d)

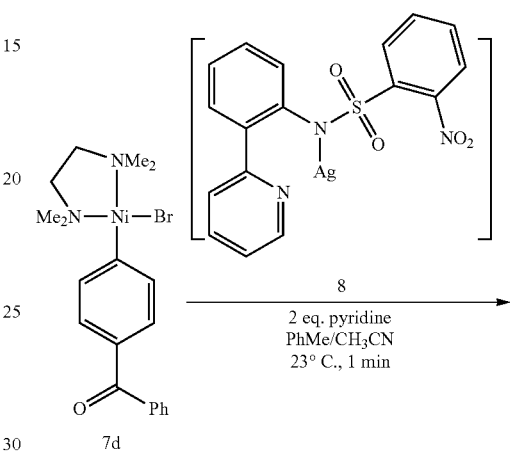

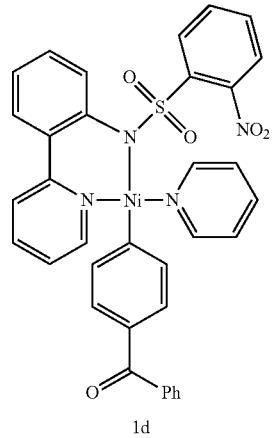

1d

To (2-(2-Pyridinyl)phenyl-2-nitrobenzenesulfonamide)silver(I) (8) (0.212 g, 0.459 mmol, 1.00 equiv) and nickel(II) aryl bromide complex (7d) (0.200 g, 0.459 mmol, 1.00 equiv) in a 20 mL vial was added an toluene solution (4 mL) that contained pyridine (78.0 mg, 79.0 μL, 0.980 mmol, 2.00 equiv) at 23° C., followed by addition of acetonitrile (1.0 mL). After stirring for 1 min at 23, the solution was filtered through a glass frit and the filtered cake was extracted further with dichloromethane (3×5 mL). The combined filtrate was concentrated in vacuo and the resulting residue was purified by chromatography on silica gel eluting with hexanes/EtOAc 1:2 (v/v) and recrystallized with $CH_2Cl_2$/pentane to afford 0.138 g of the title compound as a yellow solid (45%).

Rf=0.41 (hexanes/EtOAc 1:2 (v/v)). NMR Spectroscopy: $^1$H NMR (500 MHz, $CD_2Cl_2$, 23° C., δ): 9.13 (d, J=5.3 Hz, 2H), 8.17 (d, J=5.3 Hz, 1H), 7.69 (d, J=7.6 Hz, 2H), 7.66-7.56 (m, 5H), 7.52-7.49 (m, 1H), 7.41-7.35 (m, 5H), 7.26-7.23 (m, 2H), 7.19-7.16 (m, 4H), 7.08 (d, J=8.3 Hz, 1H), 7.02 (s, br, 2H), 6.67-6.64 (m, 1H). $^{13}$C NMR (125 MHz, $CD_2Cl_2$, 23°

C., δ): 197.1, 169.1, 156.2, 152.5, 151.5, 147.3, 141.2, 138.8, 138.0, 137.4, 136.6, 136.0, 135.6, 132.8, 131.9, 131.8, 130.9, 130.8, 130.3, 130.0, 128.8, 128.7, 128.3, 126.9, 124.8, 124.6, 123.4, 123.0, 122.4. Anal: calcd for $C_{35}H_{26}N_4NiO_5S \cdot (CH_2Cl_2)_{0.15}$: C, 61.53; H, 3.86; N, 8.17; found: C, 61.19; H, 4.20; N, 8.58.

Synthesis of Nickel(II) Aryl Bromide Complex (7e)

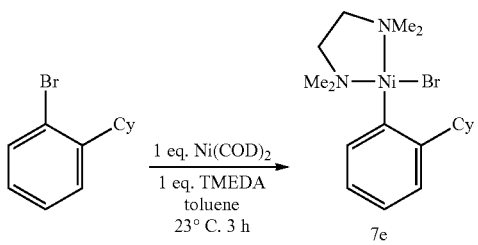

To a solution of TMEDA (0.107 mL, 0.717 mmol, 1.00 equiv) and 1-bromo-2-cyclohexylbenzene (0.171 g, 0.717 mmol, 1.00 equiv) in toluene (4 mL) was added bis(cyclooctadiene)nickel(0) (Ni(COD)$_2$, 0.200 g, 0.717 mmol, 1.00 equiv), and the mixture was stirred at room temperature for 3 h. Pentane (16 mL) was added to the mixtures and the resulting solid was collected on a frit. The solid was washed with pentane (3×5 mL) and dried in vacuo to afford 0.208 g of the title compound as a pink solid (70%). Anal: calcd for $C_{18}H_{31}BrN_2Ni$: C, 52.21; H, 7.55; N, 6.77; found: C, 51.87; H, 7.43; N, 6.73.

Synthesis of Nickel(II) Aryl Complex (1e)

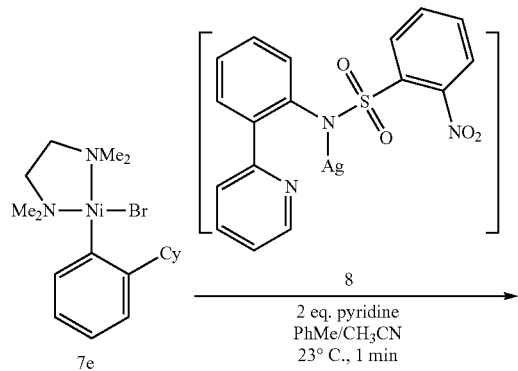

To (2-(2-Pyridinyl)phenyl-2-nitrobenzenesulfonamide) silver(I) (8) (0.223 g, 0.483 mmol, 1.00 equiv) and nickel(II) aryl bromide complex (7e) (0.200 g, 0.483 mmol, 1.00 equiv) in a 20 mL vial was added an toluene solution (4 mL) that contained pyridine (76.0 mg, 78.0 μL, 0.966 mmol, 2.00 equiv) at 23 ° C., followed by addition of acetonitrile (1.0 mL). After stirring for 1 min at 23, the solution was filtered through a glass frit and the filtered cake was extracted further with dichloromethane (3×5 mL). The combined filtrate was concentrated in vacuo and the resulting residue was purified by chromatography on silica gel eluting with hexanes/EtOAc 1:2 (v/v) and recrystallized with CH$_2$Cl$_2$/pentane to afford 0.146 g of the title compound as a yellow solid (46%). Rf=0.66 (hexanes/EtOAc 1:2 (v/v)). NMR Spectroscopy: $^1$H NMR (500 MHz, CDCl$_3$, 23 ° C., δ): 9.09 (d, J=5.3 Hz, 2H), 8.33 (d, J=5.3 Hz, 1H), 8.18 (d, J=7.5 Hz, 1H), 7.62-7.46 (m, 4H), 7.40-7.37 (m, 1H), 7.29-7.26 (m, 1H), 7.15-7.09 (m, 5H), 7.00-6.93 (m, 3H), 6.73-6.70 (m, 1H), 6.59-6.56 (m, 1H), 6.49 (d, J=7.4, 1H), 4.86-4.82 (m, 1H), 1.73-1.01 (m, 10H). $^{13}$C NMR (125, CDCl$_3$, 23 ° C., δ): 156.2, 156.1, 153.1, 151.8, 151.2, 147.0, 141.2, 137.0, 136.6, 135.4, 134.2, 131.8, 130.3, 130.1, 129.8, 128.9, 128.6, 125.1, 124.1, 124.0, 123.0, 122.7, 122.5, 121.7, 49.0, 35.5, 34.5, 27.4, 26.9, 26.4. Anal: calcd for $C_{34}H_{32}N_4NiO_4S \cdot (CH_2Cl_2)_{0.1}$: C, 62.07; H, 4.92; N, 8.49; found: C, 61.91; H, 4.92; N, 8.69.

4-bromophenethyl Benzoate (S3)

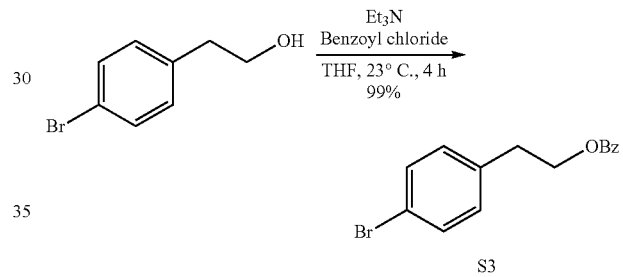

To a mixture of 2-(4-bromophenyl)ethanol (1.00 g, 4.97 mmol, 1.00 equiv) and Et$_3$N (0.763 ml, 0.554 g, 5.47 mmol, 1.10 equiv) in a round-bottom flask in THF (20 ml) was added benzoyl chloride (0.589 mL, 0.713 g, 5.07 mmol, 1.02 equiv). The reaction mixture was stirring for 4 h at 23 ° C. and concentrated in vacuo. The residue was purified by chromatography on silica gel eluting with hexanes/EtOAc 1:1 (v/v) to afford 1.50 g of the title compound as a colorless solid (99%). Rf=0.7 (hexanes/EtOAc 1:1 (v/v)). NMR Spectroscopy: $^1$H NMR (500 MHz, CDCl$_3$, 23 ° C., δ): 8.00 (d, J=7.2 Hz, 1H), 7.58-7.54 (m, 1H), 7.45-7.42 (m, 4H), 7.16 (d, J=8.4 Hz, 2H), 4.51 (t, J=6.4 Hz, 2H), 3.04 (t, J=6.4 Hz, 2H). $^{13}$C NMR (125 MHz, CDCl$_3$, 23 ° C., δ): 166.6, 137.1, 133.1, 131.8, 130.8, 130.3, 129.7, 128.5, 120.6, 65.2, 34.8.

Synthesis of Nickel(II) Aryl Bromide Complex (7f)

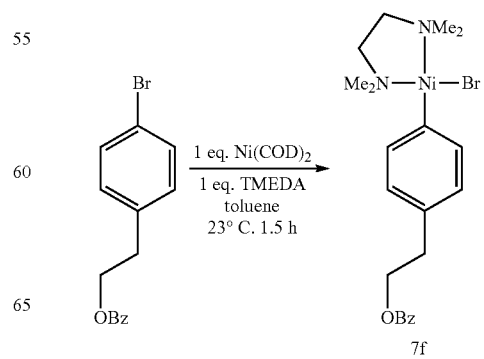

To a solution of TMEDA (0.107 mL, 0.717 mmol, 1.00 equiv) and 4-bromophenethyl benzoate (0.219 g, 0.717 mmol, 1.00 equiv) in toluene (4 mL) was added bis(cyclooctadiene)nickel(0) (Ni(COD)$_2$, 0.200 g, 0.717 mmol, 1.00 equiv), and the mixture was stirred at room temperature for 1.5 h. Pentane (16 mL) was added to the mixtures and the resulting solid was collected on a frit. The solid was washed with pentane (3×5 mL) and dried in vacuo to afford 0.208 g of the title compound as an orange-pink solid (90%). Anal: calcd for C$_{21}$H$_{29}$BrN$_2$NiO$_2$: C, 52.54; H, 6.09; N, 5.84; found: C, 52.81; H, 5.95; N, 5.53.

Synthesis of Nickel(II) Aryl Complex (1f)

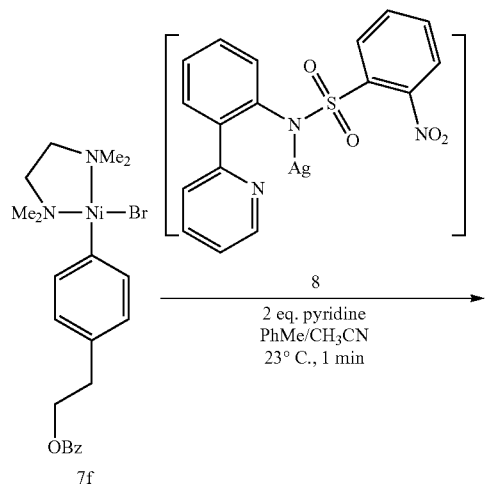

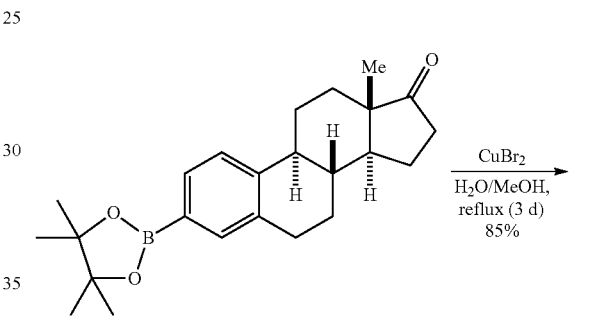

To (2-(2-Pyridinyl)phenyl-2-nitrobenzenesulfonamide)silver(I) (8) (0.193 g, 0.417 mmol, 1.00 equiv) and nickel(II) aryl bromide complex (7f) (0.200 g, 0.417 mmol, 1.00 equiv) in a 20 mL vial was added an toluene solution (4 mL) that contained pyridine (65.9 mg, 67.1 µL, 0.833 mmol, 2.00 equiv) at 23° C., followed by addition of acetonitrile (1.0 mL). After stirring for 1 min at 23, the solution was filtered through a glass frit and the filtered cake was extracted further with dichloromethane (3×5 mL). The combined filtrate was concentrated in vacuo and the resulting residue was purified by chromatography on silica gel eluting with hexanes/EtOAc 1:2 (v/v) to afford 0.152 g of the title compound as a yellow solid (51%).

Rf=0.52 (hexanes/EtOAc 1:2 (v/v)). NMR Spectroscopy: $^1$H NMR (400 MHz, CDCl$_3$, 23° C., δ): 9.13 (d, J=5.6 Hz, 2H), 8.17 (d, J=5.2 Hz, 1H), 7.94 (d, J=8.0 Hz, 2H), 7.55-7.45 (m, 5H), 7.41-7.28 (m, 6H), 7.17-7.07 (m, 5H), 7.01-6.97 (m, 2H), 6.68 (d, J =7.6, 2H), 6.57- 6.54 (m, 1H), 4.32 (t, J=7.2 Hz, 2H), 2.81 (t, J=7.2 Hz, 2H). $^{13}$C NMR (125 MHz CDCl$_3$ 23° C., δ): 166.7, 156.0, 152.6, 152.3, 151.5, 147.1, 141.3, 137.1, 136.7, 136.6, 136.3, 135.6, 135.5, 132.9, 131.8, 131.6, 130.6, 130.4, 130.1, 129.8, 129.6, 128.8, 128.5, 128.4, 128.3, 127.2, 126.7, 124.3, 124.1, 122.8, 122.6, 121.7, 66.1, 34.6. Anal: calcd for C$_{37}$H$_{30}$N$_4$NiO$_6$S: C, 61.94; H, 4.21; N, 7.81; found: C, 61.58; H, 4.16; N, 7.47.

Synthesis of 3-deoxy-3-bromoestrone (S4)

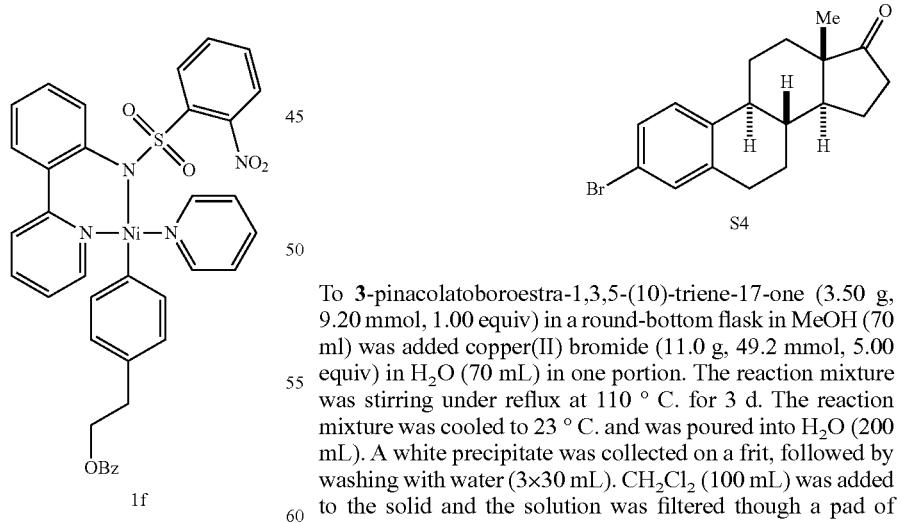

To 3-pinacolatoboroestra-1,3,5-(10)-triene-17-one (3.50 g, 9.20 mmol, 1.00 equiv) in a round-bottom flask in MeOH (70 ml) was added copper(II) bromide (11.0 g, 49.2 mmol, 5.00 equiv) in H$_2$O (70 mL) in one portion. The reaction mixture was stirring under reflux at 110° C. for 3 d. The reaction mixture was cooled to 23° C. and was poured into H$_2$O (200 mL). A white precipitate was collected on a frit, followed by washing with water (3×30 mL). CH$_2$Cl$_2$ (100 mL) was added to the solid and the solution was filtered though a pad of Celite. The filtrate was concentrated, triturated with Et$_2$O (3×5 mL) and dried to afford 2.60 g of the title compound as a colorless solid (85% yield).

NMR Spectroscopy: $^1$H NMR (500 MHz, CDCl$_3$, 23° C., δ): 7.28 (d, J=8.6 Hz, 1H), 7.26 (s, 1H), 7.17 (d, J=8.6 Hz, 1H), 2.92-2.90 (m, 2H), 2.56-2.50 (m, 2H), 2.28-2.23 (m, 1H), 2.21-1.98 (m, 4H), 1.69-1.41 (m, 6H), 0.93(s, 3 H). $^{13}$C NMR (125 MHz, CDCl$_3$, 23 ° C., δ): 220.7, 139.0, 138.9, 131.8, 128.8, 127.3, 119.7, 50.5, 48.0, 44.2, 38.0, 35.9, 31.6, 29.3, 26.4, 25.8, 21.7, 13.9.

Synthesis of Nickel(II) Aryl Bromide Complex (7g)

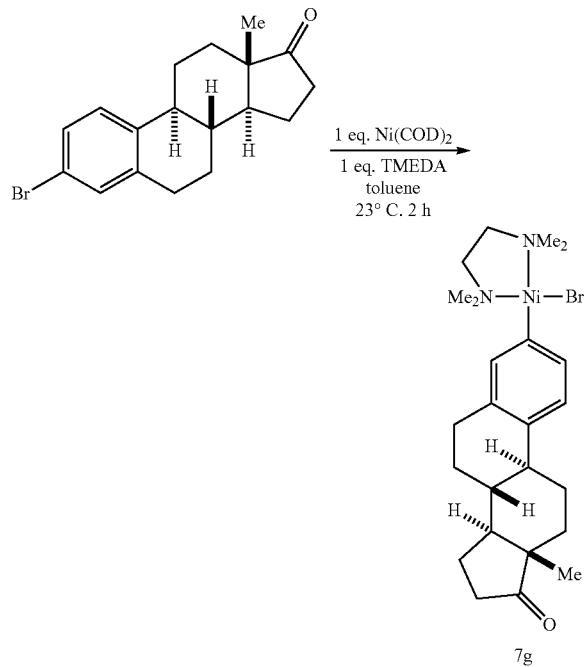

To a solution of TMEDA (0.134 mL, 0.896 mmol, 1.00 equiv) and 3-deoxy-3-bromoestrone (0.299 g, 0.896 mmol, 1.00 equiv) in toluene (5 mL) was added bis(cyclooctadiene)nickel(0) (Ni(COD)$_2$, 0.200 g, 0.896 mmol, 1.00 equiv), and the mixture was stirred at room temperature for 2 h. Pentane (16 mL) was added to the mixtures and the resulting solid was collected on a frit. The solid was washed with pentane (3×5 mL) and dried in vacuo to afford 0.406 g of the title compound as a peach solid (89%). Anal: calcd for C$_{24}$H$_{37}$BrN$_2$NiO: C, 56.73; H, 7.34; N, 5.51; found: C, 52.92; H, 6.91; N, 5.50. Numerous attempts were made to get elemental analysis data satisfactory one was not obtained. However, purification by chromatography on next step enables to access pure 1 g.

Synthesis of Nickel(II) Aryl Complex (1g)

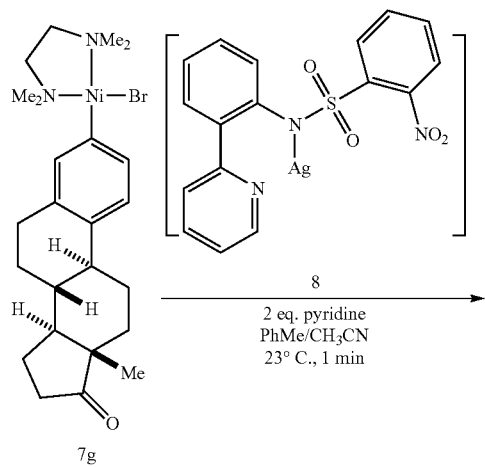

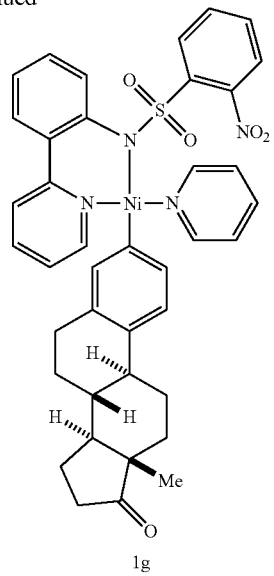

To (2-(2-Pyridinyl)phenyl-2-nitrobenzenesulfonamide)silver(I) (8) (0.193 g, 0.417 mmol, 1.00 equiv) and nickel(II) aryl bromide complex (7g) (0.200 g, 0.417 mmol, 1.00 equiv) in a 20 mL vial was added an toluene solution (4 mL) that contained pyridine (65.9 mg, 67.1 µL, 0.833 mmol, 2.00 equiv) at 23 ° C., followed by addition of acetonitrile (1.0 mL). After stirring for 1 min at 23, the solution was filtered through a glass frit and the filtered cake was extracted further with dichloromethane (3×5 mL). The combined filtrate was concentrated in vacuo and the resulting residue was purified by chromatography on silica gel eluting with hexanes/EtOAc 1:2 (v/v) and recrystallized with CH$_2$Cl$_2$/pentane to afford 0.152 g of the title compound as a yellow solid (51%). Rf=0.35 (hexanes/EtOAc 1:2 (v/v)). NMR Spectroscopy: $^1$H NMR (500 MHz, CDCl$_3$, 23 ° C., δ): 9.14 (d, J=4.9 Hz, 2H), 8.28-8.26 (m, 1H), 7.54-7.45 (m, 4H), 7.36-7.28 (m, 2H), 7.16-6.97 (m, 9H), 6.66-6.62 (m, 2H), 2.77-2.60 (m, 2H), 2.47-2.41 (m, 2H), 2.21-1.85 (m, 6H), 1.55-1.27 (4H), 0.82 (m, 3H). $^{13}$C NMR (125 MHz CDCl$_3$, 23 ° C., δ): 221.3, 156.0, 152.7, 152.7, 151.5, 150.7, 150.6, 147.0, 141.3, 137.0, 136.6, 135.9, 135.8, 135.7, 133.9, 133.8, 133.7, 133.1, 132.9, 131.6, 131.3, 130.5, 130.4, 130.1, 129.7, 128.8, 128.4, 128.3, 124.4, 124.2, 124.1, 122.8, 122.7, 122.7, 122.6, 121.7, 50.7, 48.2, 44.2, 44.2, 38.4, 38.3, 36.0, 31.8, 29.5, 29.5, 26.9, 25.6, 25.6, 21.7, 14.0. Anal: calcd for C$_{40}$H$_{38}$N$_4$NiO$_5$S·(CH$_2$Cl$_2$)$_{0.1}$: C, 63.88; H, 5.11; N, 7.43; found: C, 63.62; H, 5.26; N, 7.06.

5-bromo-2-(cyclopropylmethoxy)benzaldehyde (S5)

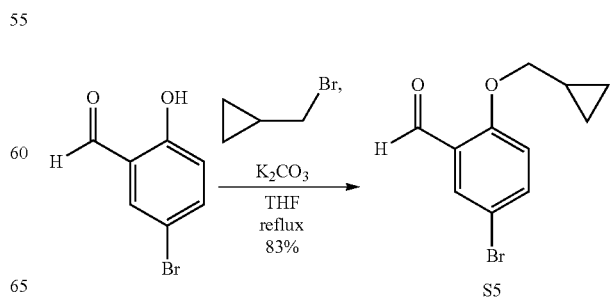

To 5-bromo-2-hydroxybenzaldehyde (1.00 g, 4.97 mmol, 1.00 equiv) and $K_2CO_3$ (3.44 g, 24.9 mmol, 5.00 equiv) in THF (10 mL) in an oven-dried round-bottom flask fitted with a reflux condenser under a $N_2$ atmosphere at 23 °C. was added (bromomethyl)cyclopropane (1.01 g, 0.724 mL, 7.46 mmol, 1.50 equiv). The reaction mixture was warmed in an oil heating bath at a temperature of 70 °C. and heated at reflux with vigorous stirring for 40 hours. The reaction mixture was cooled to 23 °C. and poured into $H_2O$ (30 mL) in a separatory funnel. $CHCl_3$ (30 mL) was added, the funnel was shaken and the organic phase collected. The aqueous phase was then extracted with $CHCl_3$ (2×30 mL). The combined organic phases were washed with brine (30 mL), dried with $Na_2SO_4$, and concentrated in vacuo. The residue was purified by chromatography on silica gel, eluting with 2-7% EtOAc in hexanes (v/v) to afford 1.05 g of the title compound as a colorless solid (83% yield). Rf=0.30 (hexanes/EtOAc 19:1 (v/v)). NMR Spectroscopy: $^1$H NMR (600 MHz, $CDCl_3$, 23 °C., δ): 10.45 (s, 1H), 7.91 (d, J=2.5 Hz, 1H), 7.58 (dd, J=8.9, 2.6 Hz, 1H), 6.84 (d, J=8.9 Hz, 1H), 3.91 (d, J=7.2 Hz, 2H), 1.32-1.26 (m, 1H), 0.71-0.63 (m, 2H), 0.41-0.34 (m, 2H). $^{13}$C NMR (125 MHz, $CDCl_3$, 23 °C., δ): 188.7, 160.5, 138.3, 130.9, 126.5, 115.0, 113.5, 73.9, 10.1, 3.4. HRMS-FIA (m/z): calcd for $C_{11}H_{11}BrNaO_2[M+Na]^+$, 276.9840; found, 276.9820.

(E)-ethyl 3-(5-bromo-2-(cyclopropylmethoxy)phenyl)acrylate (S6)

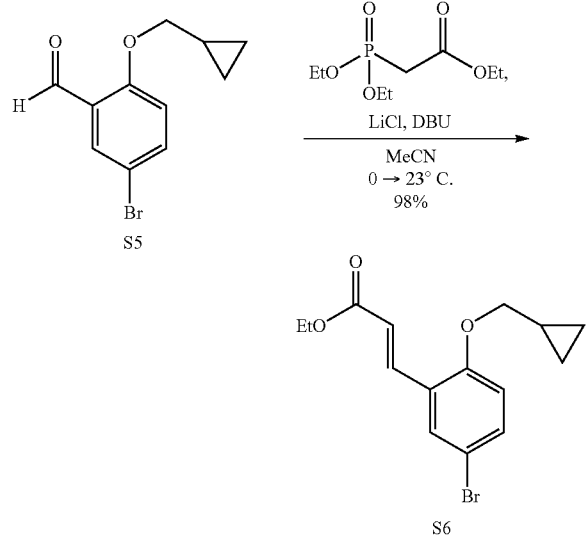

To 5-bromo-2-(cyclopropylmethoxy)benzaldehyde (S5) (3.10 g, 12.2 mmol, 1.00 equiv) and LiCl (0.541 g, 12.8 mmol, 1.05 equiv) in MeCN (45 mL) in a round-bottom flask under a $N_2$ atmosphere at 0 °C. was added triethyl phosphonoacetate (3.00 g, 2.68 mL, 13.4 mmol, 1.10 equiv) and 1,8-diazabicycloundec-7-ene (DBU) (2.04 g, 2.02 mL, 13.4 mmol, 1.10 equiv). Upon the addition of DBU, the reaction mixture turned yellow. The reaction mixture was warmed to 23 °C. and stirred for 15 hours. The reaction mixture was poured into $H_2O$ (75 mL) in a separatory funnel. $CHCl_3$ (75 mL) was added and the funnel was shaken and the organic phase collected. The aqueous phase was extracted from with $CHCl_3$ (2×50 mL). All organic phases were combined and washed with brine (50 mL), dried with $Na_2SO_4$, and concentrated in vacuo. The residue was purified by chromatography on silica gel, eluting with 5-10% EtOAc in hexanes (v/v) to afford 3.89 g of the title compound as a colorless solid (98% yield). Rf=0.25 (hexanes/EtOAc 19:1 (v/v)). NMR Spectroscopy: $^1$H NMR (500 MHz, $CDCl_3$, 23 °C., δ): 7.93 (d, J=16.1 Hz, 1H), 7.60 (d, J=2.4 Hz, 1H), 7.37 (dd, J=8.8, 2.5 Hz, 1H), 6.74 (d, 8.8 Hz, 1H), 6.53 (d, J=16.1 Hz, 1H), 4.26 (q, J=6.8 Hz, 2H), 3.84 (d, J=6.8 Hz, 2H), 1.34-1.25 (m, 4H), 0.70-0.61 (m, 2H), 0.40-0.31 (m, 2H). $^{13}$C NMR (125 MHz, $CDCl_3$, 23 °C., δ): 167.3, 156.9, 138.7, 133.7, 131.3, 125.9, 120.0, 114.4, 113.0, 73.9, 60.6, 14.4, 10.2, 3.4. HRMS-FIA (m/z): calcd for $C_{15}H_{18}BrO_3$ [M+]+, 325.0439; found, 325.0428.

(E)-3-(5-bromo-2-(cyclopropylmethoxy)phenyl)prop-2-en-1-ol (S7)

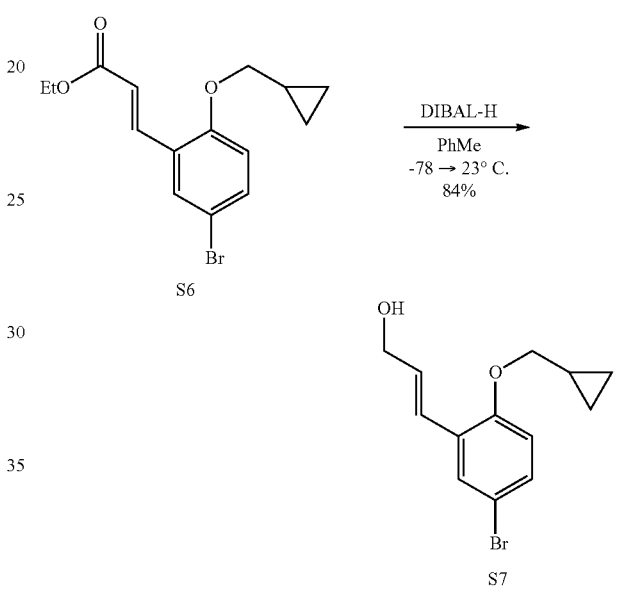

To (E)-ethyl 3-(5-bromo-2-(cyclopropylmethoxy)phenyl) acrylate (S6) (3.78 g, 11.6 mmol, 1.00 equiv) in PhMe (30 mL) in a flame-dried round-bottom flask under a $N_2$ atmosphere at −78 °C. was added a 1.0 M solution of diisobutylaluminum hydride (DIBAL-H) in PhMe (26 mL, 26 mmol, 2.2 equiv) in 6 portions dropwise every 10 minutes for 1 hour. The reaction was warmed to 0 °C. over 2 hours and then warmed to 23 °C. and stirred at this temperature for 1 hour. The reaction mixture was poured onto a concentrated aqueous Rochelle's salt (potassium sodium tartrate) solution (400 mL). EtOAc (400 mL) was added and the mixture was stirred for 3 hour until two liquid phases separated cleanly. The phases were partitioned and the aqueous phase was extracted from with EtOAc (300 mL). The organic phases were combined and washed with brine (200 mL), dried with $Na_2SO_4$, and concentrated in vacuo. The residue was purified by chromatography on silica gel, eluting with a gradient of 10-25% EtOAc in hexanes (v/v) to afford 2.77 g of the title compound as a colorless solid (84% yield). Rf=0.15 (hexanes/EtOAc 6:1 (v/v)). NMR Spectroscopy: $^1$H NMR (500 MHz, $CDCl_3$, 23 °C., δ): 7.53 (d, J=2.4 Hz, 1H), 7.26 (dd, J=8.8, 2.4 Hz, 1H), 6.88 (d, J=16.1 Hz, 1H), 6.69 (d, J=8.8 Hz, 1H), 6.39 (dt, J=16.1, 5.9 Hz, 1H), 4.33 (br dd, J=4.6, 4.6 Hz, 2H), 3.79 (d, J=6.8 Hz, 2H), 1.71 (br t, J=5.1 Hz, 1H), 1.31-1.23 (m, 1H), 0.68-0.58 (m, 2H), 0.38-0.30 (m, 2H). $^{13}$C NMR (125 MHz, $CDCl_3$, 23 °C., δ): 155.4, 131.2, 130.5, 129.7, 128.2, 125.0, 114.2, 113.2, 73.7, 64.1, 10.3, 3.4. HRMS-FIA (m/z): calcd for $C_{13}H_{15}BrNaO_2$ [M+Na]$^+$, 305.0153; found, 305.0123.

((1S,2S)-2-(5-bromo-2-(cyclopropylmethoxy)phenyl)cyclopropyl)methanol (S8)

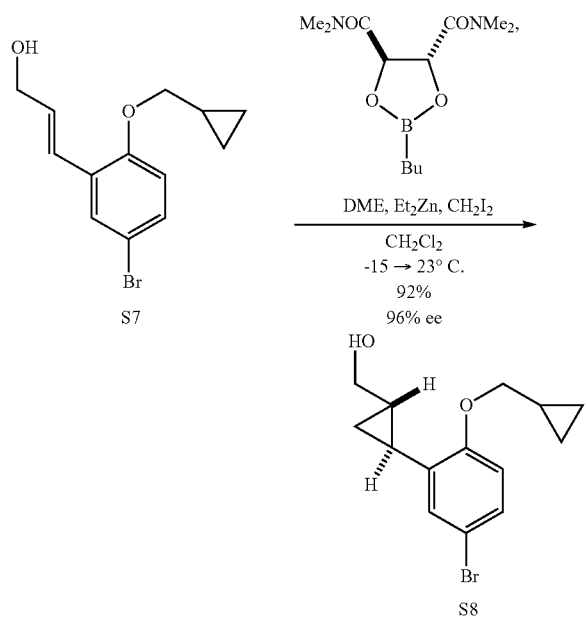

Figure 2A:
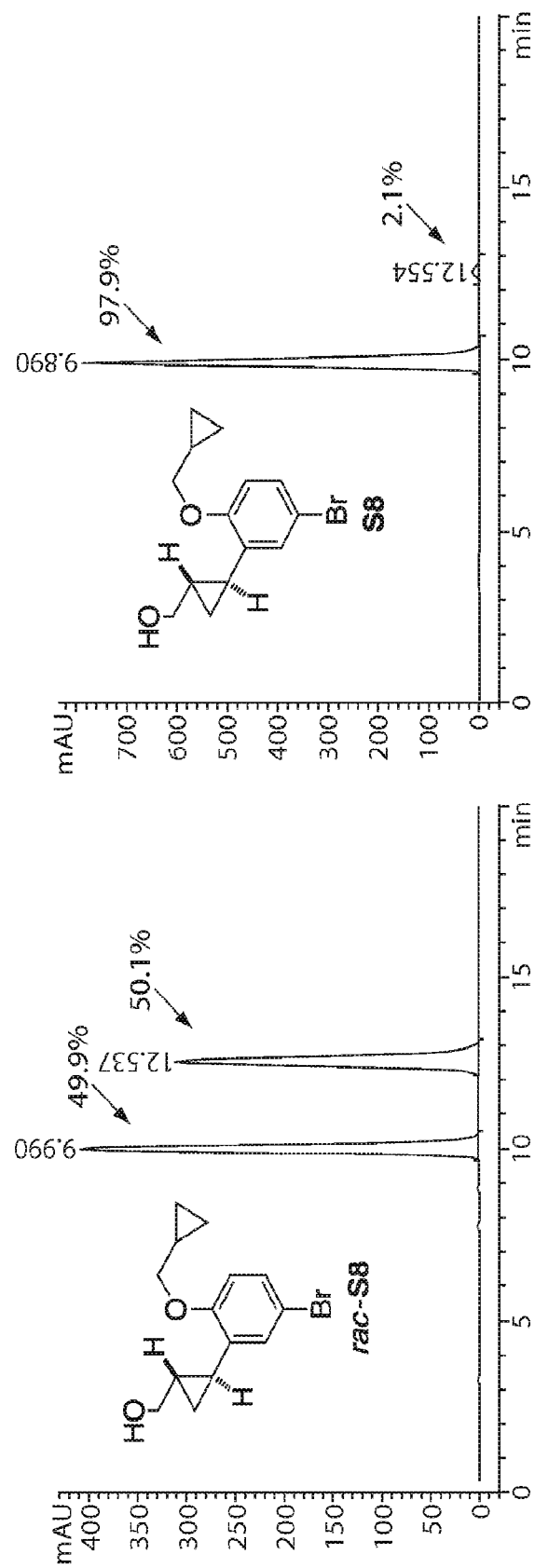
FIG. 2A shows the enantiodiscriminating HPLC trace of ((1S,2S)-2-(5-bromo-2-(cyclopropylmethoxy) phenyl)cyclopropyl) methanol (S8). HPLC method: Chiracel ODH column with 5% isopropanol/hexanes eluent for racemic S8 and enantioenriched S8. Percent of total integration listed for each peak.

Following a published procedure for asymmetric allylic cyclopropanation: To dimethoxyethane (DME) (1.39 g, 1.60 mL, 15.4 mmol, 1.90 equiv) in $CH_2Cl_2$ (50 mL) in a flame-dried round-bottom flask under a $N_2$ atmosphere cooled in an ethyleneglycol/$CO_2$ bath at −15 ° C. was added diethylzinc (2.01 g, 1.67 mL, 16.3 mmol, 2.00 equiv), while maintaining the bath temperature between −15 and −10 ° C. $CH_2I_2$ (8.70 g, 2.62 mL, 32.5 mmol, 4.00 equiv) was added dropwise over 20 minutes at −15 ° C. The reaction mixture was stirred at −15 ° C. for 10 minutes. A solution of (4R,5R)-2-butyl-N,N,N',N'-tetramethyl-1,3,2-dioxaborolane-4,5-dicarboxamide (2.63 g, 2.46 mL, 9.75 mmol, 1.20 equiv) in $CH_2Cl_2$ (10 mL) from a separate flame-dried round-bottom flask under a $N_2$ atmosphere was added over 5 minutes via syringe. A solution of (E)-3-(5-bromo-2-(cyclopropylmethoxy)phenyl)prop-2-en-1-ol (S7) (2.30 g, 8.12 mmol, 1.00 equiv) in $CH_2Cl_2$ (10 mL) from a separate flame-dried round-bottom flask under a $N_2$ atmosphere was added over 5 minutes via syringe. The reaction mixture was allowed to warm to 23 ° C. and stirred for 20 hours. Saturated aqueous $NH_4Cl$ solution (10 mL) and 1M HCl (50 mL) were added to the reaction mixture. The reaction mixture was transferred to a separatory funnel. Diethyl ether (200 mL) was added and the separatory funnel was shaken and the organic phase was separated. The aqueous phase was extracted from with diethyl ether (200 mL) and then again with diethyl ether (100 mL). The combined organic phases were transferred to an Erlenmeyer flask. 2 M NaOH solution (60 mL) and 30% $H_2O_2$ solution (15 mL) were added. The reaction mixture was stirred vigorously for 5 minutes. The reaction mixture was transferred into a separatory funnel and partitioned. The organic phase was washed with 1.0 M aqueous HCl (75 mL), saturated aqueous $Na_2CO_3$ solution (75 mL), saturated aqueous $NaHCO_3$ solution (75 mL) and brine (75 mL). The organic phase was dried with $MgSO_4$, and concentrated in vacuo. The residue was purified by chromatography on silica gel, eluting with a gradient of 10-30% EtOAc in hexanes (v/v) to afford 2.21 g of the title compound as a colorless oil (92% yield and 96% ee as determined on a Chiracel ODH column with 5% isopropanol/hexanes eluent (see FIG. 2A). Racemic S8 was synthesized using the above procedures omitting the addition of (4R,5R)-2-butyl-N,N,N',N'-tetramethyl-1,3,2-dioxaborolane-4,5-dicarboxamide. Absolute stereochemistry was assigned by analogy.

Rf=0.20 (hexanes/EtOAc 6:1 (v/v)). NMR Spectroscopy: $^1$H NMR (500 MHz, CDCl$_3$, 23 ° C., δ): 7.24 (dd, J=8.8, 2.4 Hz, 1H), 7.09 (d, J=2.4 Hz, 1H), 6.65 (d, J=8.8 Hz, 1H), 3.95 (ddd, J=10.7, 8.8, 4.9 Hz, 1H), 3.82 (d, J=7.3 Hz, 2H), 3.19 (ddd, J=10.7, 10.7, 2.0, 1H), 2.40 (dd, J=8.5, 2.0 Hz, 1H), 1.86 (ddd, J=8.5, 5.0, 5.0 Hz, 1H) 1.34-1.27 (m, 1H), 1.20-1.15 (m, 1H), 1.14-1.09 (m, 1H), 0.86 (ddd, J=9.0, 5.0, 5.0 Hz, 1H), 0.71-0.65 (m, 2H), 0.40-0.34 (m, 2H). $^{13}$C NMR (125 MHz, CDCl$_3$, 23 ° C., δ): 157.2, 132.4, 130.2, 129.9, 112.8, 112.6, 73.6, 67.3, 24.5, 17.2, 10.2, 9.9, 3.7, 3.2. HRMS FIA (m/z): calcd for $C_{14}H_{17}BrNaO_2$[M+Na]$^+$, 319.0310; found, 319.0327.

2-((1S,2S)-2-(azidomethyl)cyclopropyl)-4-bromo-1-(cyclopropylmethoxy)benzene (S9)

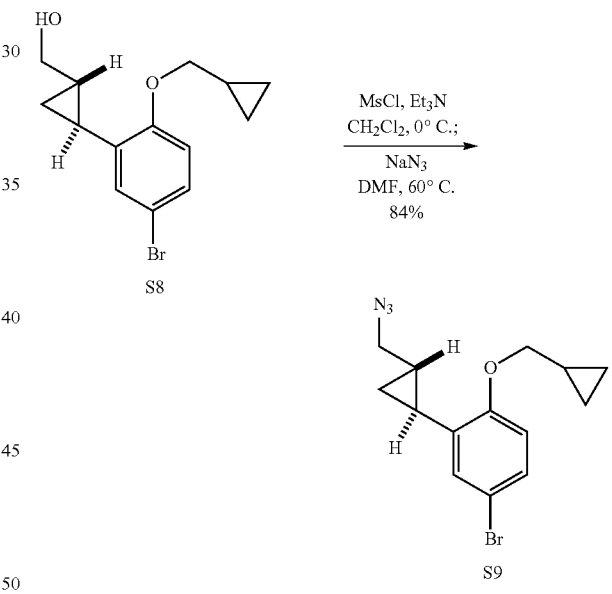

To ((1S,2S)-2-(5-bromo-2-(cyclopropylmethoxy)phenyl)cyclopropyl)methanol (S8) (2.15 g, 7.23 mmol, 1.00 equiv) in $CH_2Cl_2$ (30 mL) in an oven-dried round-bottom flask under a $N_2$ atmosphere at 0 ° C. was added Et$_3$N (2.20 g, 3.03 mL, 21.7 mmol, 3.00 equiv) and MsCl (1.66 g, 1.13 mL, 14.5 mmol, 2.00 equiv). The reaction mixture was stirred at 0 ° C. for 2 hours. The reaction mixture turned yellow and a precipitate formed. The reaction mixture was poured into a separatory funnel with saturated NH$_4$Cl solution (40 mL). The funnel was shaken and the organic phase collected. The aqueous phase was extracted from with diethyl ether (3×75 mL). The organic phases were combined and washed with saturated NaHCO$_3$ (100 mL) and brine (100 mL), dried with MgSO$_4$, and concentrated in vacuo. The residue was dissolved in DMF (30 mL) and NaN$_3$ (1.88 g, 28.9 mmol, 4.00 equiv) was added. The reaction mixture was heated at 60 ° C.

for 1 hour. The reaction mixture was cooled and poured into 60 mL of water. The reaction mixture was extracted from with diethyl ether (3×75 mL). The combined organic phases were washed with brine (100 mL), dried with MgSO$_4$, and concentrated in vacuo. The residue was purified by chromatography on silica gel, eluting with a gradient of 5-10% EtOAc in hexanes (v/v) to afford 1.95 g of the title compound as a colorless oil (84% yield). Rf=0.60 (hexanes/EtOAc 19:1 (v/v)). NMR Spectroscopy: $^1$H NMR (500 MHz, CDCl$_3$, 23° C., δ): 7.21 (dd, J=8.7, 2.3 Hz, 1H), 6.96 (d, J=2.3 Hz, 1H), 6.66 (d, J=8.7 Hz, 1H), 3.84-3.78 (m, 2H), 3.40 (dd, J=12.8, 6.4, 1H), 3.24 (dd, J=12.8, 7.1 Hz, 1H), 2.11 (ddd, J=8.7, 5.0, 5.0 Hz, 1H), 1.38-1.32 (m, 1H), 1.31-1.25 (m, 1H), 1.08-1.04 (m, 1H), 0.98-0.94 (m, 1H), 0.68-0.58 (m, 2H), 0.40-0.31 (m, 2H). $^{13}$C NMR (125 MHz, CDCl$_3$, 23° C., δ): 156.9, 132.8, 129.5, 128.8, 113.4, 112.9, 73.3, 55.3, 20.8, 16.2, 12.8, 10.4, 3.3, 3.2. HRMS-FIA (m/z): calcd for C$_{14}$H$_{16}$BrN$_3$NaO [M+Na]$^+$, 344.0374; found, 344.0363.

t-butyl (((1S,2S)-2-(5-bromo-2-(cyclopropyl-methoxy)phenyl)cyclopropyl)methyl) carbamate (S10)

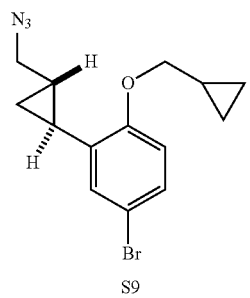

Figure 2B:
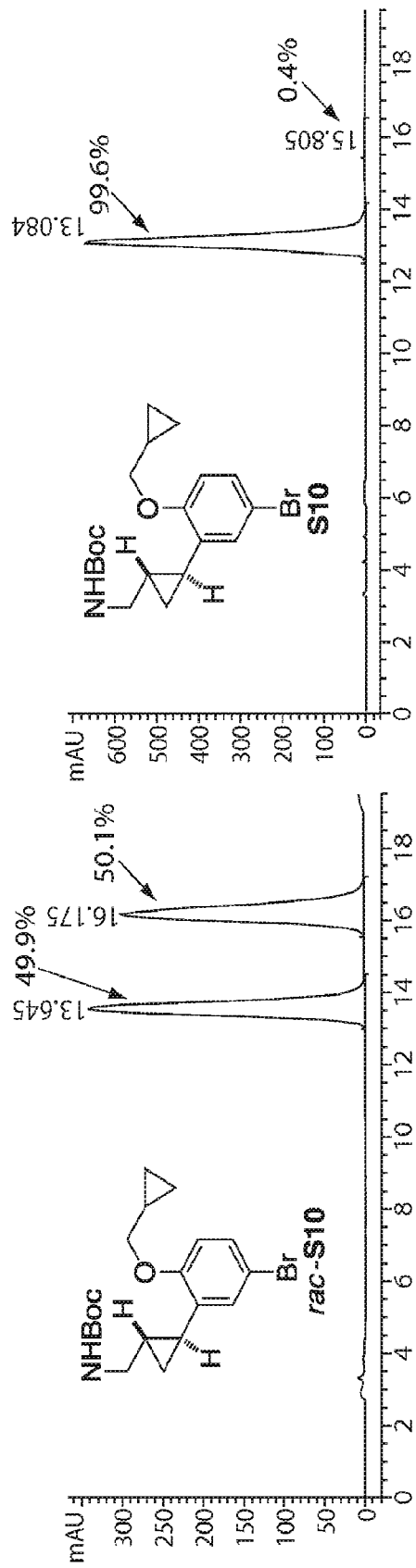
FIG. 2B shows the enantiodiscriminating HPLC trace of t-butyl (((1S,2S)-2-(5-bromo-2-(cyclopropylmethoxy) phenyl)cyclopropyl)methyl) carbamate (S10). HPLC method: Chiracel ODH column with 5% isopropanol/hexanes eluent for racemic S10 and enantioenriched S10. The percent of total integration is listed for each peak.
Figure 3A:
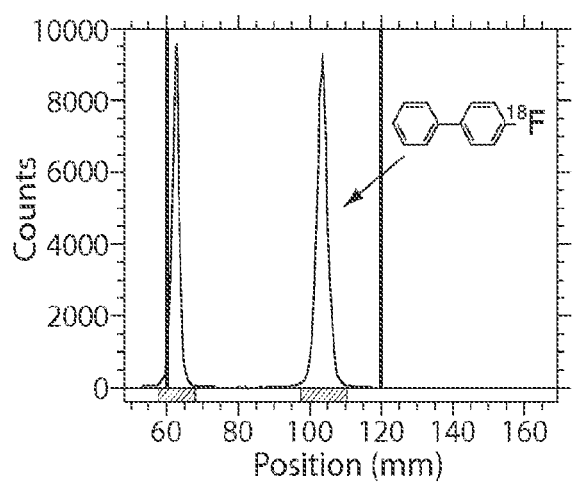
Figure 3B:
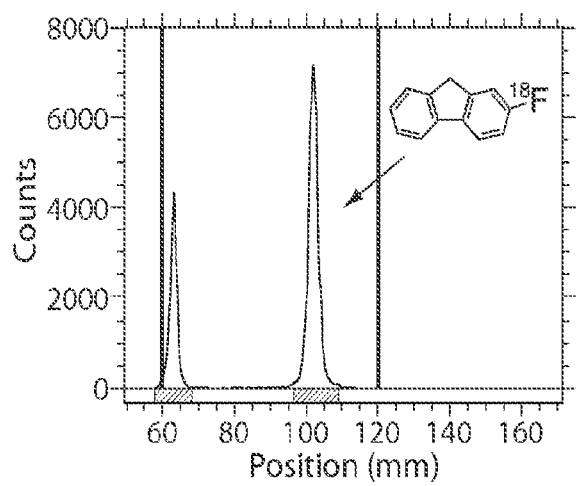
FIG. 3B shows an examplary radio TLC scan of [$^{18}$F]2b, entry 7 of Table S1. The percent of total integration is listed for [$^{18}$F]2b.
Figure 3C:
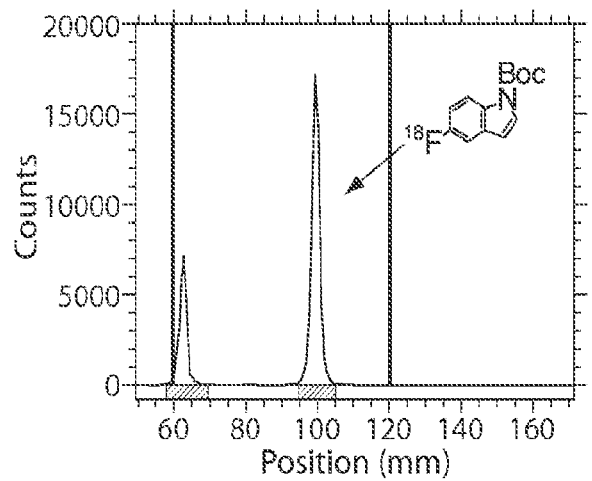
FIG. 3C shows an exemplary radio TLC scan of [$^{18}$F]2c, entry 14 of Table S1. The percent of total integration is listed for [$^{18}$F]2c.
Figure 3D:
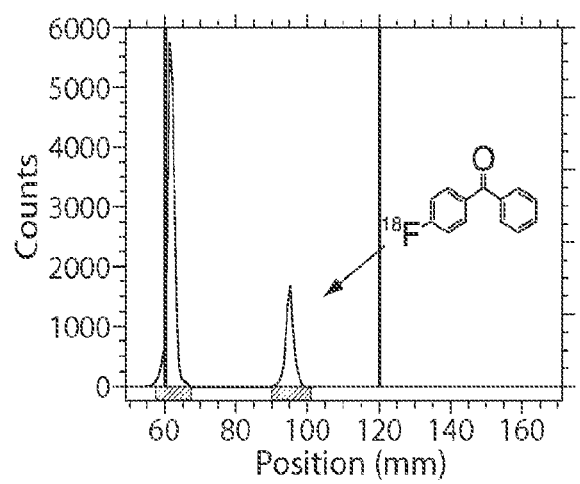
FIG. 3D shows an exemplary radio TLC scan of [$^{18}$F]2d, entry 23 of Table S1. The percent of total integration listed for [$^{18}$F]2d.
Figure 3E:
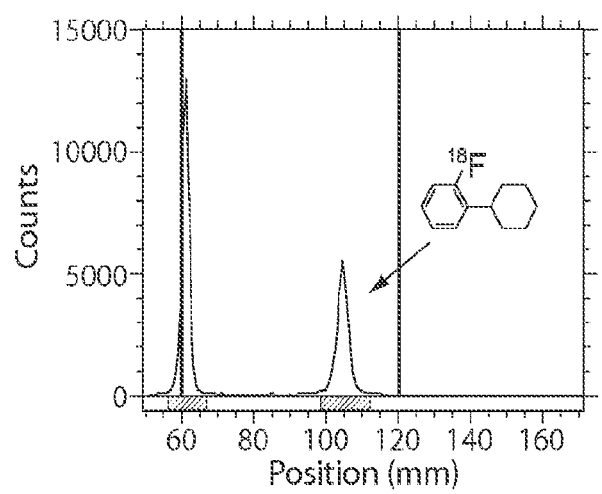
FIG. 3E shows an exemplary radio TLC scan of [$^{18}$F]2e, entry 25 of Table S1. The percent of total integration is listed for [$^{18}$F]2e.
Figure 3F:
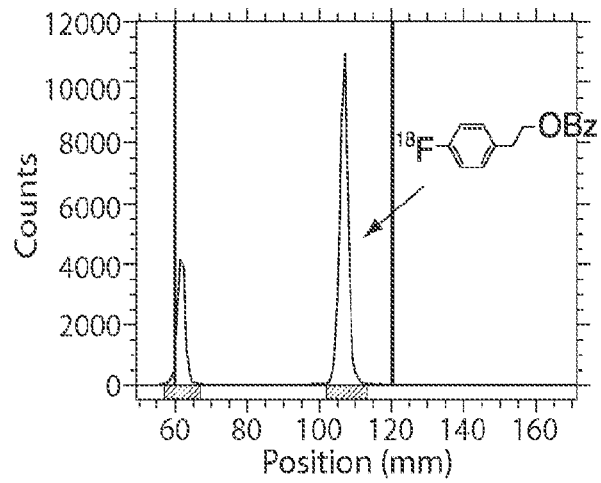
FIG. 3F shows an exemplary radio TLC scan of [$^{18}$F]2f, entry 34 of Table S1. The percent of total integration listed for [$^{18}$F]2f.
Figure 3G:
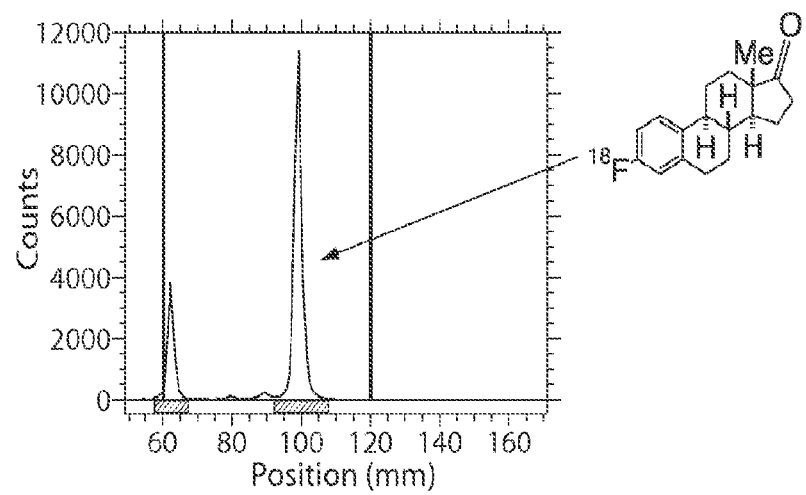
FIG. 3G shows an examplary radio TLC scan of [$^{18}$F]2g, entry 39 of Table S1. The percent of total integration is listed for [$^{18}$F]2g.
Figure 3H:
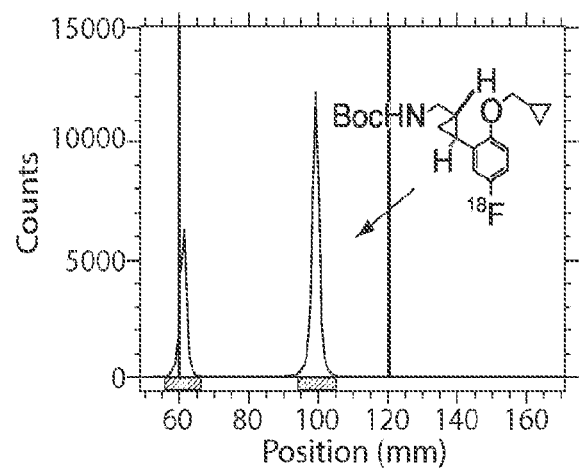
FIG. 3H shows an exemplary radio TLC scan of [$^{18}$F]2h, entry 44 of Table S1. The percent of total integration is listed for [$^{18}$F]2h.
Figure 3I:
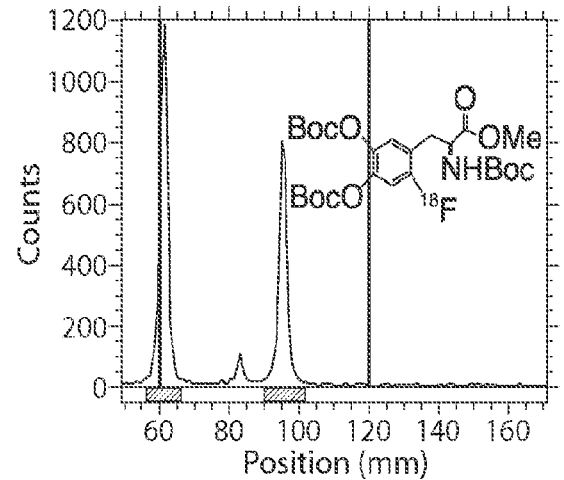
Figure 3J:
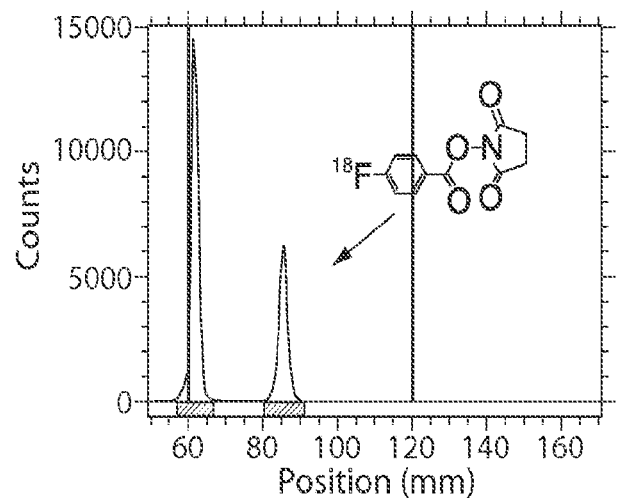
FIG. 3J shows an exemplary radio TLC scan of [$^{18}$F]2k, entry 63 of Table S1. The percent of total integration is listed for [$^{18}$F]2k.
Figure 3K:
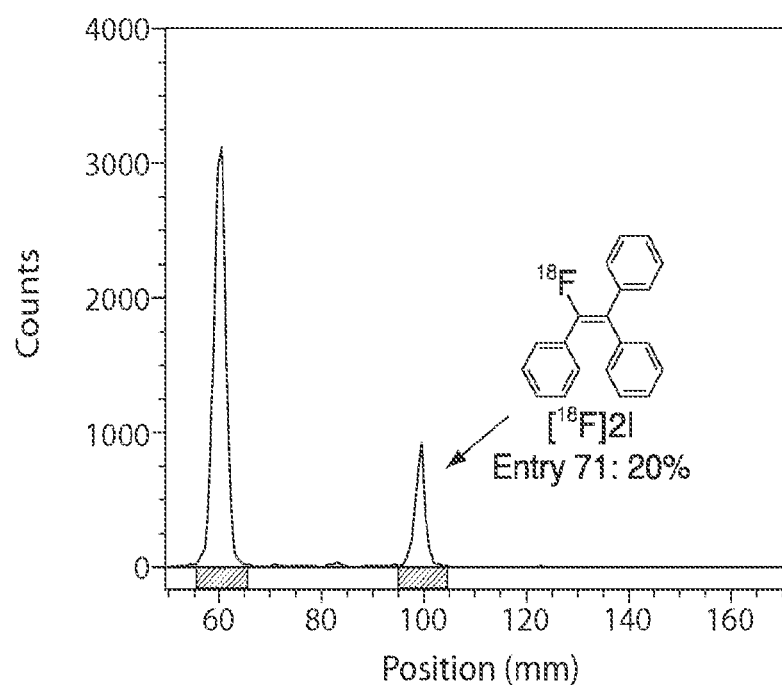
FIG. 3K shows an exemplary radio TLC scan of [$^{18}$F]2l, entry 71 of Table S1. The percent of total integration is listed for [$^{18}$F]2l.
Figure 4A:
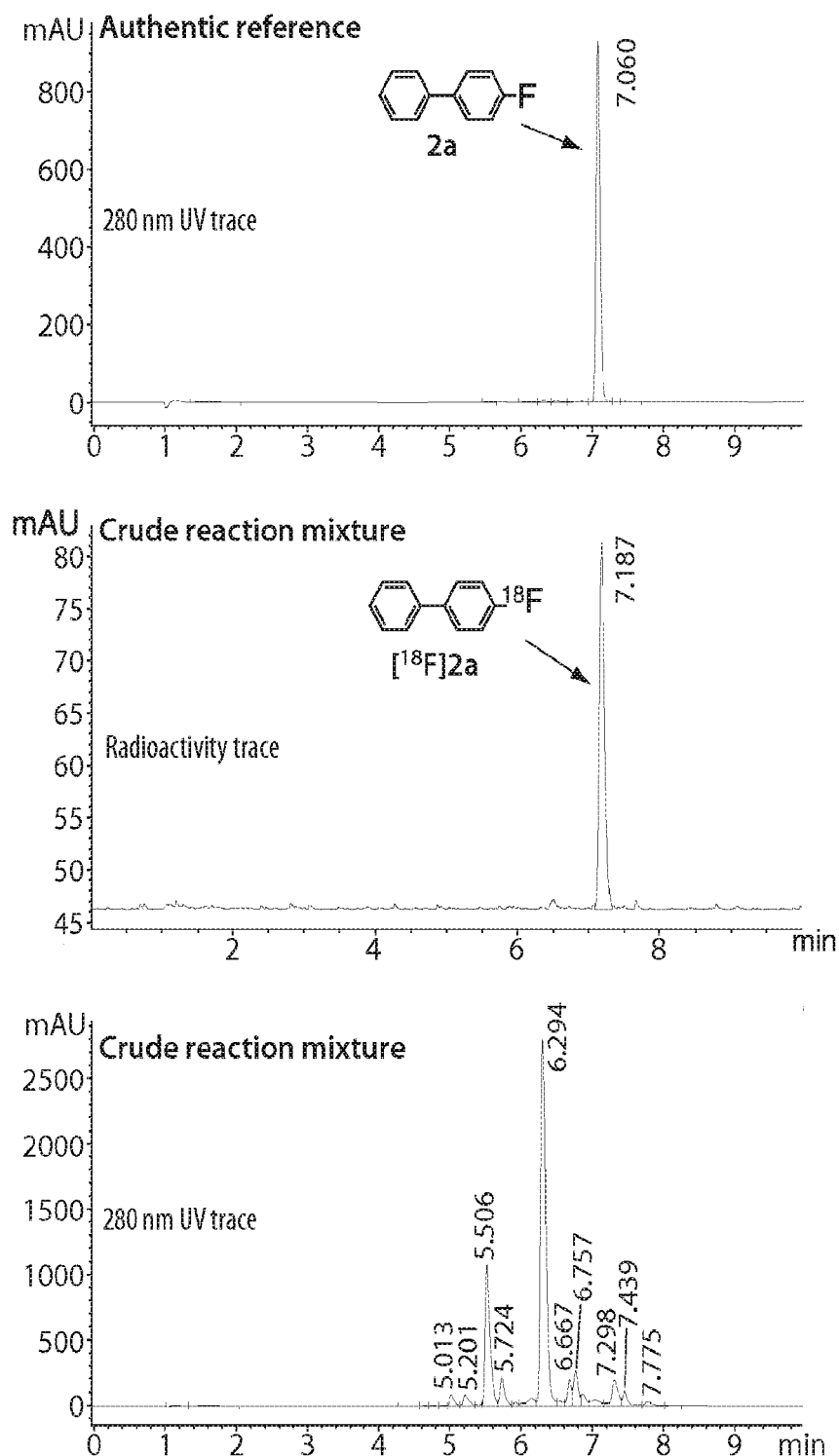
FIG. 4A shows the characterization of [$^{18}$F]2a. 280 nm UV trace (top) of authentic sample (2a), radioactivity trace of the reaction mixture (middle) containing [$^{18}$F]2a, and 280 nm UV trace (bottom) of the reaction mixture.
Figure 4B:
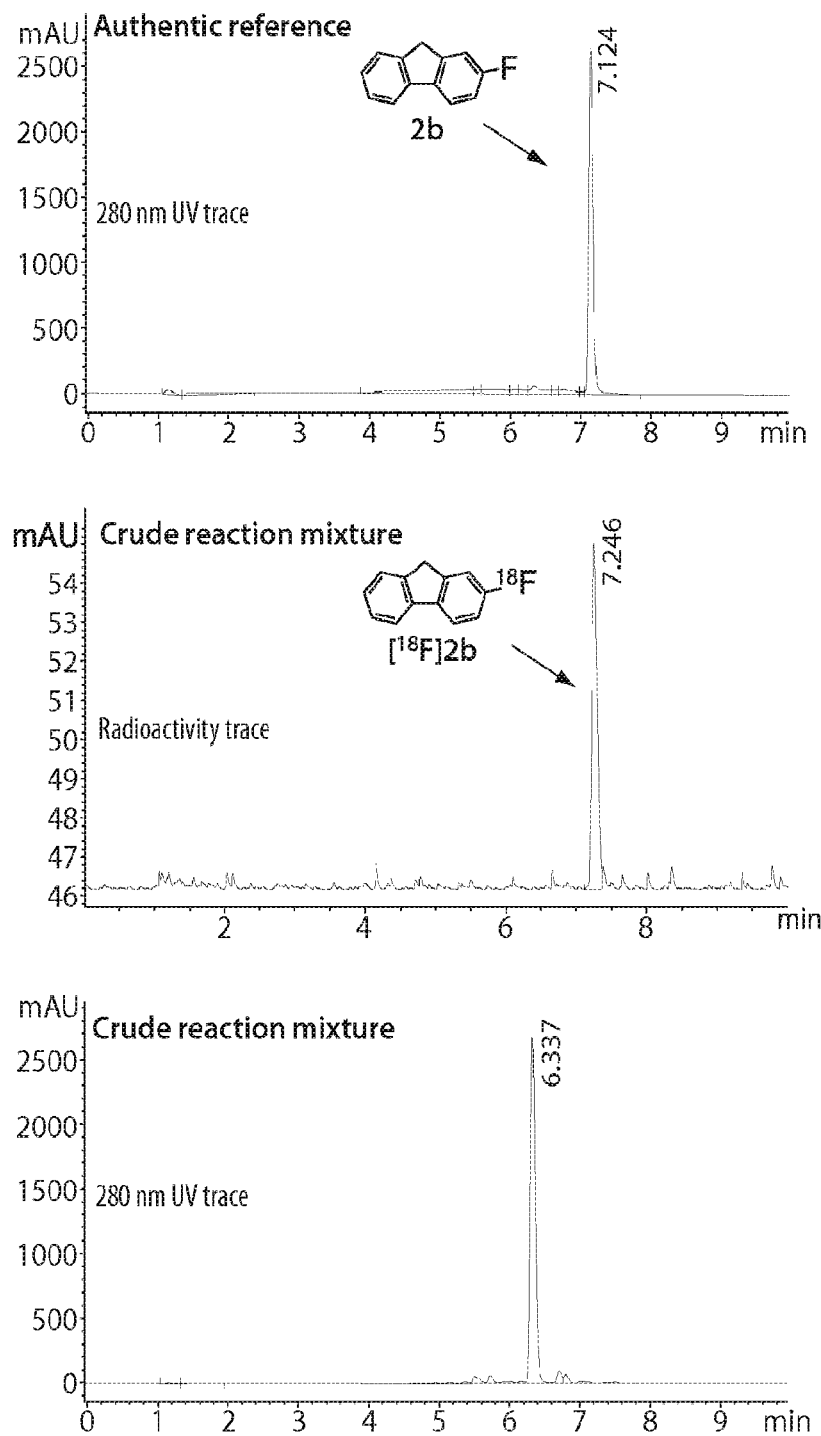
FIG. 4B shows the characterization of [$^{18}$F]2b. 280 nm UV trace (top) of authentic sample (2b), radioactivity trace of the reaction mixture (middle) containing [$^{18}$F]2b, and 280 nm UV trace (bottom) of the reaction mixture.
Figure 4C:
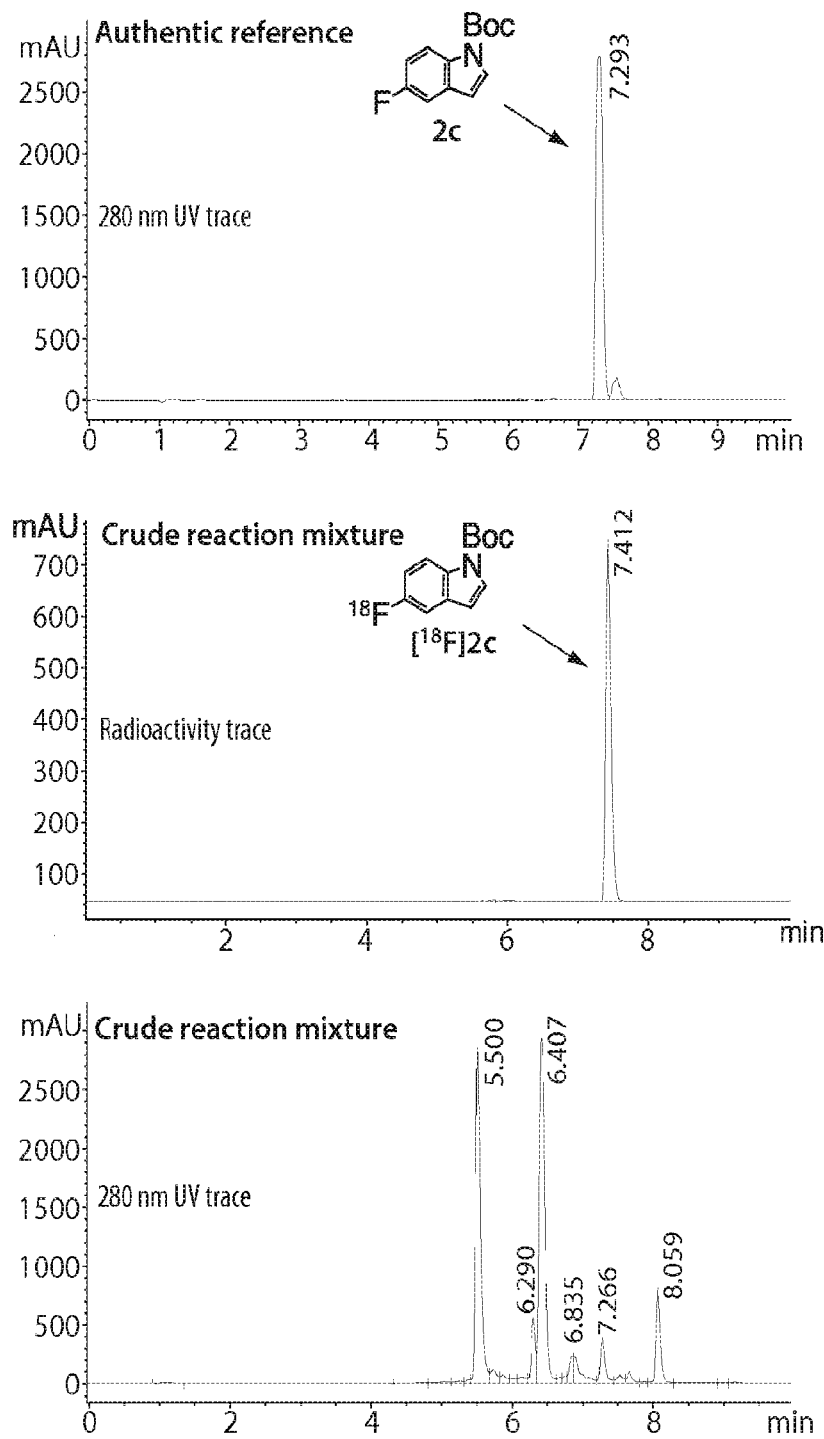
FIG. 4C shows characterization of [$^{18}$F]2c. 280 nm UV trace (top) of authentic sample (2c), radioactivity trace of the reaction mixture (middle) containing [18F]2c, and 280 nm UV trace (bottom) of the reaction mixture.
Figure 4D:
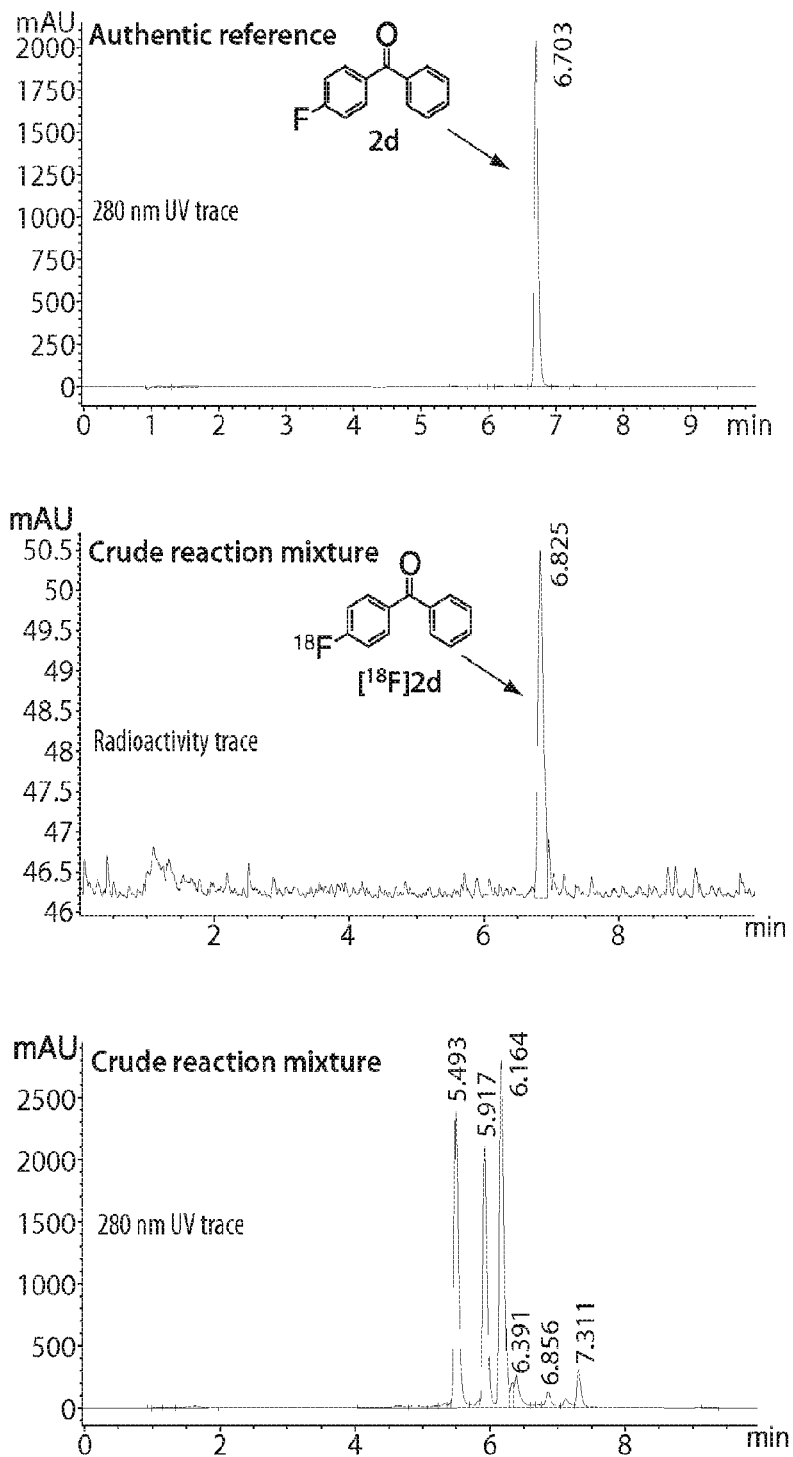
FIG. 4D shows the characterization of [$^{18}$F]2d. 280 nm UV trace (top) of authentic sample (2d), radioactivity trace of the reaction mixture (middle) containing [$^{18}$F]2d, and 280 nm UV trace (bottom) of the reaction mixture.
Figure 4E:
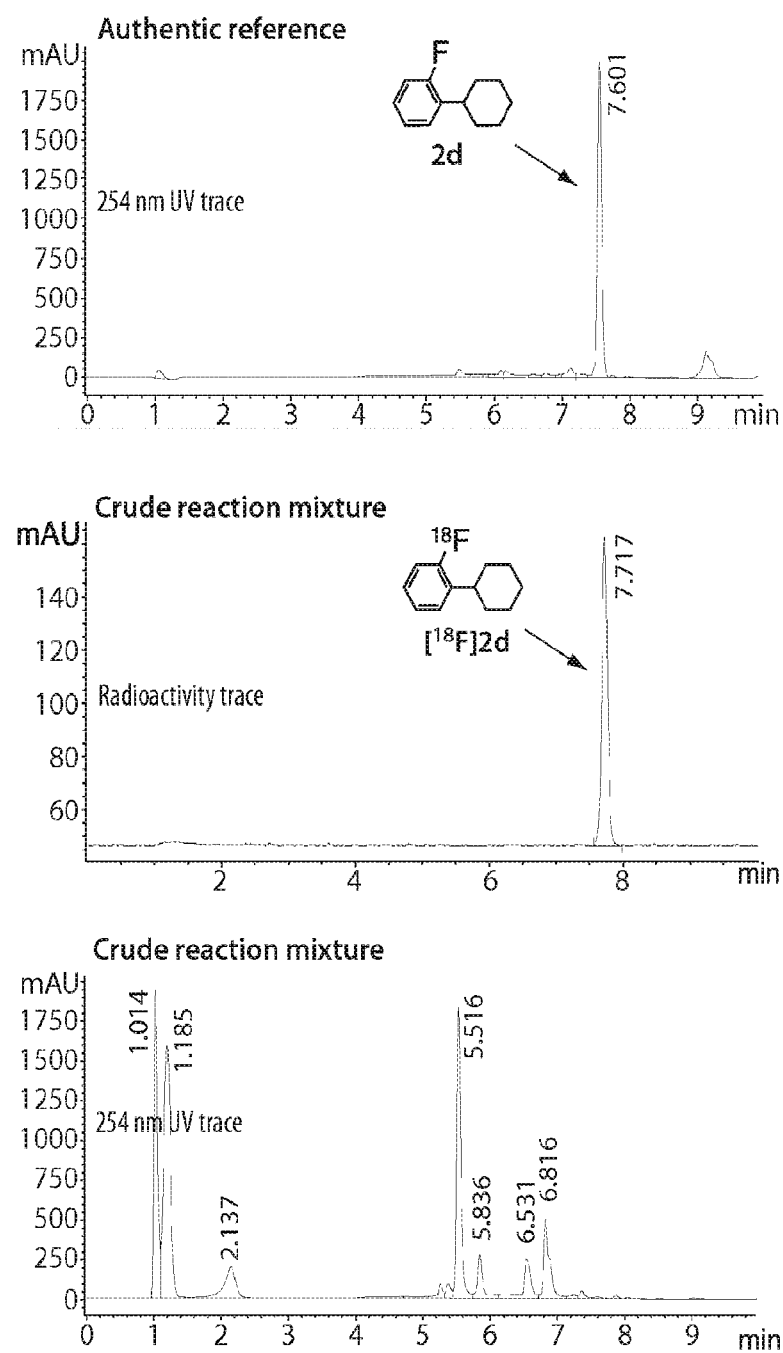
FIG. 4E shows the characterization of [$^{18}$F]2e. 254 nm UV trace (top) of authentic sample (2e and cyclohexylbenzene as a 1:2 mixture), radioactivity trace of the reaction mixture (middle) containing [18F]2e, and 254 nm UV trace (bottom) of the reaction mixture.
Figure 4F:
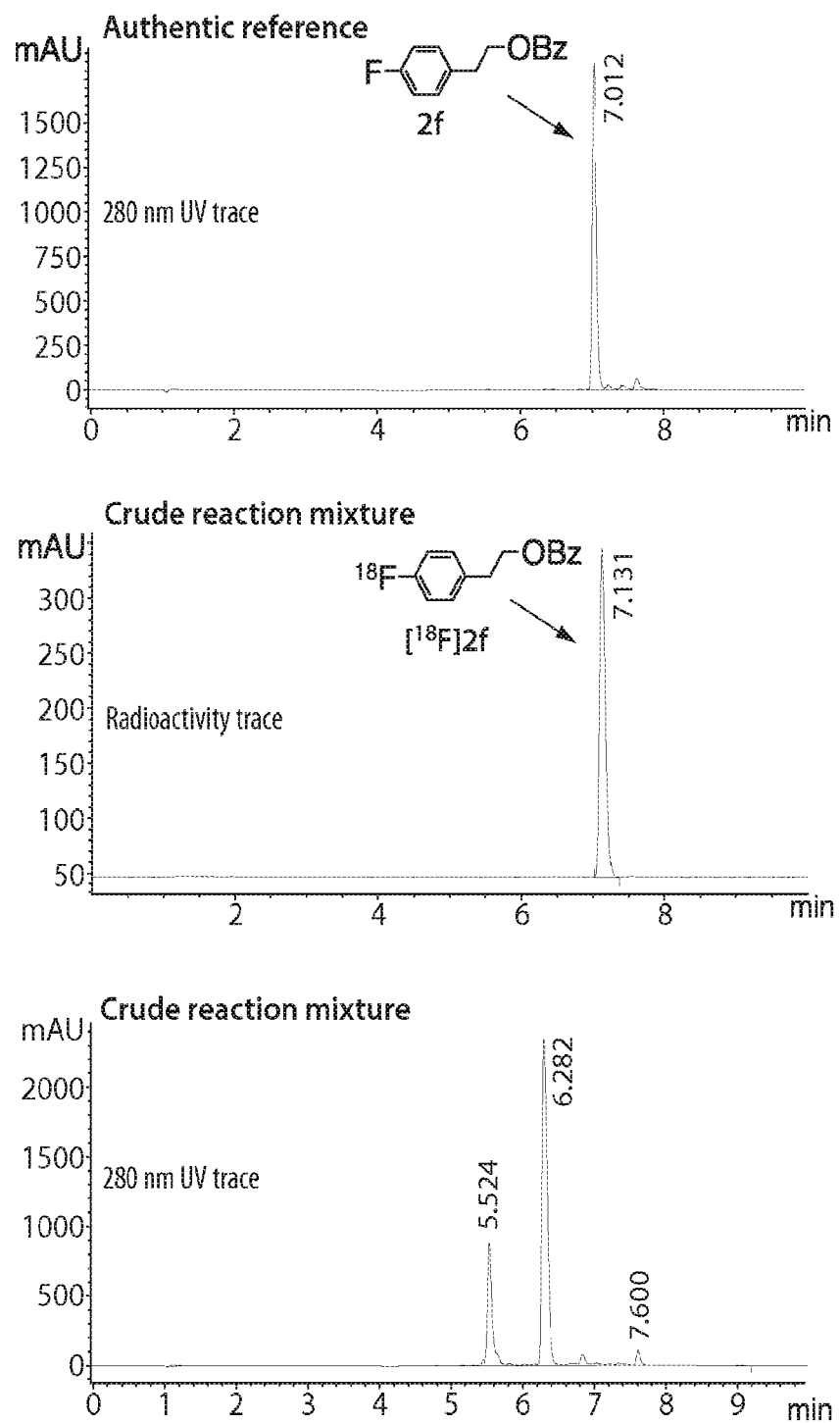
FIG. 4F shows the characterization of [$^{18}$F]2f. 280 nm UV trace (top) of authentic sample (2f), radioactivity trace of the reaction mixture (middle) containing [18F]2f, and 280 nm UV trace (bottom) of the reaction mixture.
Figure 4G:
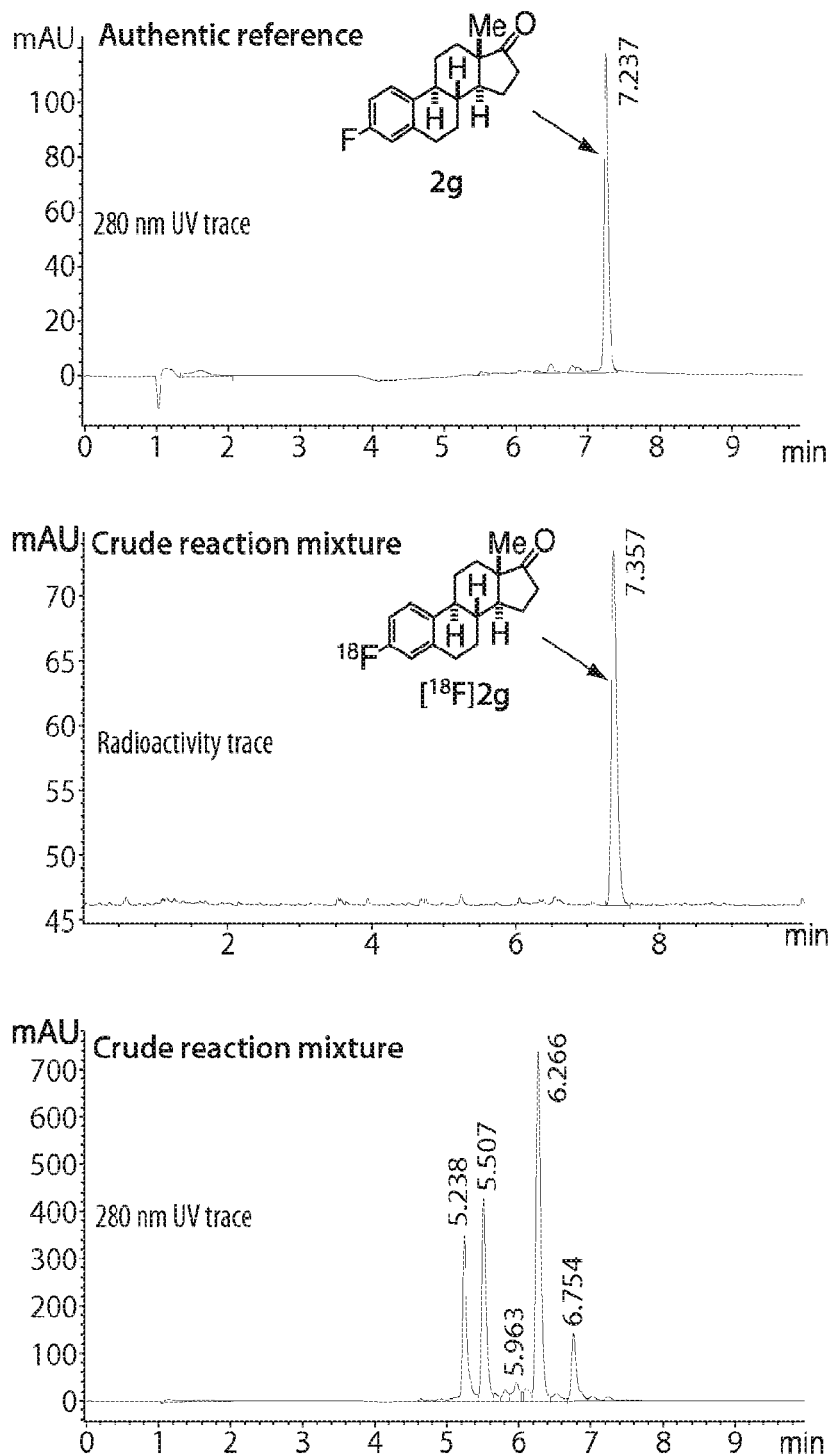
FIG. 4G shows characterization of [$^{18}$F]2g. 280 nm UV trace (top) of authentic sample (2g), radioactivity trace of the reaction mixture (middle) containing [$^{18}$F]2g, and 280 nm UV trace (bottom) of the reaction mixture.
Figure 4H:
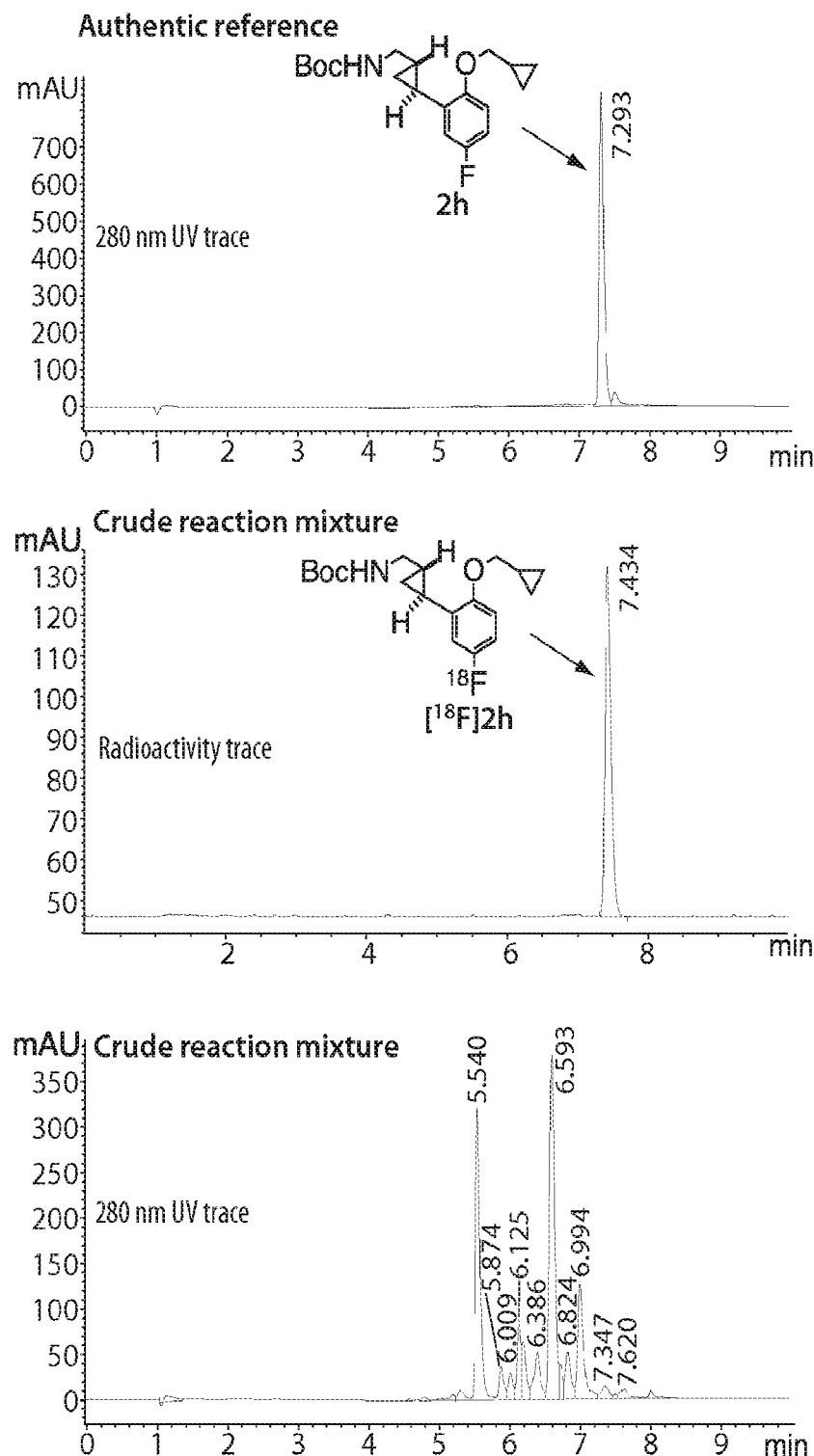
FIG. 4H shows the characterization of [$^{18}$F]2h. 280 nm UV trace (top) of authentic sample (2h), radioactivity trace of the reaction mixture (middle) containing [$^{18}$F]2h, and 280 nm UV trace (bottom) of the reaction mixture.
Figure 4I:
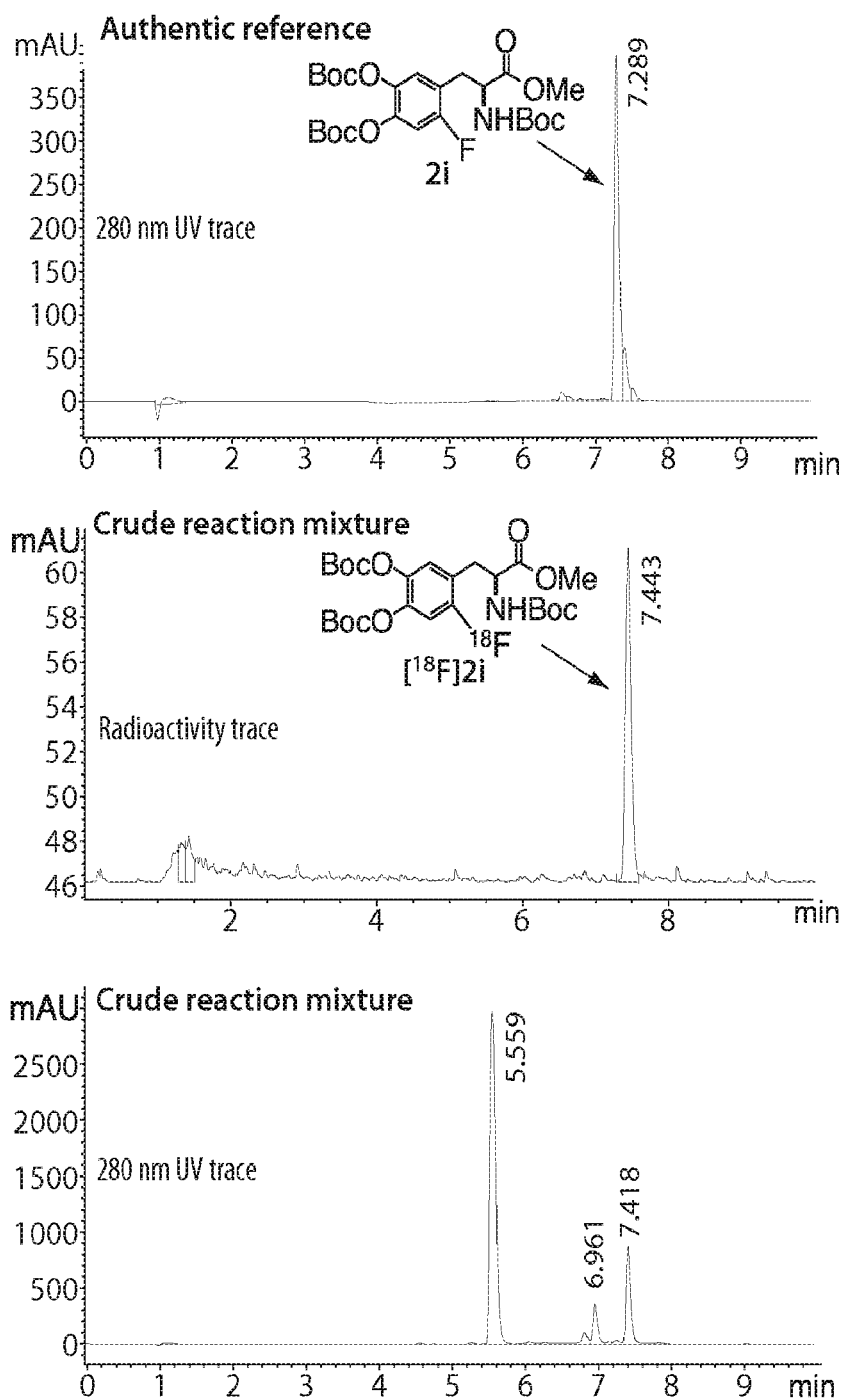
FIG. 4I shows the characterization of [$^{18}$F]2i. 280 nm UV trace (top) of authentic sample (2i), radioactivity trace of the reaction mixture (middle) containing [18F]2i, and 280 nm UV trace (bottom) of the reaction mixture.
Figure 4J:
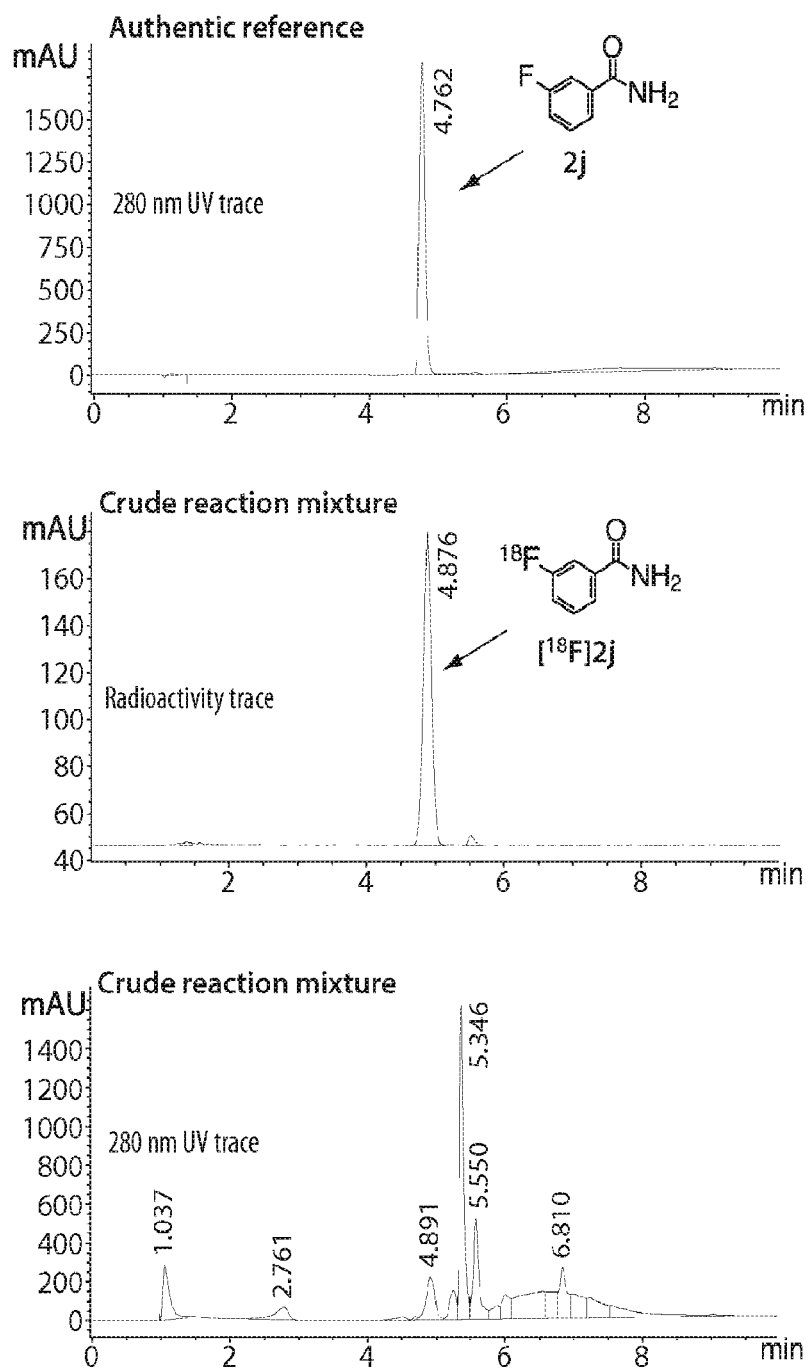
FIG. 4J shows the characterization of [$^{18}$F]2j. 280 nm UV trace (top) of authentic sample (2j), radioactivity trace of the reaction mixture (middle) containing [$^{18}$F]2j, and 280 nm UV trace (bottom) of the reaction mixture.
Figure 4K:
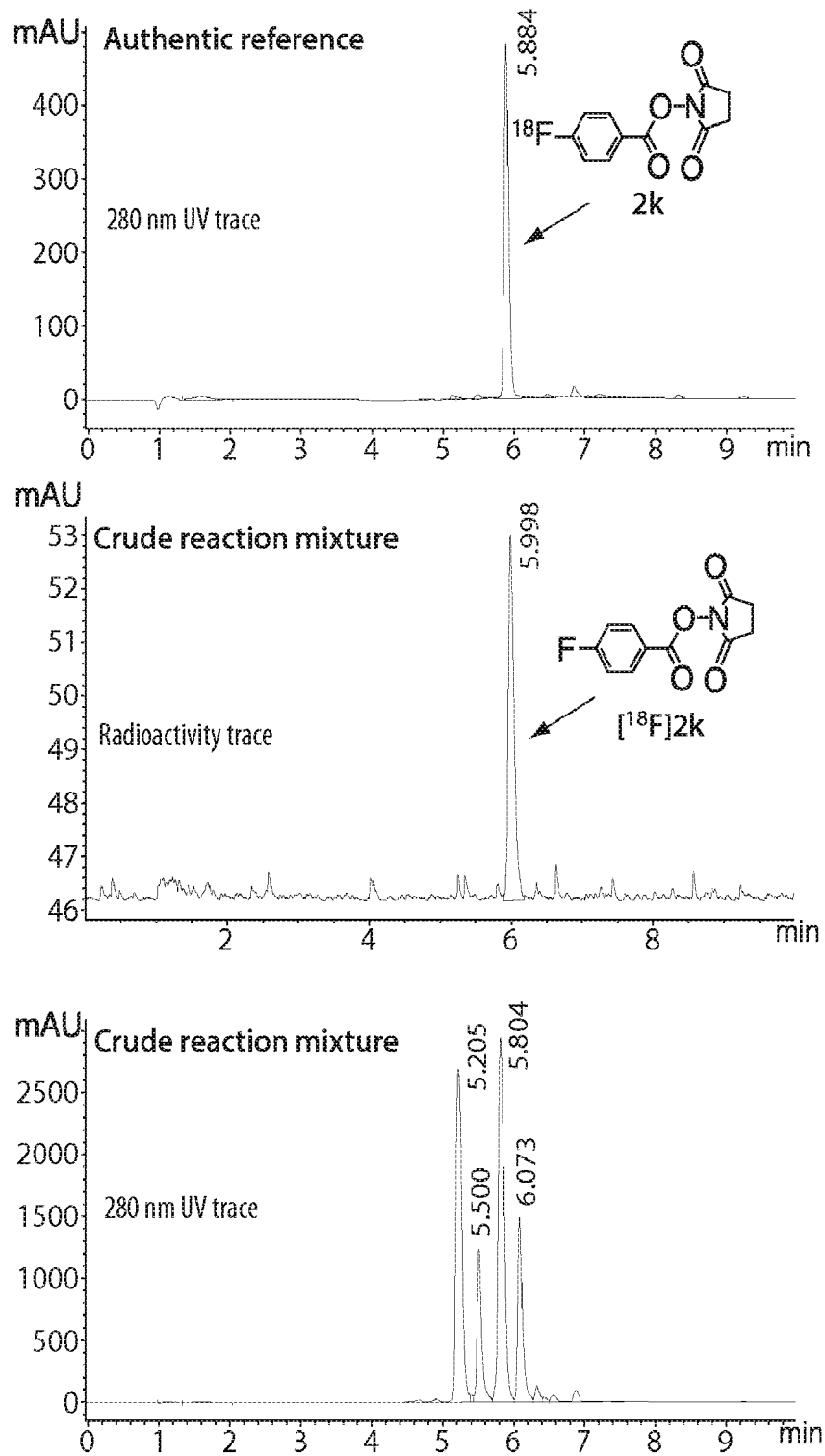
FIG. 4K shows the characterization of [$^{18}$F]2k. 280 nm UV trace (top) of authentic sample (2k), radioactivity trace of the reaction mixture (middle) containing [$^{18}$F]2k, and 280 nm UV trace (bottom) of the reaction mixture.
Figure 4L:
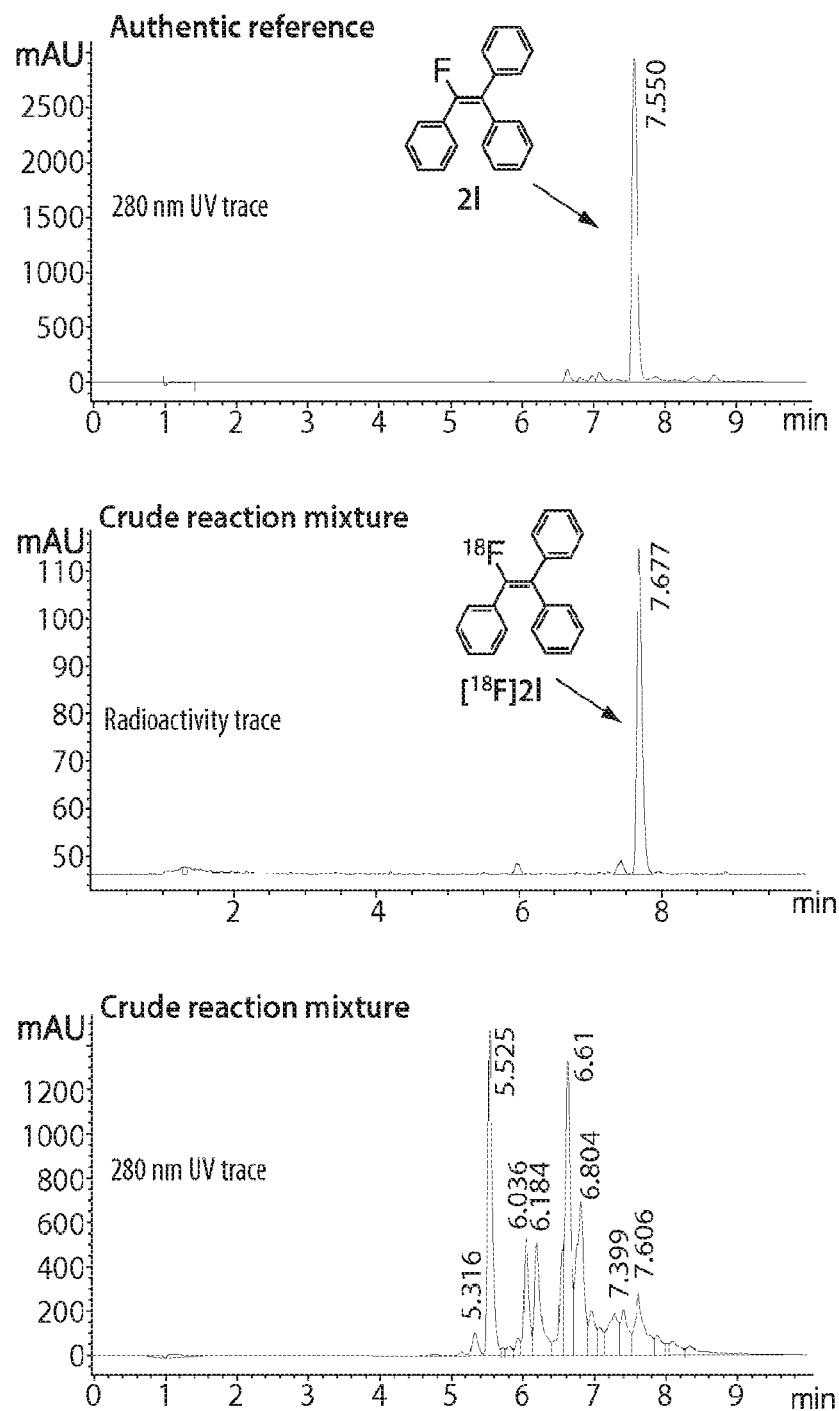
FIG. 4L shows the characterization of [$^{18}$F]2l. 280 nm UV trace (top) of authentic sample (2l), radioactivity trace of the reaction mixture (middle) containing [$^{18}$F]2l, and 280 nm UV trace (bottom) of the reaction mixture.

To 2-((1S,2S)-2-(azidomethyl)cyclopropyl)-4-bromo-1-(cyclopropylmethoxy)benzene (S9) (1.90 g, 5.90 mmol, 1.00 equiv) in a round-bottom flask open to air in a 2:1 solution of dioxane:H$_2$O (45 mL) cooled to 0° C. was added tin(II) chloride (5.59 g, 29.5 mmol, 5.00 equiv). The reaction mixture was allowed to warm to 23° C. and stirred for 15 hours. Saturated aqueous NaHCO$_3$ solution (50 mL) was carefully added. The addition was accompanied by foaming. H$_2$O (15 mL) was added followed by Boc$_2$O (3.86 g, 4.11 mL, 17.7 mmol, 3.00 equiv). The reaction mixture was stirred for 3 hours and then transferred to a separatory funnel. The reaction mixture was extracted from with EtOAc (3×75 mL). The combined organic phases were washed with brine (75 mL), dried with Na$_2$SO$_4$, and concentrated in vacuo. The residue was purified by chromatography on silica gel, eluting with a gradient of 5-20% EtOAc in hexanes (v/v) to afford 1.96 g of the title compound as a colorless solid (85% yield). The enantioenriched product could be recrystallized by suspending the solid in hexanes (10 mL), heating the suspension to reflux to dissolve the solid, cooling the solution, and collecting the solid by filtration, affording the title compound in >99% ee as determined on a Chiracel ODH column with 5% isopropanol/hexanes eluent (see FIG. 2B). Rf=0.25 (hexanes/EtOAc 19:1 (v/v)). NMR Spectroscopy: $^1$H NMR (500 MHz, CDCl$_3$, 23° C., δ): 7.23 (dd, J=8.3, 2.4 Hz, 1H), 7.06 (br d, J=2.0 Hz, 1H), 6.66 (d, J=8.8 Hz, 1H), 5.27 (br, 1H), 3.97 (dd, J=9.5, 7.1 Hz, 1H), 3.72-3.66 (m, 2H), 2.66 (br dd, J=10.0, 10.0, 1H), 1.83 (ddd, J=6.6, 6.6, 4.9 Hz, 1H), 1.43 (br, 10H), 1.06-0.99 (br m, 2H), 0.83-0.80 (br m, 1H), 0.67 (br m, 2H), 0.38 (br m, 2H). $^{13}$C NMR (125 MHz, CDCl$_3$, 23° C., δ): 157.2, 155.9, 132.6, 130.3, 129.7, 112.8, 112.7, 79.1, 73.5, 45.7, 28.6, 21.1, 17.4, 10.6, 10.3, 3.5. HRMS-FIA (m/z): calcd for C$_{19}$H$_{26}$BrNNaO$_3$ [M+Na]$^+$, 418.0988; found, 418.0994.

Synthesis of Nickel(II) Aryl Bromide Complex (7h)

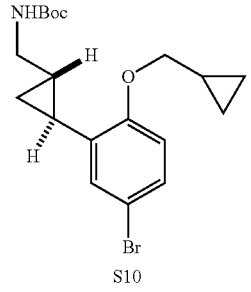

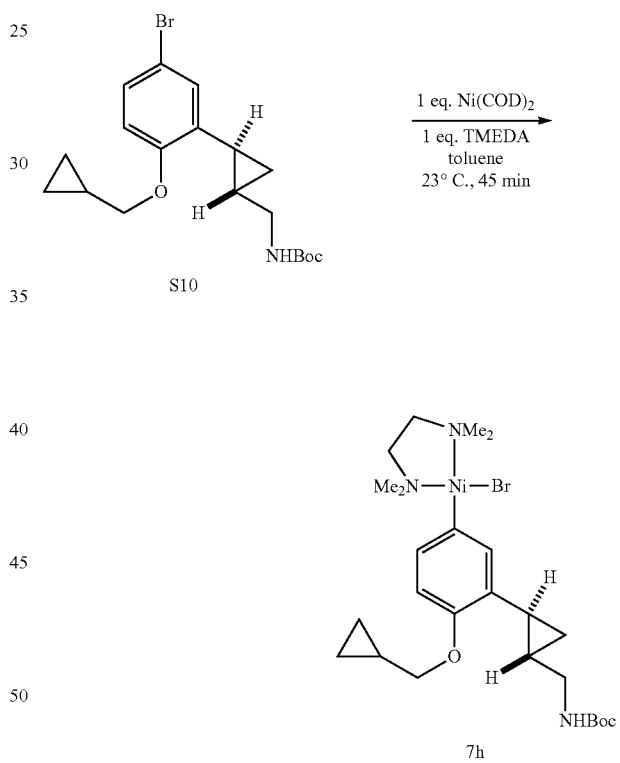

To a solution of TMEDA (0.0537 mL, 0.358 mmol, 1.00 equiv) and t-butyl (((1S,2S)-2-(5-bromo-2-(cyclopropylmethoxy)phenyl)cyclopropyl)methyl) carbamate (S10) (0.142 g, 0.358 mmol, 1.00 equiv) in toluene (3 mL) was added bis(cyclooctadiene)nickel(0) (Ni(COD)$_2$, 0.200 g, 0.358 mmol, 1.00 equiv), and the mixture was stirred at room temperature for 45 min. Pentane (16 mL) was added to the mixtures and the resulting solid was collected on a frit. The solid was washed with pentane (3×5 mL) and dried in vacuo to afford 0.183 g of the title compound as a peach solid (89%).

Anal: calcd for C$_{25}$H$_{42}$BrN$_3$NiO$_3$: C, 52.57; H, 7.41; N, 7.36; found: C, 50.08; H, 7.03; N, 7.10. Numerous attempts were made to get elemental analysis data satisfactory one was not obtained. However, purification by chromatography on next step enables to access pure 1h.

Synthesis of Nickel(II) Aryl Complex (1h)

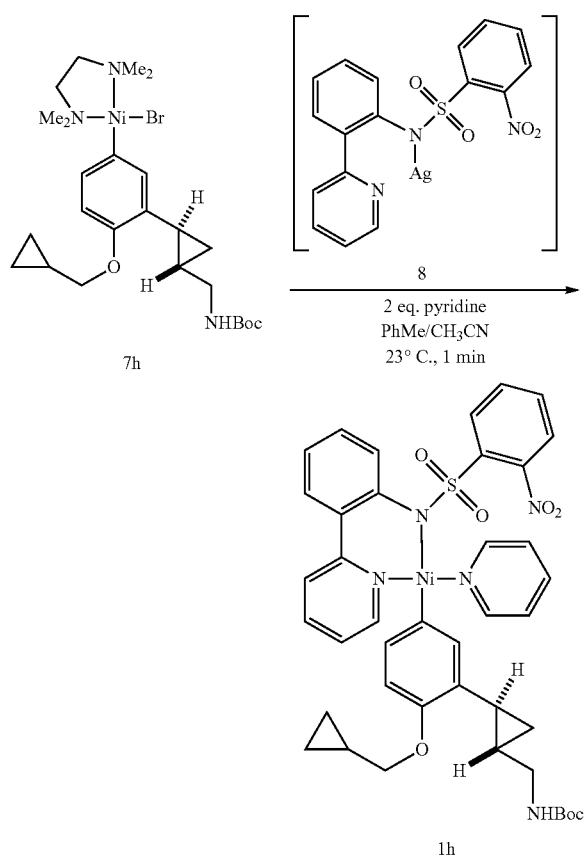

To (2-(2-Pyridinyl)phenyl-2-nitrobenzenesulfonamide)silver(I) (8) (0.113 g, 0.245 mmol, 1.00 equiv) and nickel(II) aryl bromide complex (7h) (0.140 g, 0.245 mmol, 1.00 equiv) in a 20 mL vial was added an toluene solution (3 mL) that contained pyridine (38.8 mg, 39.5 L, 0.490 mmol, 2.00 equiv) at 23 °C., followed by addition of acetonitrile (0.5 mL). After stirring for 1 min at 23, the solution was filtered through a glass frit and the filtered cake was extracted further with dichloromethane (3×5 mL). The combined filtrate was concentrated in vacuo and the resulting residue was purified by chromatography on silica gel eluting with hexanes/EtOAc 1:2 (v/v) recrystallized with $CH_2Cl_2$/pentane to afford 75.0 mg of the title compound as a yellow solid (38%).

Rf=0.47 (hexanes/EtOAc 1:2 (v/v)). NMR Spectroscopy: $^1$H NMR (500 MHz, $CD_2Cl_2$, 23 °C., δ): 9.09 (d, J=3.4 Hz, 2H), 8.15 (dd, J=8.9, 6.0 Hz, 1H), 7.61-7.63 (m, 3H), 7.39-7.32 (m, 3H), 7.21-7.18 (m, 3H), 7.15-7.13 (m, 3H), 7.04-6.99 (m, 2H), 6.85 (s, 1H), 6.63-6.60 (m, 1H), 6.36-6.31 (m, 1H), 5.29 (br, 1H), 3.75 (br s, 1H), 3.56-3.48 (m, 1H), 2.57-2.52 (br m, 1H), 2.58-2.50 (br m, 2H), 1.62 (br s, 1H), 1.42-1.29 (m, 10H), 0.67-0.62 (br m, 2H), 0.57-0.54 (m, 2H) 0.26-0.24 (m, 2H). Note: A conformational isomer was observed in $^1$H NMR spectrum. A reliable $^{13}$C NMR data was not obtained due to the decomposition of 1h in the solvent over time. Anal: calcd for $C_{41}H_{43}N_5NiO_7S$: C, 60.90; H, 5.36; N, 8.66; found: C, 60.21; H, 5.57; N, 8.66.

N-(tert-butoxycarbonyl)-3,4-di(tert-butoxycarbonyloxy)-6-bromo-L-phenylalaninemethyl ester (S11)

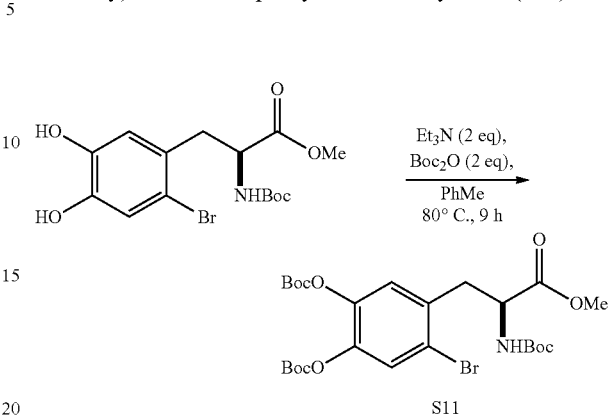

(S)-N-(tert-butyloxycarbonyl)-2-bromo-4,5-dihydroxyphenylalanine methyl ester was prepared by a published method. To the mixture of (S)-N-(tert-butyloxycarbonyl)-2-bromo-4,5-dihydroxyphenylalanine methyl ester (8.00 g, 20.5 mmol, 1.00 equiv) and $Et_3N$ (5.72 ml, 4.15 g, 164 mmol, 2.00 equiv) in a round-bottom flask in PhMe (100 ml) was added $Boc_2O$ (3.86 g, 4.11 mL, 17.7 mmol, 3.00 equiv) in one portion. The reaction mixture was stirring under nitrogen atmosphere at 80° C. for 9 h. The reaction mixture was cooled to 23 °C. and was concentrated in vacuo. The residue was purified by chromatography on silica gel, eluting with a gradient of 30% EtOAc in hexanes (v/v) to afford 11.5 g of the title compound as a light yellow solid (95% yield). Rf=0.53 (hexanes/EtOAc 2:1 (v/v)). NMR Spectroscopy: $^1$H NMR (500 MHz, $CDCl_3$, 23 °C., δ): 7.46 (s, 1H), 7.11 (s, 1H), 5.10 (d, J=8.4 Hz, 1H), 4.61-4.57 (m, 1H), 3.68 (s, 3H), 3.25-3.20 (m, 1H), 3.11-3.06 (m, 1H), 1.51 (s, 18H), 1.37 (s, 9 H). $^{13}$C NMR (125 MHz, $CDCl_3$, 23 °C., δ): 172.2, 155.0, 150.3, 141.8, 141.7, 134.6, 127.2, 125.3, 120.8, 84.3, 84.1, 80.1, 53.3, 52.5, 38.2, 28.3, 27.6, 27.5.

Synthesis of Nickel(II) Aryl Bromide Complex (7i)

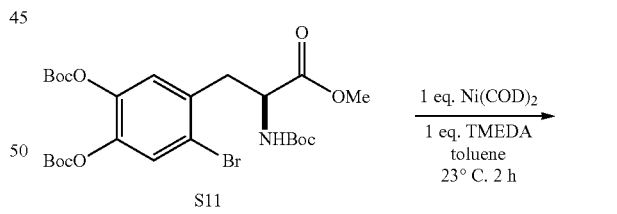

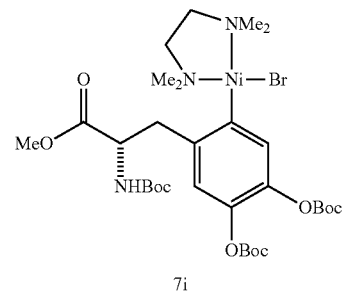

To a solution of TMEDA (0.161 mL, 1.08 mmol, 1.00 equiv) and N-(tert-butoxycarbonyl) -3,4-di(tert-butoxycarbonyloxy)-6-bromo-L-phenylalaninemethyl ester (S11) (0.635 g, 1.08 mmol, 1.00 equiv) in toluene (8 mL) was added bis(cyclooctadiene)nickel(0) (Ni(COD)$_2$, 0.300 g, 1.08 mmol, 1.00 equiv), and the mixture was stirred at room temperature for 2 h. The solution was concentrated in vacuo and pentane (16 mL) was added to the mixtures and the resulting solid was collected on a frit. The solid was washed with pentane (3×5 mL) and dried in vacuo to afford 0.735 g of the title compound as a red solid (92%). Anal: calcd for $C_{31}H_{52}BrN_3NiO_{10}$·(PhMe)$_{0.2}$: C, 49.65; H, 6.89; N, 5.36; found: C, 49.29; H, 6.65; N, 4.74.

Synthesis of Nickel(II) Aryl Complex (1i)

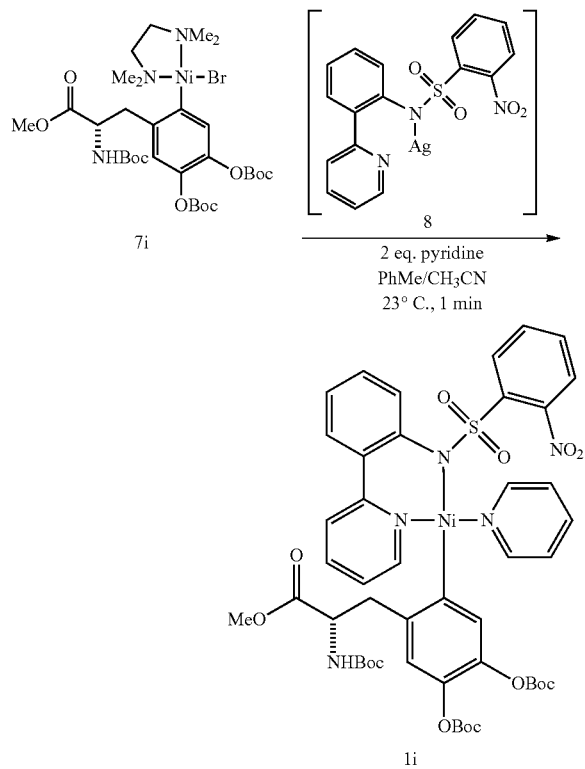

To (2-(2-Pyridinyl)phenyl-2-nitrobenzenesulfonamide)silver(I) (7) (0.302 g, 0.650 mmol, 1.00 equiv) and nickel(II) aryl bromide complex (6i) (0.500 g, 0.650 mmol, 1.00 equiv) in a round-bottom flask was added an toluene solution (8 mL) that contained pyridine (103 mg, 105 μL, 1.31 mmol, 2.00 equiv) at 23° C., followed by addition of acetonitrile (2.0 mL). After stirring for 1 min at 23, the solution was filtered through a glass frit and the filtered cake was extracted further with dichloromethane (3×5 mL). The combined filtrate was concentrated in vacuo and the resulting residue was purified by chromatography on silica gel eluting with hexanes/EtOAc 1:3 (v/v) (0.5% Et$_3$N) to afford 0.260 g of the title compound as a yellow solid (40%). Rf=0.40 (hexanes/EtOAc 1:2 (v/v)). NMR Spectroscopy: $^1$H NMR (500 MHz, CD$_2$Cl$_2$, 23° C., δ): 9.04 (d, J=4.9 Hz, 2H), 8.32 (d, J=5.4 Hz, 0.4H), 8.26 (d, J=5.4 Hz, 0.6H), 8.05 (s, 1H), 7.66-7.32 (m, 7H), 7.27-7.15 (m, 5H), 7.08-7.01 (m, 4H), 6.73-6.63 (m, 1H), 6.40 (s, 0.6H), 6.32 (s, 0.4H), 4.35-4.22 (m, 1H), 4.07-3.93 (m, 1H), 3.88- 3.80 (m, 2H), 3.54-3.41 (m, 3H), 1.59 (s, 5H), 1.58 (s, 5H), 1.44 (s, 9H), 1.31 (s, 8H). $^{13}$C NMR (125 MHz CD$_2$Cl$_2$, 23° C., δ): 173.2, 156.2, 155.3, 154.5, 151.8, 151.5, 151.4, 147.2, 140.8, 140.7, 139.7, 139.5, 139.3, 138.3, 138.0, 137.6, 137.5, 136.6, 136.3, 135.8, 132.0, 130.9, 130.8, 130.2, 129.1, 129.1, 128.6, 127.9, 127.8, 124.8, 124.7, 124.6, 123.6, 123.0, 122.7, 122.5, 119.4, 119.2, 83.5, 83.4, 79.8, 54.6, 52.3, 40.8, 28.4, 28.1, 27.9, 27.7. Note: Conformational isomers were observed in $^1$H NMR spectrum. Fractional hydrogen integration is possibly due to slow rotation about bonds as seen for similar complexes. Anal: calcd for $C_{47}H_{53}N_5NiO_{14}S$: C, 56.30; H, 5.33; N, 6.98; found: C, 55.98; H, 5.18; N, 6.90.

Synthesis of Nickel Aryl Bromide Complex (7j)

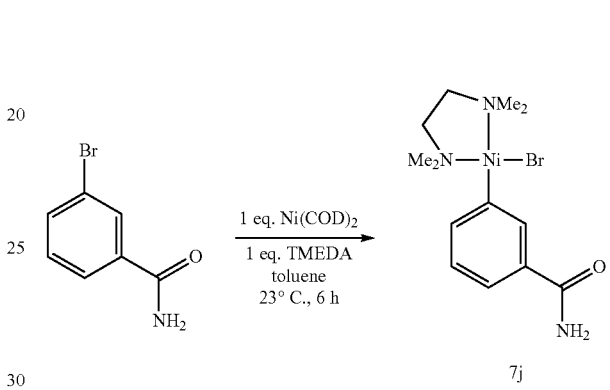

To a solution of TMEDA (83.0 mg, 0.107 mL, 0.717 mmol, 1.00 equiv) and 3-bromobenzamide (143 mg, 0.717 mmol, 1.00 equiv) in toluene (4 mL) was added Ni(COD)$_2$ (200 mg, 0.717 mmol, 1.00 equiv), and the mixture was stirred at room temperature for 6 h. Pentane (16 mL) was added to the mixtures and the resulting solid was collected on a frit. The solid was washed with pentane (3×5 mL) and dried in vacuo to afford 225 mg of the title compound as a pink solid (84%). Anal: calcd for $C_{13}H_{22}BrN_3NiO$: C, 41.64; H, 5.91; N, 11.21; found: C, 41.36; H, 5.78; N, 10.95.

Synthesis of Nickel Aryl Complex (1j)

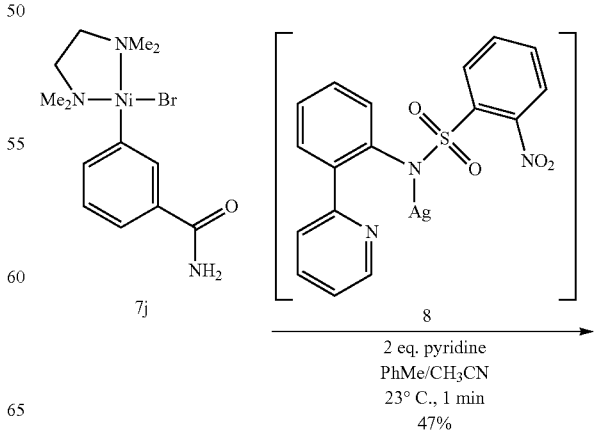

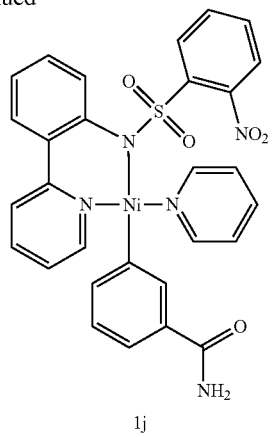

1j

To (2-(2-pyridinyl)phenyl-2-nitrobenzenesulfonamide)silver(I) (8) (247 mg, 0.533 mmol, 1.00 equiv) and nickel aryl bromide complex (7j) (200 mg, 0.533 mmol, 1.00 equiv) in a 20 mL vial was added a toluene solution (4 mL) that contained pyridine (84.0 mg, 86.0 µL, 1.07 mmol, 2.00 equiv) at 23 °C., followed by addition of acetonitrile (1.0 mL). After stirring for 1 min at 23, the solution was filtered through a glass frit and the filtered cake was extracted further with dichloromethane (3×5 mL). The combined filtrate was concentrated in vacuo and the resulting residue was purified by chromatography on silica gel eluting with EtOAc and further recrystallized by dissolving the columned solid in $CH_2Cl_2$ (2 mL) and layering with pentane (20 mL) to afford 154 mg of the title compound as a yellow solid (47%). Rf=0.26 (EtOAc). NMR Spectroscopy: $^1H$ NMR (500 MHz, $CD_2Cl_2$, 23 °C., δ): 9.13 (d, J=4.9 Hz, 2H), 8.15 (d, J=5.4 Hz, 1H), 7.86 (s, 1H), 7.78 (d, J=7.2 Hz, 1H), 7.63-7.56 (m, 3H), 7.42-7.32 (m, 3H), 7.23-7.17 (m, 4H), 7.08-7.02 (m, 4H), 6.87-6.84 (m, 1H), 6.64- 6.61 (m, 1H), 5.94 (br s, 1H), 5.32 (br s, 1H). $^{13}C$ NMR (125 MHz $CD_2Cl_2$, 23 °C., δ): 157.1, 156.2, 152.5, 151.5, 147.3, 141.3, 139.5, 137.9, 137.3, 136.7, 136.0, 134.1, 131.7, 130.9, 130.8, 130.2, 128.8, 128.7, 126.0, 124.8, 124.5, 123.4, 123.0, 122.3. Anal: calcd for $C_{29}H_{23}N_5NiO_5S$ $(CH_2Cl_2)_{0.25}$: C, 55.46; H, 3.74; N, 11.05; found: C, 55.22; H, 3.82; N, 11.28.

Synthesis of Nickel(II) Aryl Bromide Complex (7j)

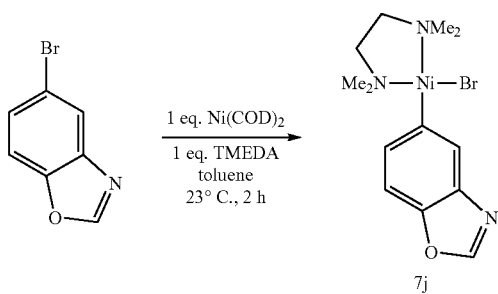

To a solution of TMEDA (0.107 mL, 0.717 mmol, 1.00 equiv) and 5-bromobenzooxazole (0.142 g, 0.717 mmol, 1.00 equiv) in toluene (4 mL) was added bis(cyclooctadiene)nickel(0) $(Ni(COD)_2, 0.200$ g, 0.717 mmol, 1.00 equiv), and the mixture was stirred at room temperature for 22q h. Pentane (16 mL) was added to the mixtures and the resulting solid was collected on a frit. The solid was washed with pentane (3×5 mL) and dried in vacuo to afford 0.260 g of the title compound as a yellow solid (97%). Anal: calcd for $C_{13}H_{20}BrN_3NiO \cdot (PhMe)_{0.15}$: C, 43.64; H, 5.53; N, 10.87; found: C, 43.44; H, 5.29; N, 10.33.

4-bromobenzoic Acid Succinimidyl Ester (S12)

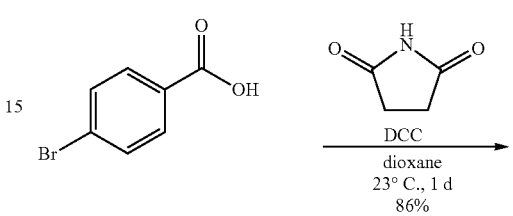

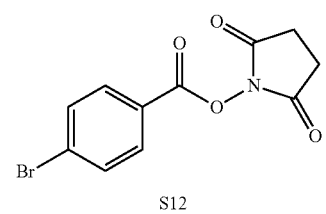

To 4-bromobenzoic acid (5.00 g, 24.9 mmol, 1.00 equiv) and N-hydroxysuccinimide (3.66 g, 31.8 mmol, 1.28 equiv) in a round-bottom flask in dioxane (120 mL) was added an dioxane solution (30 mL) that contained 1,3-dicyclohexylcarbodiimide (DCC) (6.77 g, 32.8 mmol, 1.32 equiv) dropwise over 5 min at 23 °C. The reaction mixture was stirring at 23 °C. for 24 h. The reaction mixture was concentrated in vacuo and the crude product was obtained by recrystallization in a cold acetone. The crude product was further purified by chromatography on silica gel eluting with hexanes/EtOAc 2:1 (v/v) to afford 6.34 g of the title compound as a colorless solid (86%).

Rf=0.25 (hexanes/EtOAc 2:1 (v/v)). NMR Spectroscopy: $^1H$ NMR (500 MHz, $CDCl_3$, 23 °C., δ): 7.99 (d, J=8.7 Hz, 2H), 7.67 (d, J=8.7 Hz, 1H), 2.90 (s, 4H). $^{13}C$ NMR (125 MHz, $CDCl_3$, 23 °C., δ): 169.2, 161.5, 132.5, 132.1, 130.6, 124.2, 25.8. These spectroscopic data correspond to the reported data.

Synthesis of Nickel(II) Aryl Bromide Complex (7k)

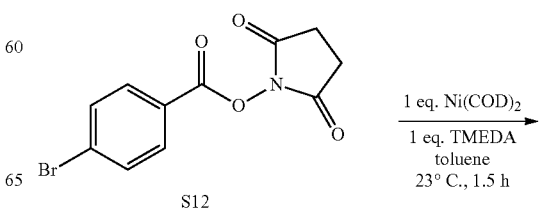

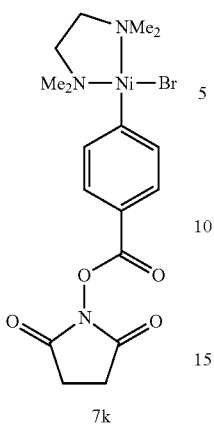

7k

To a solution of TMEDA (0.107 mL, 0.717 mmol, 1.00 equiv) and 4-bromobenzoic acid succinimidyl ester (S12) (0.214 g, 0.717 mmol, 1.00 equiv) in toluene (4 mL) was added bis(cyclooctadiene)nickel(0) (Ni(COD)$_2$, 0.200 g, 0.717 mmol, 1.00 equiv), and the mixture was stirred at room temperature for 1.5 h. Pentane (16 mL) was added to the mixtures and the resulting solid was collected on a frit. The solid was washed with pentane (3×5 mL) and dried in vacuo to afford 0.300 g of the title compound as an orange solid (89%). Anal: calcd for $C_{17}H_{24}BrN_3NiO_4$: C, 43.17; H, 5.11; N, 8.88; found: C, 43.65; H, 4.54; N, 7.48.

Synthesis of Nickel(II) Aryl Complex (1k)

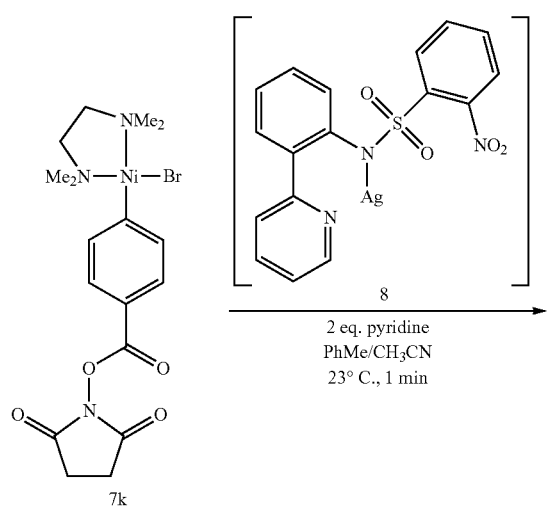

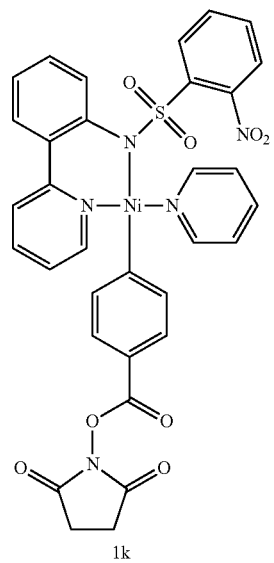

1k

To (2-(2-Pyridinyl)phenyl-2-nitrobenzenesulfonamide)silver(I) (8) (0.195 g, 0.423 mmol, 1.00 equiv) and nickel(II) aryl bromide complex (7k) (0.200 g, 0.423 mmol, 1.00 equiv) in a 20 mL vial was added an toluene solution (4 mL) that contained pyridine (66.9 mg, 68.1 L, 0.833 mmol, 2.00 equiv) at 23° C., followed by addition of acetonitrile (1.0 mL). After stirring for 1 min at 23, the solution was filtered through a glass frit and the filtered cake was extracted further with dichloromethane (3×5 mL). The combined filtrate was concentrated in vacuo and the resulting residue was purified by chromatography on silica gel eluting with hexanes/EtOAc 1:2 (v/v) to afford 0.152 g of the title compound as a yellow solid (51%). Rf=0.47 (hexanes/EtOAc 1:6 (v/v)). NMR Spectroscopy: $^1$H NMR (500 MHz, CDCl$_3$, 23° C., δ): 9.10 (d, J=5.2 Hz, 2H), 8.05 (d, J=5.6 Hz, 1H), 7.7 (d, J=7.9 Hz, 2H), 7.58-7.54 (m, 3H), 7.47-7.32 (m, 5H), 7.19-7.11 (m, 4H), 7.05-6.97 (m, 3H), 6.63-6.61 (m, 1H), 2.81 (s, 4H). $^{13}$C NMR (125 MHz CDCl$_3$, 23° C., δ): 174.2, 169.7, 162.9, 155.9, 152.3, 151.2, 147.0, 140.9, 137.6, 137.1, 136.4, 136.0, 135.4, 131.8, 130.5, 130.4, 130.1, 128.6, 128.4, 126.4, 124.6, 124.4, 122.9, 122.8, 122.0, 119.5, 25.7. Anal: calcd for $C_{33}H_{25}N_5NiO_8S$: C, 55.80; H, 3.55; N, 9.86; found: C, 55.53; H, 3.50; N, 9.61.

Synthesis of Nickel(II) Alkenyl Bromide Complex (7l)

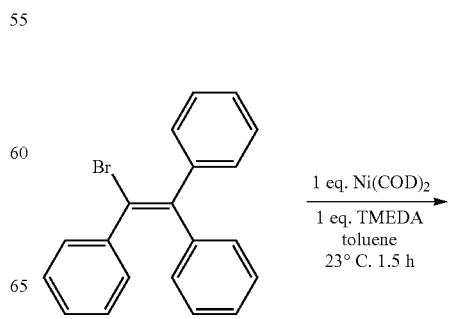

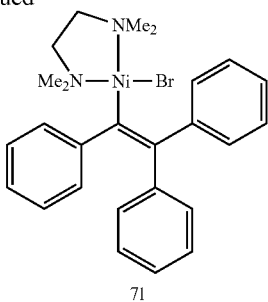

To a solution of TMEDA (0.107 mL, 0.717 mmol, 1.00 equiv) and bromotriphenylethylene (0.240 mg, 0.717 mmol, 1.00 equiv) in toluene (4 mL) was added bis(cyclooctadiene)nickel(0) (Ni(COD)$_2$, 0.200 g, 0.717 mmol, 1.00 equiv), and the mixture was stirred at room temperature for 40 min. Pentane (16 mL) was added to the mixtures and the resulting solid was collected on a frit. The solid was washed with pentane (3×5 mL) and dried in vacuo to afford 0.305 g of the title compound as a pink solid (86%). Attempts were made to get elemental analysis data but satisfactory one was not obtained. However, purification by chromatography on next step enables to access pure 1l.

Synthesis of Nickel(II) Alkenyl Complex (11)

concentrated in vacuo and the resulting residue was purified by chromatography on silica gel eluting with hexanes/EtOAc 1:2 (v/v) to afford 78.0 mg of the title compound as a yellow solid (52%). Rf=0.66 (hexanes/EtOAc 1:2 (v/v)). NMR Spectroscopy: $^1$H NMR (500 MHz, CDCl$_3$, 23 °C., δ): 9.85 (d, J=7.5 Hz, 1H), 8.77-8.60 (m, 3H), 7.80 (d, J=7.3 Hz, 1H), 7.74-7.70 (m, 1H), 7.49-7.30 (m, 6H), 7.24-6.82 (m, 15H), 6.69-6.59 (m, 4H), 6.40 (d, J=7.1 Hz, 1H),. $^{13}$C NMR (125 MHz, CDCl$_3$, 23 °C., δ): 160.7, 156.7, 156.5, 154.6, 152.3, 152.0, 151.9, 151.6, 148.0, 147.9, 147.3, 146.9, 145.2, 143.7, 143.2, 142.4, 141.8, 141.0, 137.4, 136.8, 136.5, 136.2, 135.9, 135.8, 135.2, 131.4, 131.1, 131.0, 130.7, 130.6, 130.3, 130.1, 130.0, 130.0, 129.9, 129.5, 129.4, 129.1, 128.9, 128.7, 128.2, 127.6, 127.5, 127.4, 127.2, 127.0, 127.0, 127.0, 126.5, 125.8, 125.3, 125.0, 124.6, 123.5, 123.4, 123.2, 123.0, 122.8, 122.6, 122.4, 122.0, 121.6. There are more $^{13}$C peaks than could be expected, possibly due to slow rotation about bonds as seen for similar complexes. Anal: calcd for C$_{42}$H$_{32}$N$_4$NiO$_4$S·(CH$_2$Cl$_2$)$_{0.15}$: C, 66.59; H, 4.28; N, 7.37; found: C, 66.71; H, 4.24; N, 7.51.

Example 3

Fluorination of Nickel (II) Aryl Complexes
4-Flurobiphenyl (2a)

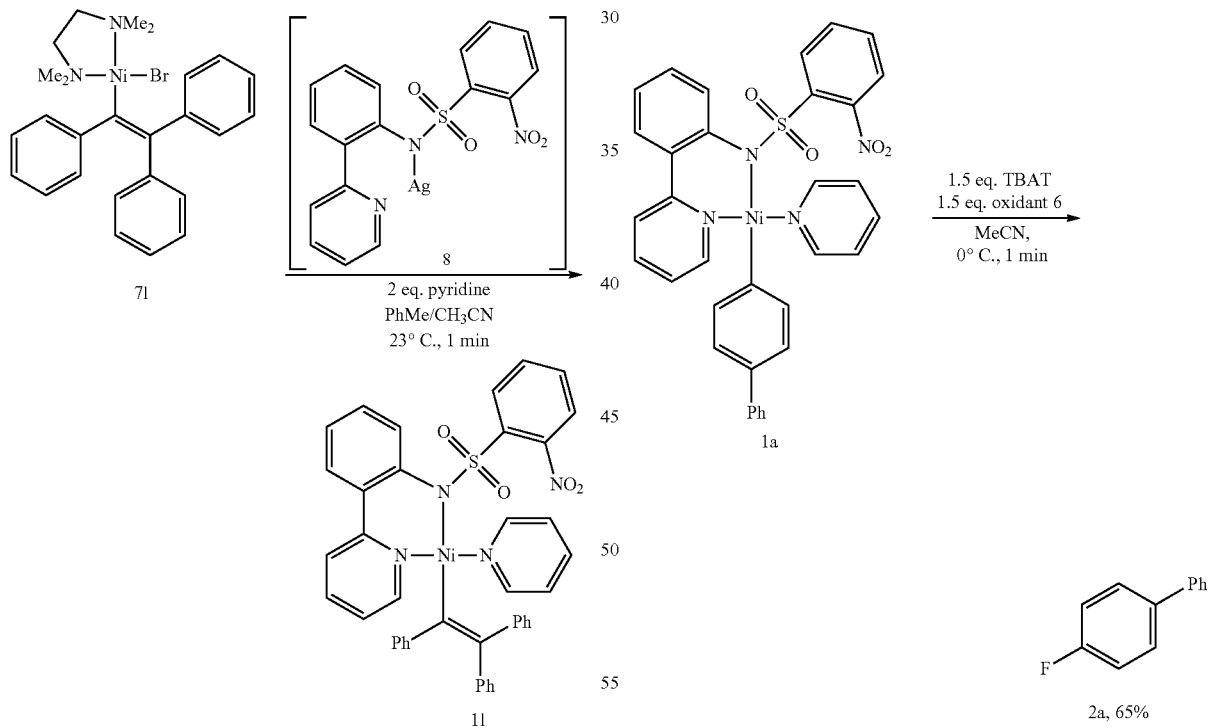

To (2-(2-Pyridinyl)phenyl-2-nitrobenzenesulfonamide)silver(I) (8) (0.0930 g, 0.417 mmol, 1.00 equiv) and nickel(II) alkenyl bromide complex (71) (0.100 g, 0.417 mmol, 1.00 equiv) in a 20 mL vial was added an toluene solution (3 mL) that contained pyridine (32.0 mg, 32.5 μL, 0.833 mmol, 2.00 equiv) at 23 °C., followed by addition of acetonitrile (0.5 mL). After stirring for 1 min at 23, the solution was filtered through a glass frit and the filtered cake was extracted further with dichloromethane (3×5 mL). The combined filtrate was In a glove box under a N$_2$ atmosphere, nickel (II) aryl complex 1a (40 mg, 0.62 mmol, 1.0 equiv), tetrabutylammonium difluorotriphenylsilicate (TBAT) (50 mg, 0.93 mmol, 1.5 equiv), and the oxidant (6) (50 mg, 0.93 mmol, 1.5 equiv) were placed in a 20 mL vial. The vial was taken out of the glove box, and immersed in an ice bath at 0 °C. for 5 minutes. To the reaction mixture was added quickly pre-cooled acetonitrile (4 mL) at 0 °C. in one portion and the solution was stirred for 1 min at 0 °C. After warmed to 23 °C., the solution was concentrated in vacuo and the residue is purified by chromatography on silica gel eluting with hexane/EtOAc 99:1 (v/v) to afford 6.9 mg of the title compound as a white solid (65% yield). TLC (hexane/EtOAc, 19:1 v/v): $R_F$=0.60; $^1$H—NMR (500 MHz, CDCl$_3$, 23 ° C.): δ7.60-7.54 (m, 4H), 7.47 (dd, J=7.5 Hz, 7.0 Hz, 2H), 7.36 (t, J=7.5 Hz, 1H), 7.14 (dd, J=8.0 Hz, 7.5 Hz, 2H); $^{13}$C—NMR (125 MHz, CDCl$_3$, 23 ° C.): δ162.7 (d, J=244 Hz), 140.5, 137.6, 129.0, 128.9 (d, J=8.5 Hz), 127.5, 127.3, 115.8 (d, J=21 Hz); $^{19}$F—NMR (375 MHz, CDCl$_3$, 23 ° C.): δ—116.2.

Rf=0.67 (pentane). NMR Spectroscopy: Selected $^1$H NMR (400 MHz, CDCl$_3$, 3 ° C., δ): 7.07-7.03 (m, 1H), 2.94-2.89 (m, 1H). $^{19}$F NMR (375 MHz, CD$_3$CN, 23 ° C., δ): —120.0.

2-(4-Fluorophenyl)ethyl Benzoate (2f)

1-Cyclohexyl-2-fluorobenzene (2e)

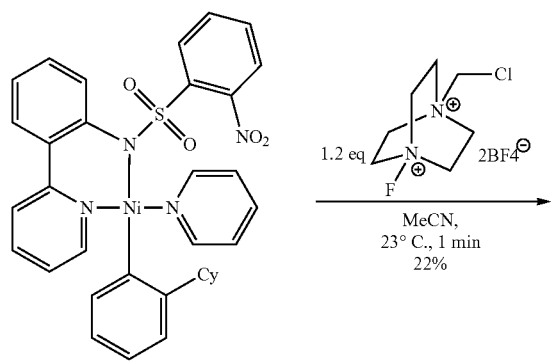

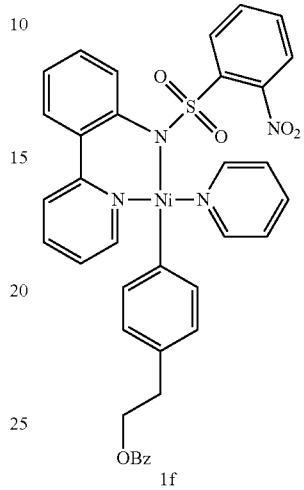

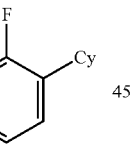

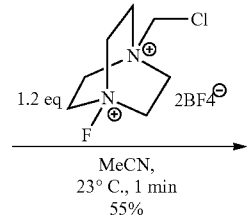

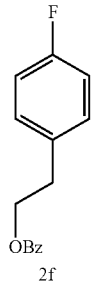

Nickel aryl complex 1e (50 mg, 0.077 mmol, 1.0 equiv) and 1-chloromethyl-4-fluoro-1,4-diazoniabicyclo[2.2.2]octane bis(tetrafluoroborate) (Selectfluor®) (33 mg, 0.092 mmol, 1.5 equiv) were placed in a 20 mL vial. To the reaction mixture was added acetonitrile (4 mL) at 23 ° C. in one portion and the solution was stirred for 1 min at 23 ° C. The solution was concentrated in vacuo and the residue is purified by chromatography on silica gel eluting with pentane to afford 8.1 mg of the title compound and cyclohexylbenzene as a 1:2 mixture (a colorless oil, 22% yield based on 1-cyclohexyl-2-fluorobenzene). Due to the difficulty of purification of the title compound and its volatility, the above mixture was used without further purification for identifying [$^{18}$F]2e by HPLC analysis.

Nickel aryl complex 1f (30 mg, 0.042 mmol, 1.0 equiv) and Selectfluor® (18 mg, 0.050 mmol, 1.2 equiv) were placed in a 20 mL vial. To the reaction mixture was added quickly acetonitrile (3 mL) at 23 ° C. in one portion and the solution was stirred for 1 min at 23 ° C. The solution was subsequently concentrated in vacuo and the residue is purified by chromatography on silica gel eluting with hexane/EtOAc 4:1 (v/v) to afford 5.6 mg of the title compound as a colorless solid (55% yield).

Rf=0.47 (hexanes/EtOAc 4:1 (v/v)). NMR Spectroscopy: $^1$H NMR (500 MHz, CDCl$_3$, 23 ° C., 6): 7.00 (d, J=7.5 Hz, 2H), 7.57-7.54 (m, 1H), 7.45-7.42 (m, 2H), 7.26-7.23 (m, 2H), 7.02-6.99 (m, 2H), 5.51 (t, J=6.5 Hz, 2H), 3.06 (t, J=6.5 Hz, 2H). $^{13}$C NMR (125 MHz, CDCl$_3$, 23 ° C., δ): 166.6, 161.9 (d, J=243 Hz), 133.7 (d, J=2.9 Hz), 133.1 (s), 130.5 (s), 130.4 (d, J=27 Hz), 129.7, 128.5, 115.5 (d, J=22 Hz), 65.5, 34.6. $^{19}$F NMR (375 MHz, CDCl$_3$, 23 ° C., δ): –116.8.

HRMS—FIA (m/z): calcd for $C_{15}H_{13}FO_2[M+H]+$, 245.0972; found, 245.0982.

N-(tert-butoxycarbonyl)-3,4-dhtert-butoxycarbonyloxy)-6-trimethylstannyl-L-phenylalaninemethyl ester (S13)

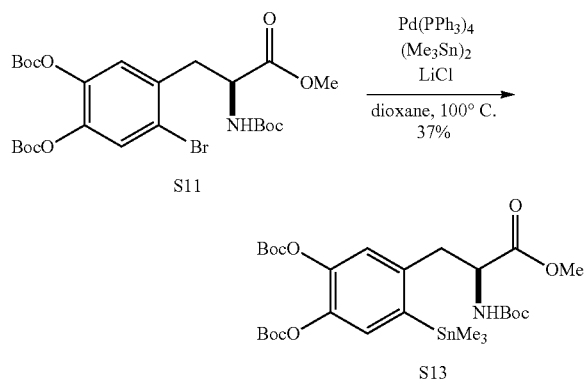

To N-(tert-butoxycarbonyl)-3,4-di(tert-butoxycarbonyloxy)-6-bromo-L-phenylalaninemethyl ester (S11) (1.00 g, 1.69 mmol, 1.00 equiv) in dioxane (20 mL) at 23 °C. was added lithium chloride (0.359 g, 8.47 mmol, 5.0 equiv), tetrakis(triphenylphosphine)palladium (0.391 g, 0.339 mmol, 20.0 mol%) and bis(trimethyltin) (1.11 g, 3.39 mmol, 2.00 equiv). After stirring for 5 hr at 100 °C., the reaction mixture was cooled to 23 °C. and concentrated in vacuo. The residue was purified by chromatography on silica gel, eluting with hexanes/EtOAc 5:1 (v/v), to afford 420 mg of the title compound as a colorless oil (37% yield). $R_f$=0.55 (hexane/EtOAc 3:1 (v/v)). NMR Spectroscopy: $^1$H NMR (500 MHz, CDCl$_3$, 23 °C., δ): 7.26 (br s, 1H), 7.08 (br s, 1H), 4.89 (d, J=7.6 Hz, 1H), 4.53-4.48 (m, 1H), 3.70 (s, 3H), 3.10-3.00 (m, 2H), 1.54 (s, 9H), 1.53 (s, 9H), 1.39 (s, 9H), 0.35 (s, 9H). $^{13}$C NMR (125 MHz, CDCl$_3$, 23 °C., δ): 172.7, 155.2, 150.9, 150.8, 142.7, 141.7, 141.5, 141.0, 130.4, 123.4, 110.8, 83.8, 80.2, 54.5, 52.5, 40.4, 28.3, 27.7, 27.7, -7.7. HRMS-FIA (m/z): calcd for $C_{28}H_{45}NO_{10}Sn[M+]^+$, 676.2144; found, 676.2171.

N-Boc-O-Boc-6-fluoro-DOPA methyl ester (2i)

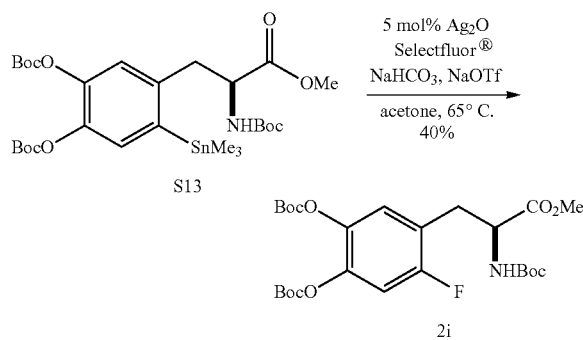

To N-Boc-O-Boc-6-trimethylstannyl-DOPA methyl ester (S13) (142 mg, 0.211 mmol, 1.00 equiv) in acetone (4 mL) at 23 °C. was added silver oxide (2.45 mg, 0.0106 mmol, 5.0 mol%), sodium bicarbonate (35.5 mg, 0.422 mmol, 2.0 equiv), sodium trifluoromethanesulfonate (36.3 mg, 0.211 mmol, 1.0 equiv) and Selectfluor® (112 mg, 0.317 mmol, 1.50 equiv). The reaction mixture was stirred for 5 hr at 65 °C. in a sealed vial. After cooling to 23 °C., the reaction mixture was filtered through a pad of Celite, eluting with CH$_2$Cl$_2$ and the filtrate was concentrated in vacuo. The residue was purified by chromatography on silica gel, eluting with hexane/EtOAc 4:1 (v/v), to afford 45.0 mg of the title compound as a colorless solid (40% yield).

$R_f$=0.37 (hexane/EtOAc 3:1 (v/v)). NMR Spectroscopy: $^1$H NMR (500 MHz, CDCl$_3$, 23 °C., δ): 7.05 (d, J=6.9 Hz, 1H), 7.02 (d, J=9.6 Hz, 1H), 5.07 (d, J=7.7 Hz), 4.57-4.53 (m, 1H), 3.71 (s, 3H), 3.18-3.04 (m, 2H), 1.54 (s, 9H), 1.53 (s, 9H), 1.41 (s, 9H). $^{13}$C NMR (125 MHz, CDCl$_3$, 23 °C., δ): 172.0, 158.2 (d, J=246 Hz), 155.1, 150.8, 150.4, 142.1 (d, J=12 Hz), 138.6, 125.4 (d, J=5.6 Hz), 121.5 (d, J=18 Hz), 110.8 (d, J=28 Hz), 84.4, 84.1, 80.2, 53.5, 52.6, 31.7, 28.4, 27.7, 27.7. $^{19}$F NMR (375 MHz, CDCl$_3$, 23 °C., δ): -117.6. Mass HRMS—FIA (m/z): calcd for $C_{25}H_{36}FNO_{10}[M+Na]^+$, 552.2215; found, 552.2214.

1-Fluoro-1,2,2-triphenylethylene (2l)

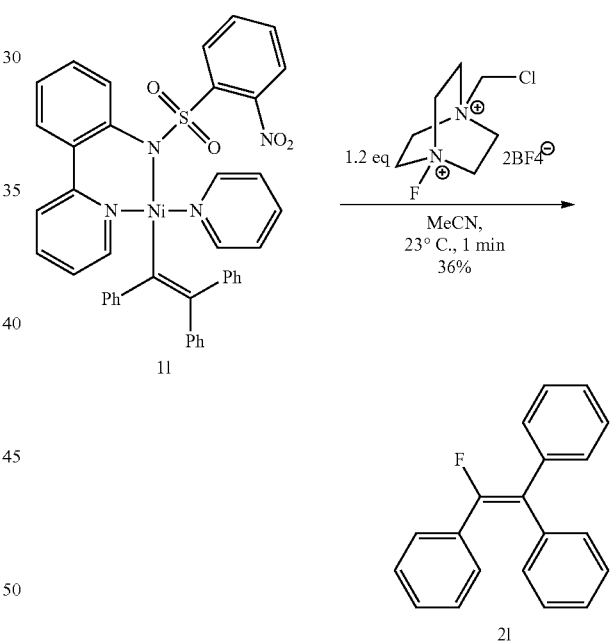

Nickel aryl complex 1l (30 mg, 0.040 mmol, 1.0 equiv) and Selectfluor® (17 mg, 0.048 mmol, 1.2 equiv) were placed in a 20 mL vial. To the reaction mixture was added quickly acetonitrile (3 mL) at 23 °C. in one portion and the solution was stirred for 1 min at 23 °C. The solution was subsequently concentrated in vacuo and the residue is purified by chromatography on silica gel eluting with Et$_2$O/CH$_2$Cl$_2$ 2:1 (v/v) to afford 4.0 mg of the title compound as a colorless solid (36% yield). Rf=0.88 (Et$_2$O/CH$_2$Cl$_2$ 2:1 (v/v)). NMR Spectroscopy: $^1$H NMR (500 MHz, CDCl$_3$, 23 °C., δ): 7.39-6.95 (m, 15H). $^{13}$C NMR (125 MHz, CDCl$_3$, 23 °C., δ): 130.8 (d, J=2.8 Hz), 130.1 (d, J=3.4 Hz), 130.8 (d, J=2.8 Hz), 129.2 (d, J=4.6 Hz), 128.7, 128.3, 128.2, 128.1, 128.1, 128.0, 127.7, 127.6, 127.5, 127.1. $^{19}$F NMR (375 MHz, CDCl$_3$, 23 °C., δ): −101.2.

Example 4

Synthesis of Nickel 2-Nitro-N-(2-(pyridin-2-yl)phenyl)benzenesulfonamide Complex (1x)

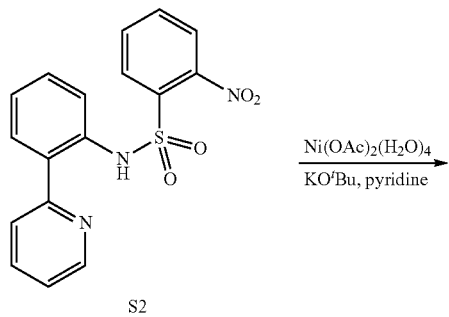

S2

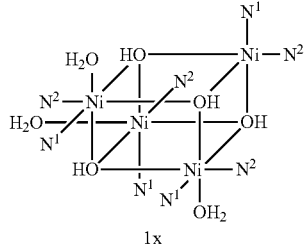

1x

A 250 ml, 2-neck, glass round-bottomed flask equipped with a teflon stirbar, adapter to a nitrogen line, and a plastic cap, was evacuated under vacuum, flame-dried, and refilled with nitrogen. Nickel acetate tetrahydrate (0.280 g, 1.23 mmol) was added, and the flask was evacuated under vacuum and backfilled with nitrogen. Distilled pyridine (16 ml) was added and the resulting dark blue solution was stirred. 2-Nitro-N-(2-(pyridin-2-yl)phenyl)benzenesulfonamide (0.400 g, 1.13 mmol) was dissolved in distilled pyridine (10 ml), and the resulting solution was added dropwise to the reaction via syringe, followed by a pyridine wash (1×2 ml). The mixture became a greenish-blue, homogeneous solution. In a glovebox, potassium tert-butoxide (0.253 g, 2.26 mmol) was weighed into a 20 ml glass vial, a septum affixed with tape, and removed from the glovebox. Distilled pyridine (7 ml) was added to obtain a homogeneous solution. The solution was added to the nickel reaction mixture dropwise via syringe followed by a pyridine wash (1×1 ml). The mixture became greenish-yellow, and a colorless precipitate formed. The mixture was stirred for 1 h at ambient temperature, and the mixture was concentrated in vacuo (50 °C. waterbath). The crude green-orange residue was dried in vacuo over 12 h. To the crude solid was added 10 ml THF, and the solution was filtered through Celite. The flask was rinsed (2×3 ml THF) and transferred to the filter pad successively. A turbid green solution was obtained. This solution was filtered through a second pad of Celite, rinsing with THF (1×2 ml) to obtain a homogeneous green solution. Water (0.1 ml) was added with vigorous stirring, effecting precipitation of a large amount of turquoise solid and a yellow supernatant. Additional water (0.4 ml) was added with stirring, and the entire mixture was transferred to a 20 ml glass vial with a THF wash (1×1 ml). The mixture was centrifuged, and the yellow supernatant was decanted leaving a turquoise solid. THF (6 ml) was added, the solution was mixed and centrifuged, and the colorless supernatant decanted. The process was repeated once further, and the remaining turquoise solid was dried in vacuo to afford a crude turquoise powder. The powder was suspended in dichoromethane (30 ml) in a 50 ml round-bottom flask, which was sealed and heated at 40 °C. for 5 min, then filtered through Celite, affording a homogenous green filtrate that was allowed to stand at ambient temperature overnight. The mixture was filtered through Celite to afford a homogeneous green filtrate. Hexanes (12 ml) was added dropwise to the mixture with vigorous stirring. After several minutes, a green precipitate formed. The flask was sealed and placed in a freezer for 8 h, following which time the mixture was centrifuged, and the supernatant decanted. The remaining solid was treated with pentane (10 ml), and the mixture was centrifuged, and the pentane decanted to yield the title compound 1x as a green powder (175 mg, 35%).

Alternative synthesis of nickel 2-Nitro-N-(2-(pyridin-2-yl)phenyl)benzenesulfonamide complex (1x)

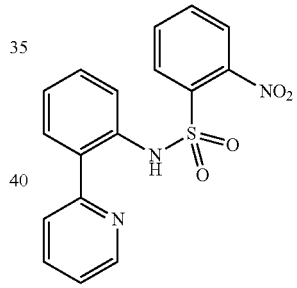

S2

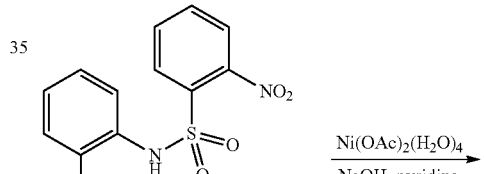

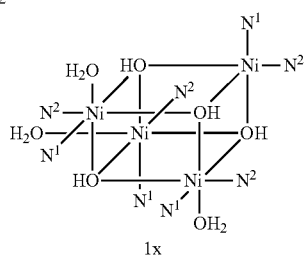

1x

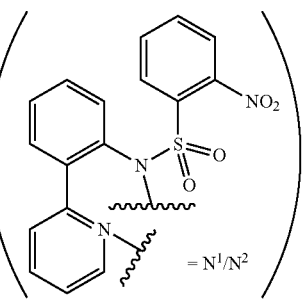

Figure 5A:
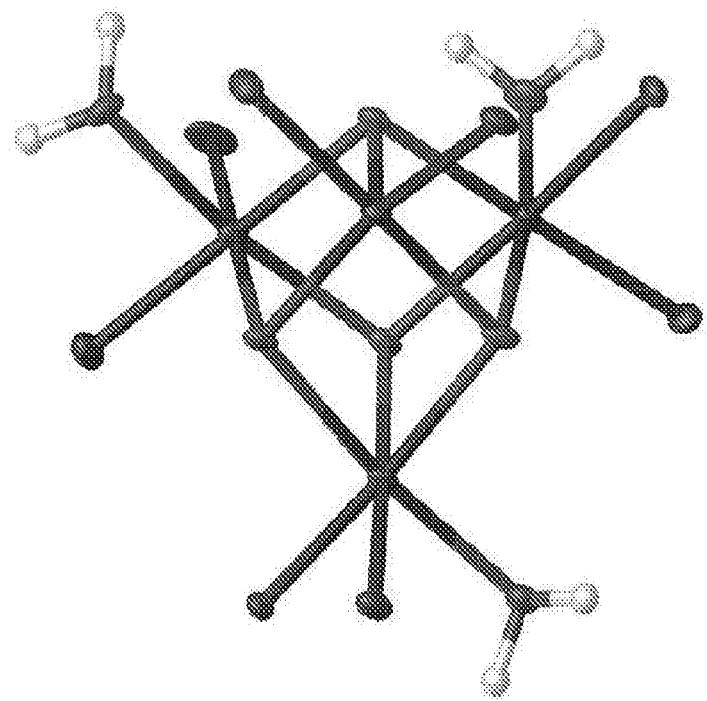
FIG. 5A shows the X-ray structure of nickel complex 1x without the rendering of the ligand backbone to enable a clear view of the cubane cluster.
Figure 5B:
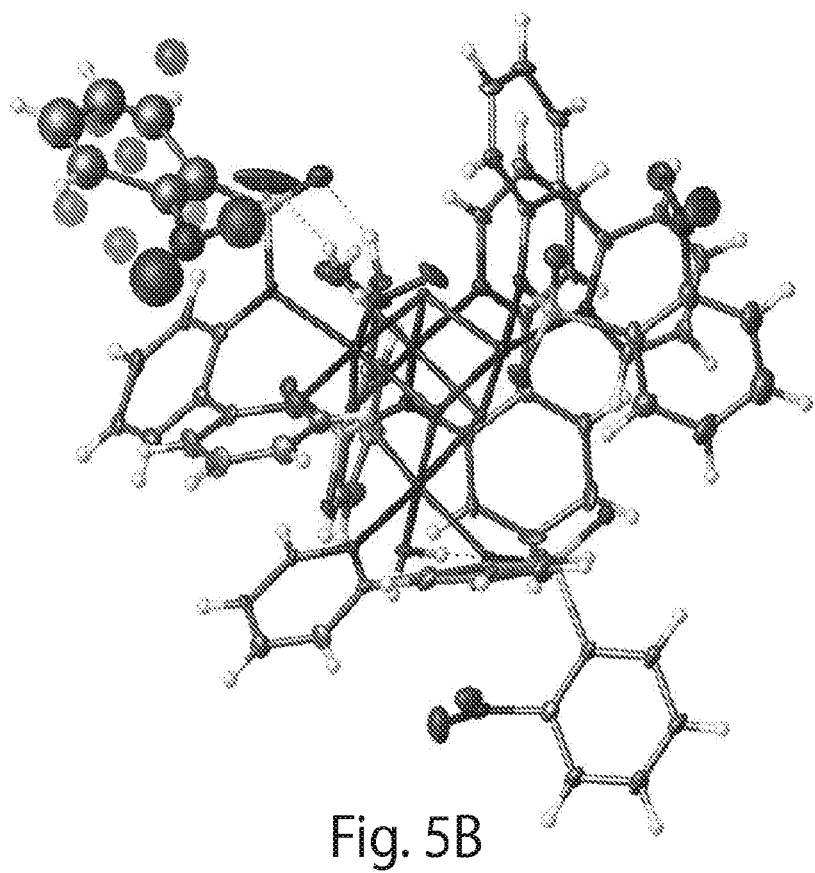
FIG. 5B shows the X-ray structure of complex 1x with complete rendering of the ligand backbone to enable a view of the entire complex and potential hydrogen bonding interactions.

To a 4 ml glass vial was added nickel acetate tetrahydrate (35 mg, 0.14 mmol), a Teflon stirbar, and distilled pyridine (1.4 ml). The vial was capped and the solution stirred vigorously to afford a blue solution. A solution of 2-nitro-N-(2-(pyridin-2-yl)phenyl)benzenesulfonamide (0.050 g, 0.14 mmol) in distilled pyridine (1.4 ml) was added to the reaction mixture dropwise. The resulting dark green-blue solution was stirred for 5 min, whereupon aqueous sodium hydroxide (2.55 M, 0.110 ml) was added dropwise. The mixture was sonicated briefly, leading to a yellow-green solution. Following 20 min, the solution was transferred to a 20 ml glass vial, and pentane (16 ml) was added dropwise with stirring, resulting in a biphasic system. The pentane layer was decanted, and ether (18 ml) was added. The mixture was stirred vigorously, leading to precipitation of a yellow solid. The mixture was centrifuged, the supernatant decanted, and the resulting residue was dried in vacuo. Minimal dicholoromethane was added to the residue, leading to the production of a quantity of orange solid. The mixture was filtered through Celite, affording a green solution that was concentrated in vacuo to afford the product 1x as a green solid (15.6 mg, 6%). An NMR sample was allowed to stand at ambient temperature for 2 days, during which time large green crystals grew. One of these crystals was analyzed by X-ray diffraction (see FIG. 5).

Example 5

Direct Insertion of Nickel 2-Nitro-N-(2-(pyridin-2-yl)phenyl)benzenesulfonamide Complex Into 1-(tert-butoxycarbonyl)-1H-indol-5-yl Boronic Acid to Produce 1c

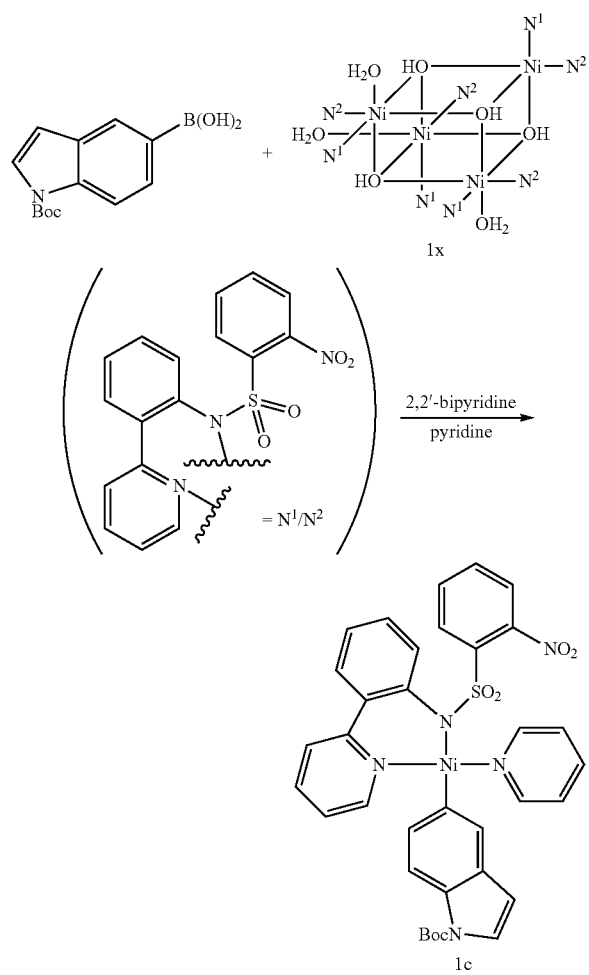

To a 20 mL glass vial equipped with a teflon stirbar was added 2,2'-bipyridine(12 mg, 0.077 mmol), 1-(tert-butoxycarbonyl)-1H-indol-5-yl boronic acid (0.020 g, 0.077 mmol), and the nickel complex 1x (34 mg, 0.019 mmol). Dry pyridine (3.1 ml) was added, and the reaction vial was purged with nitrogen and sealed with a cap. The solution was stirred to afford a green mixture with white suspended solid. The reaction was heated to 70° C. in an oil bath. Following 30 min, the mixture was cooled to room temperature. The resulting orange solution was concentrated in vacuo to give a brown residue. The solid was triturated with pentane (5×5 ml) and dried in vacuo. The solid was dissolved in dichloromethane, filtered through Celite, reduced in volume to approximately 1 ml in vacuo, following which pentane (15 ml) was added dropwise to the stirred mixture leading to formation of a yellow precipitate. The vial was centrifuged, and the organic layer was decanted. The residual yellow solid was sonicated with pentane (10 ml), centrifuged, the organic layer was decanted, and the process repeated a second time. The residual yellow solid was dried in vacuo to yield the product 1c as a yellow solid (52.0 mg, 96%).

Example 6. Radiochemistry

General Methods

No-carrier-added [$^{18}$F]fluoride was produced from water 97% enriched in $^{18}$O (Sigma-Aldrich®) by the nuclear reaction $^{18}$O(p,n)$^{18}$F using a Siemens Eclipse HP cyclotron and a silver-bodied target at MGH Athinoula A. Martinos Center for Biomedical Imaging. The produced [$^{18}$F]fluoride in water was transferred from the cyclotron target by helium push.

Liquid chromatographic analysis (LC) was performed with Agilent 1100 series HPLCs connected to a Carol and Ramsey Associates Model 105-S radioactivity detector. An Agilent Eclipse XDB-C18, 5 µm, 4.6×150 mm HPLC column was used for analytical analysis and a Waters Bondapak™ C18, 10 µm, 125 Å 7.6×300 mm HPLC was used for preparative HPLC. Analytical HPLC used the following mobile phases: 0.1% $CF_3CO_2H$ in water (A) 0.1% $CF_3CO_2H$ in acetonitrile (B). Program: 50% (B) for 2 minutes then a gradient 50-95% (B) over 8 minutes. Preparative HPLC used the following mobile phases: 0.1% $CF_3CO_2H$ in water (A) 0.1% $CF_3CO_2H$ in acetonitrile (B). Program: 40% (B). In the analysis of the $^{18}$F-labeled compounds, isotopically unmodified reference substances were used for identification. Radioactivity was measured in a Capintec, Inc. CRC-25PET ion chamber. Solvents and reagents for radiochemical experiments: Acetonitrile was distilled over $P_2O_5$. Water was obtained from a Millipore Milli-Q Integral Water Purification System. 18-crown-6 was sublimed.

Radiosynthesis of $^{18}$F-labeled Molecules

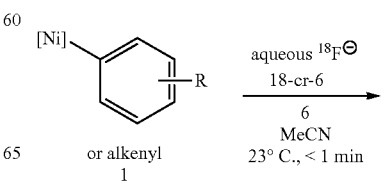

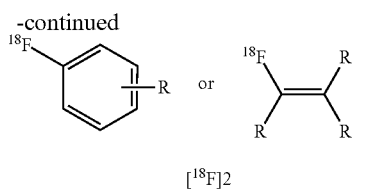

[¹⁸F]2

A portion of aqueous [¹⁸F]fluoride solution (20-50 μL, 2-5 mCi) obtained from a cyclotron was added to an acetonitrile solution (2.0-5.0 mL) which contained 20 mg of 18-cr-6. The acetonitrile solution (200-500 μl) was added quickly via the septum to the vial (4 mL) that contained 1.0 mg nickel complex 1 and 1.0 equiv of 6 (compared to 1). The solution became immediately pink or red or yellow depending on nickel complexes and then became colorless within 5 to 10 seconds. A capillary tube was then used to spot the solution on a silica gel TLC plate. The TLC plate was emerged in an appropriate organic solvent mixture. The TLC plate was scanned with a Bioscan AR-2000 Radio TLC Imaging Scanner. Results are shown on Table S1 (See also FIG. 3).

Effect of Additives on the Radiosynthesis of ¹⁸F-labeled Molecules

A portion of aqueous [¹⁸F]fluoride solution (as specified on Table S2) obtained from a cyclotron was added to an acetonitrile solution (0.5 mL) which contained 1 mg of 18-cr-6. To this solution was added a portion of saturated aqueous solution of a salt (as specified on Table S2), and the resulting solution was added quickly to a septum-capped vial containing 1.0 mg nickel complex 1 and 1.0 equiv of 6 (compared to 1). The solution became immediately pink or red or yellow depending on nickel complexes and then became colorless within 5 to 10 seconds. A capillary tube was then used to spot the solution on a silica gel TLC plate. The TLC plate was emerged in an appropriate organic solvent mixture. The TLC plate was scanned with a Bioscan AR-2000 Radio TLC Imaging Scanner. As shown on Table S2, a number of inorganic additives led to an increase in radiochemical yield. Most notably, $K_3PO_4$ doubled the radiochemical yield for the fluorination of an indole nickel complex.

Measurement of Radiochemical Yield

Radiochemical yield was determined by multiplying the percentage of radioactivity in the solution and the relative peak integrations of a radio TLC scan. After spotting the solution on a silica gel TLC plate, the remaining solution was transferred to the other vial. The radioactivity of the solution was measured in an ion chamber and the amount of radioactivity left on the walls of the initial vial was measured. After radio TLC quantification, the radiochemical yield was determined by multiplying the product quantified during TLC by the fraction of radioactivity in solution (typically 70-85%, see also FIG. 4).

TABLE S1

Radiochemical Yield Data

| Entry | Molecule | RTLC yield (%) | ¹⁸F in solution (%) | RCY (%) | Average RCY (%) |
|---|---|---|---|---|---|
| 1 | [¹⁸F]2a | 57 | 83 | 47 | 42 |
| 2 | | 68 | 80 | 54 | |
| 3 | | 49 | 82 | 40 | |
| 4 | | 48 | 82 | 39 | |
| 5 | | 49 | 81 | 40 | |
| 6 | | 38 | 82 | 31 | |
| 7 | [¹⁸F]2b | 69 | 83 | 58 | 51 |
| 8 | | 61 | 83 | 51 | |
| 9 | | 52 | 77 | 40 | |
| 10 | | 47 | 83 | 39 | |
| 11 | | 73 | 82 | 60 | |
| 12 | | 69 | 80 | 55 | |
| 13 | [¹⁸F]2c | 54 | 81 | 44 | 53 |
| 14 | | 72 | 84 | 61 | |
| 15 | | 72 | 84 | 60 | |
| 16 | | 64 | 84 | 54 | |
| 17 | | 57 | 78 | 45 | |
| 18 | | 69 | 80 | 56 | |
| 19 | [¹⁸F]2d | 28 | 78 | 22 | 17 |
| 20 | | 18 | 80 | 14 | |
| 21 | | 19 | 79 | 15 | |
| 22 | | 19 | 79 | 15 | |
| 23 | | 24 | 79 | 19 | |
| 24 | | 21 | 76 | 16 | |
| 25 | [¹⁸F]2e | 40 | 80 | 32 | 21 |
| 26 | | 24 | 82 | 20 | |
| 27 | | 21 | 82 | 17 | |
| 28 | | 25 | 78 | 19 | |
| 29 | | 26 | 73 | 19 | |
| 30 | | 26 | 73 | 19 | |
| 31 | [¹⁸F]2f | 57 | 83 | 47 | 54 |
| 32 | | 57 | 84 | 48 | |
| 33 | | 54 | 82 | 44 | |
| 34 | | 72 | 86 | 62 | |
| 35 | | 78 | 84 | 66 | |
| 36 | | 75 | 75 | 56 | |
| 37 | [¹⁸F]2g | 70 | 89 | 62 | 58 |
| 38 | | 66 | 88 | 58 | |
| 39 | | 76 | 87 | 66 | |
| 40 | | 66 | 84 | 55 | |
| 41 | | 61 | 79 | 48 | |
| 42 | | 72 | 81 | 58 | |
| 43 | [¹⁸F]2h | 60 | 83 | 50 | 43 |
| 44 | | 66 | 84 | 55 | |
| 45 | | 52 | 81 | 42 | |
| 46 | | 44 | 73 | 32 | |
| 47 | | 42 | 80 | 34 | |
| 48 | | 56 | 80 | 45 | |
| 49 | [¹⁸F]2i | 24 | 70 | 17 | 15 |
| 50 | | 22 | 65 | 14 | |
| 51 | | 41 | 68 | 28 | |
| 52 | | 14 | 76 | 11 | |
| 53 | | 17 | 59 | 10 | |
| 54 | | 13 | 64 | 8 | |
| 55 | [¹⁸F]2j | 45 | 84 | 38 | 38 |
| 56 | | 53 | 83 | 44 | |
| 57 | | 51 | 78 | 40 | |
| 58 | | 51 | 79 | 40 | |
| 59 | | 33 | 77 | 25 | |
| 60 | | 49 | 79 | 39 | |
| 61 | [¹⁸F]2k | 27 | 74 | 20 | 21 |
| 62 | | 30 | 75 | 23 | |
| 63 | | 34 | 76 | 26 | |
| 64 | | 32 | 77 | 25 | |
| 65 | | 21 | 79 | 17 | |
| 66 | | 20 | 75 | 15 | |
| 67 | [¹⁸F]2l | 11 | 86 | 9 | 13 |
| 68 | | 14 | 82 | 11 | |
| 69 | | 15 | 84 | 13 | |
| 70 | | 14 | 81 | 11 | |
| 71 | | 20 | 82 | 16 | |
| 72 | | 17 | 86 | 15 | |

TABLE S2

Effect of Additives on Radiochemical Yield

| Salt | Volume of Sat. Solution | $CH_3CN$ + 0.1 mL Crown Ether 10 mg/mL | Volume of $^{18}F$ solution | water (%) | Entry 1 RCY (%) | Entry 2 | Entry 3 | Entry 4 |
|---|---|---|---|---|---|---|---|---|
| NaCl | 1 µL | 0.5 mL | 5 µL | 1.09 | 20.93 | 22.93 | | |
| $KClO_4$ | 1 µL | 0.5 mL | 5 µL | 1.09 | 45.85 | | | |
| $KNO_3$ | 1 µL | 0.5 mL | 5 µL | 1.09 | 6.23 | 4.16 | | |
| $K_3PO_4$ | 1 µL | 0.5 mL | 5 µL | 1.09 | 69.89 | 26.29 | | |
| $K_3PO_4$ | 2 µL | 0.5 mL | 3.8 µL | 0.95 | 79.93 | 77.9 | 82.6 | 77.3 |
| $Na_2HPO_3$ | 1 µL | 0.5 mL | 7 µL | 0.90 | 47.03 | | | |
| $Na_2SO_4$ | 1 µL | 0.5 mL | 7 µL | 0.90 | 41.4 | | | |

Other Embodiments

The foregoing has been a description of certain embodiments of the invention. Those of ordinary skill in the art will appreciate that various changes and modifications to this description may be made without departing from the spirit or scope of the present invention, as defined in the following claims.

The invention claimed is:

1. A method of producing a fluorinated organic compound, the method comprising mixing a nickel comprising complex of formula (I):

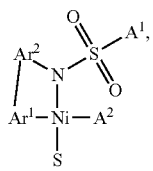

(I)

wherein:
   $Ar^1$ is aryl or heteroaryl substituted with n occurrences of $R^1$;
   $Ar^2$ is aryl or heteroaryl substituted with m occurrences of $R^2$;
   $A^1$ is $C_{1-6}$ alkyl, $C_{1-6}$ alkoxy, $C_{3-7}$ cycloalkyl, $C_{2-6}$ alkenyl, C(O)—$R^6$, C(O)O$R^6$, —$NH_2$, —$NHR^7$, —$N(R^7)_2$, $NO_2$, —OH, —$OR^6$, aryl, heteroaryl or heterocyclyl, wherein each alkyl, alkoxy, cycloalkyl, alkenyl, aryl, heteroaryl or heterocyclyl can be further substituted with o occurrences of $R^3$;
   $A^2$ is an N-heterocyclic carbene, phosphine, phosphate or heteroaryl substituted with p occurrences of $R^4$;
   S is a substrate wherein the substrate is linked through an aryl, heteroaryl or alkenyl moiety present in the substrate;
   each $R^1$, $R^2$, $R^3$ and $R^4$ is independently halo, $C_{1-6}$ alkyl, $C_{1-6}$ alkoxy, $C_{3-7}$ cycloalkyl, $C_{2-6}$ alkenyl, C(O)—$R^6$, C(O)O$R^6$, —$NH_2$, —$NHR^7$, —$N(R^7)_2$, $NO_2$, —OH, —$OR^6$, aryl, heteroaryl or heterocyclyl, wherein each alkyl, alkoxy, cycloalkyl, alkenyl, aryl, heteroaryl or heterocyclyl can be further substituted with 0-3 occurrences of $R^8$;
   $R^6$ is $C_{1-6}$ alkyl, $C_{1-6}$ alkenyl, $C_{3-7}$ cycloalkyl, —C(O)O—$C_{1-6}$ alkyl, aryl, heteroaryl or heterocyclyl;
   each $R^7$ is independently $C_{1-6}$ alkyl, $C_{1-6}$ alkenyl, $C_{3-7}$ cycloalkyl, —C(O)—$C_{1-6}$ alkyl, —C(O)O—$C_{1-6}$ alkyl, aryl, heteroaryl or heterocyclyl;
   each $R^8$ is independently halo, $C_{1-6}$ alkyl, $C_{1-6}$ alkoxy, $C_{1-6}$ alkenyl, $C_{3-7}$ cycloalkyl, $C_{1-6}$ alkyl-amine, —C(O)—$C_{1-6}$ alkyl, —C(O)O—$C_{1-6}$ alkyl, $C_{0-6}$ alkyl—$NHR^7$, aryl, aryloxy, aralkyl, heteroaryl, heteroaralkyl, heterocyclyl or heterocyclylalkyl or wherein two adjacent $R^8$ moieties, taken together with the atoms to which they are attached, form a $C_{3-7}$ cycloalkyl, aryl, heteroaryl or heterocyclyl group, wherein each alkyl, alkoxy, alkenyl, cycloalkyl, aryl; and m, n, o and p are each independently an integer from 0-5;
with a source of fluorine and an organic compound under conditions sufficient to fluorinate the organic compound, thereby providing a fluorinated organic compound.

2. The method of claim 1, wherein the source of fluorine is a fluoride source comprising water or a fluorinating agent.

3. The method of claim 1, wherein source of fluorine comprises $^{18}F$ or $^{19}F$.

4. The method of claim 1, wherein the nickel complex of formula (I) is a complex of formula (II):

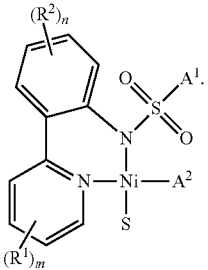

(II)

5. The method of claim 4, wherein $A^1$ is aryl substituted with o occurrences of $R^3$.

6. The method of claim 1, wherein the nickel complex of formula (I) is a complex of formula (III):

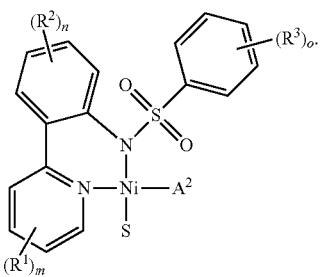

(III)

7. The method of claim 6, wherein $A^2$ is heteroaryl substituted with p occurrences of $R^4$.

8. The method of claim 1, wherein the nickel complex of formula (I) is a complex of formula (IV):

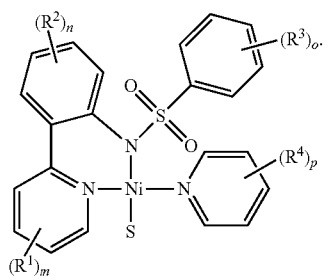

9. The method of claim 1, wherein the nickel complex of formula (I) is a complex of formula (V):

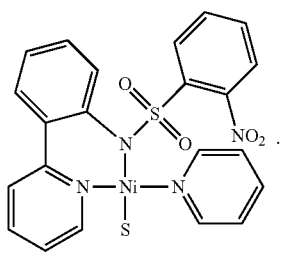

10. The method of claim 1, wherein S is an optionally substituted aryl comprising substrate an optionally substituted heteoaryl or an optionally substituted $C_{2-6}$ alkenyl.

11. The method of claim 10, wherein S is selected from one of the following:

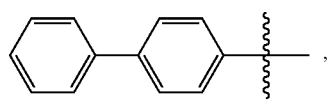,

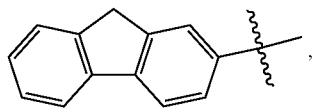,

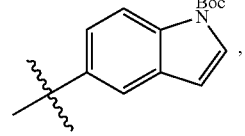,

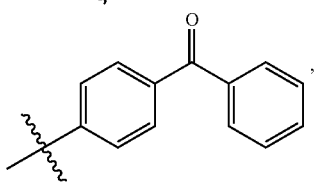,

-continued

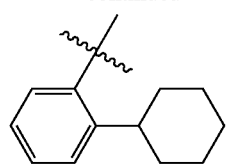,

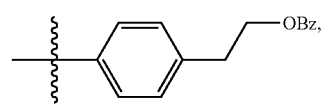,

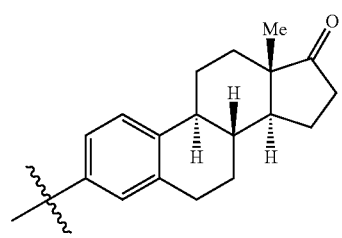,

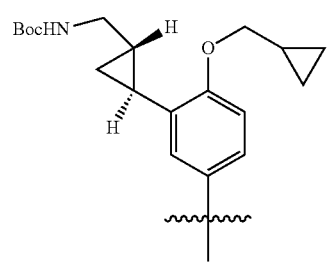,

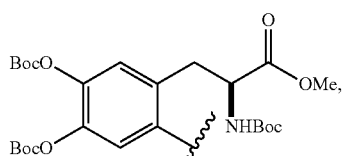,

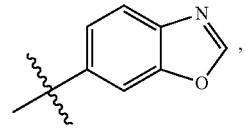,

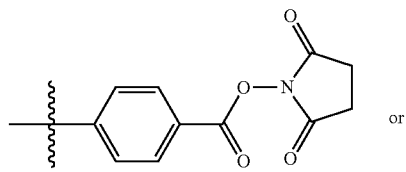 or

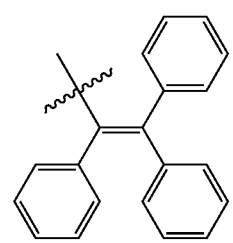.

12. The method of claim 1, wherein the complex of formula (I) is selected from the following:
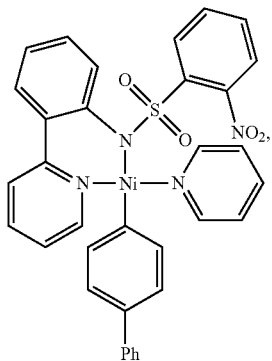
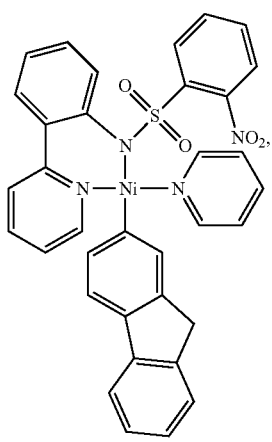
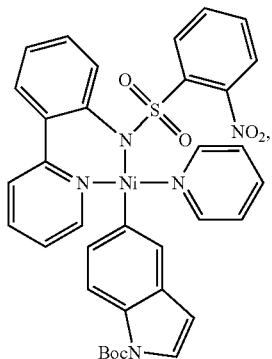
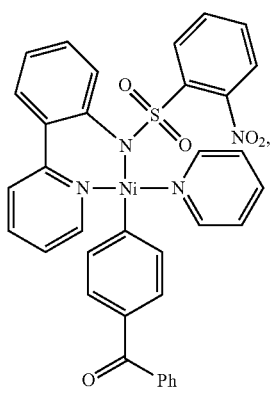
-continued
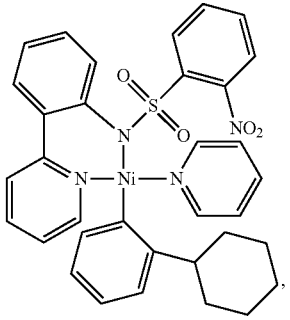
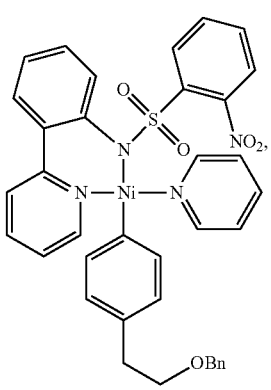

-continued

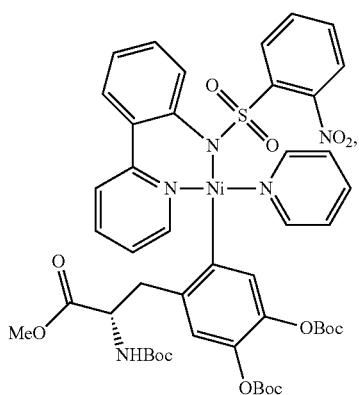

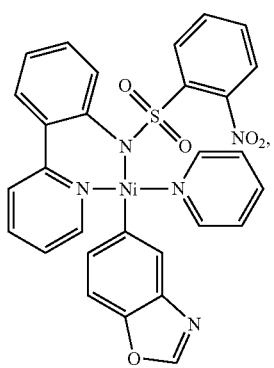

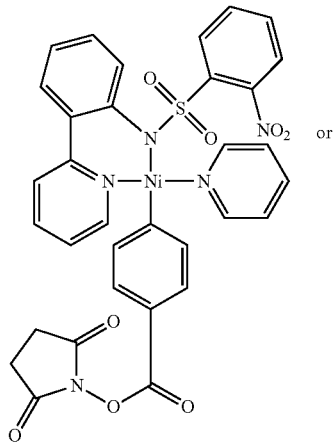

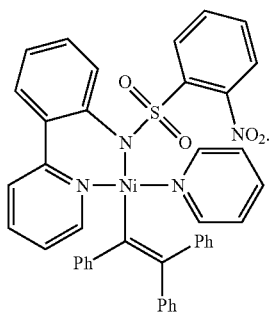

13. The method of claim 1, further comprising an oxidant, wherein the oxidant is a compound of formula (IX):

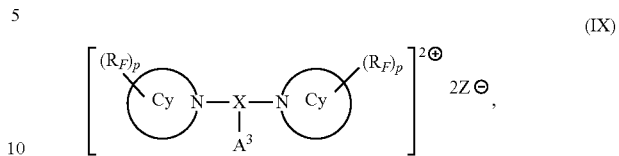

wherein

X is a halogen $A^3$ is an aryl or heteroaryl group;

Cy taken together with the nitrogen atom to which it is attached forms a heterocyclyl or heteroaryl ring;

each occurrence of $R_F$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —OR''; —C(=O)R''; —CO$_2$R''; —CN; —SCN; —SR''; —SOR''; —SO$_2$R''; —NO$_2$; —N(R'')$_2$; —NHC(O)R''; or —C(R'')$_3$; wherein each occurrence of R'' is independently a hydrogen, a protecting group, an aliphatic moiety, a heteroaliphatic moiety, an aryl moiety; a heteroaryl moiety; alkoxy; aryloxy; alkylthio; arylthio; amino, alkylamino, dialkylamino, heteroaryloxy; or heteroarylthio moiety; and Z is an anion.

14. The method of claim 13, wherein the oxidant is selected from the following:

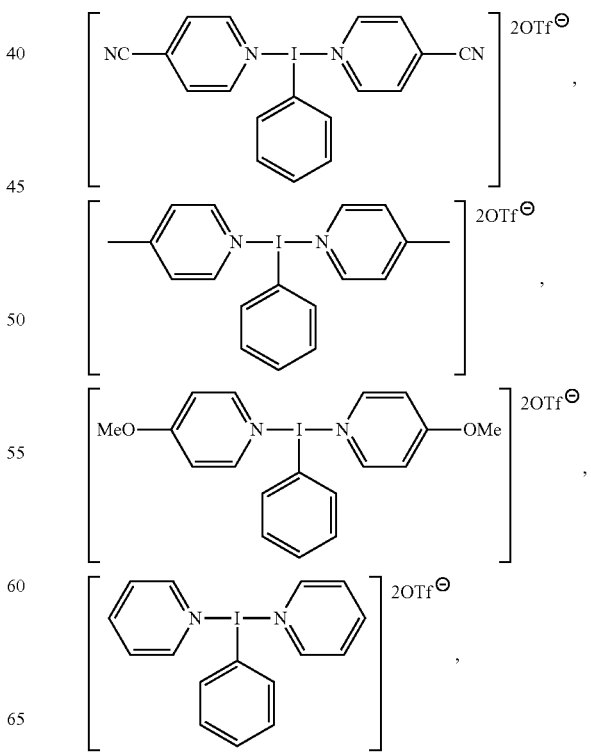

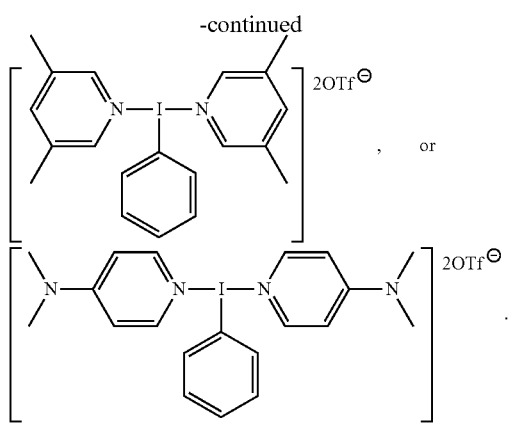
15. The method of claim 1, wherein the fluorinated organic compound is selected from the following:
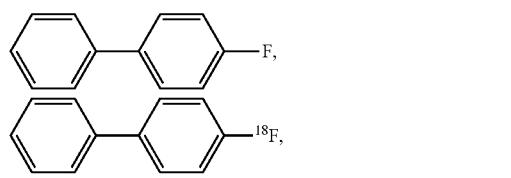
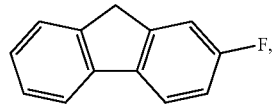
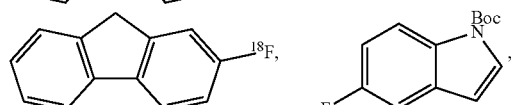
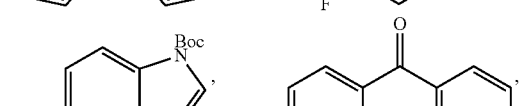
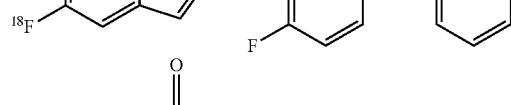
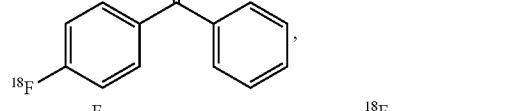
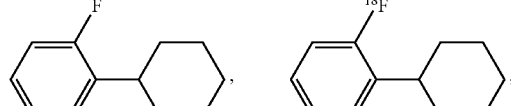
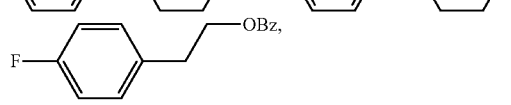
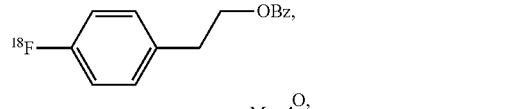
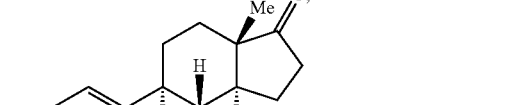
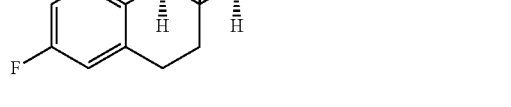
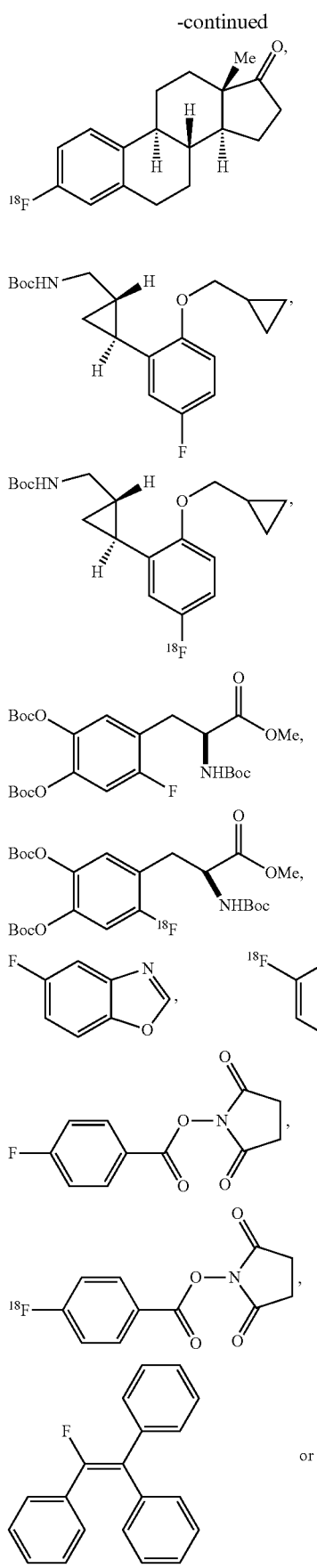

-continued

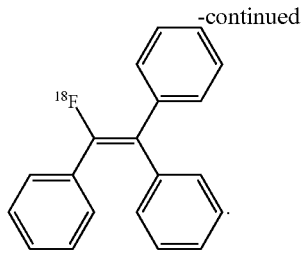

16. The method of claim 1, wherein the method further comprises adding a salt to the source of fluorine.

17. The method of claim 1, wherein the method further comprises adding a salt to the nickel comprising complex.

18. The method of claim 1, wherein the method further comprises including a salt in the mixture containing the nickel comprising complex and source of fluorine.

19. A method of making a nickel complex of formula (I), the method comprising treating an organic compound of formula (VI):

with tetramethylethylenediamine and bis(1,5-cyclooctadiene)nickel to provide a nickel complex of formula (VII):

the method further comprising, treating a nickel complex of formula (VII) with a silver compound of formula (VIII) and $A^2$:

to provide a nickel complex of formula (I), wherein
X is a leaving group; and
$Ar^1, Ar^2, A^1, A^2, A^3, R^1, R^2, R^3, R^4, R^6, R^7, R^8$, m, n, o and p are as defined for formula (I).

20. A nickel complex of formula (I):

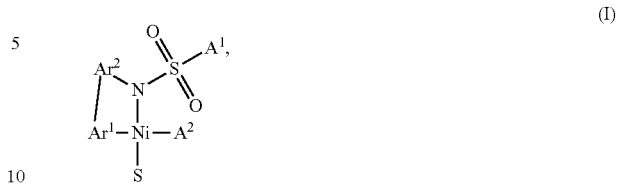

wherein:
$Ar^1$ is aryl or heteroaryl substituted with n occurrences of $R^1$;
$Ar^2$ is aryl or heteroaryl substituted with m occurrences of $R^2$;
$A^1$ is $C_{1-6}$ alkyl, $C_{1-6}$ alkoxy, $C_{3-7}$ cycloalkyl, $C_{2-6}$ alkenyl, C(O)—$R^6$, C(O)O—$R^6$, —$NH_2$, —$NHR^7$, —$N(R^7)_2$, $NO_2$, —OH, —$OR^6$, aryl, heteroaryl or heterocyclyl, wherein each alkyl, alkoxy, cycloalkyl, alkenyl, aryl, heteroaryl or heterocyclyl can be further substituted with o occurrences of $R^3$;
$A^2$ is an N-heterocyclic carbene, phosphine, phosphate or heteroaryl substituted with p occurrences of $R^4$;
S is a substrate wherein the substrate is linked through an aryl, heteroaryl or alkenyl moiety present in the substrate;
each $R^1$, $R^2$, $R^3$ and $R^4$ is independently halo, $C_{1-6}$ alkyl, $C_{1-6}$ alkoxy, $C_{3-7}$ cycloalkyl, $C_{2-6}$ alkenyl, C(O)—$R^6$, C(O)O$R^6$, —$NH_2$, —$NHR^7$, —$N(R^7)_2$, $NO_2$, —OH, —$OR^6$, aryl, heteroaryl or heterocyclyl, wherein each alkyl, alkoxy, cycloalkyl, alkenyl, aryl, heteroaryl or heterocyclyl can be further substituted with 0-3 occurrences of $R^8$;
$R^6$ is $C_{1-6}$ alkyl, $C_{1-6}$ alkenyl, $C_{3-7}$ cycloalkyl, —C(O)O—$C_{1-6}$ alkyl, aryl, heteroaryl or heterocyclyl;
each $R^7$ is independently $C_{1-6}$ alkyl, $C_{1-6}$ alkenyl, $C_{3-7}$ cycloalkyl, —C(O)—$C_{1-6}$ alkyl, —C(O)O—$C_{1-6}$ alkyl, aryl, heteroaryl or heterocyclyl;
each $R^8$ is independently halo, $C_{1-6}$ alkyl, $C_{1-6}$ alkoxy, $C_{1-6}$ alkenyl, $C_{3-7}$ cycloalkyl, $C_{1-6}$ alkyl-amine, —C(O)—$C_{1-6}$ alkyl, —C(O)O—$C_{1-6}$ alkyl, $C_{0-6}$ alkyl—$NHR^7$, aryl, aryloxy, aralkyl, heteroaryl, heteroaralkyl, heterocyclyl or heterocyclylalkyl or wherein two adjacent $R^8$ moieties, taken together with the atoms to which they are attached, form a $C_{3-7}$ cycloalkyl, aryl, heteroaryl or heterocyclyl group, wherein each alkyl, alkoxy, alkenyl, cycloalkyl, aryl; and
m, n, o and p are each independently an integer from 0-5.

* * * * *